United States Patent [19]

Myers

[11] Patent Number: 5,763,451
[45] Date of Patent: Jun. 9, 1998

[54] DYNEMICIN ANALOGS

[75] Inventor: Andrew Gordon Myers, Pasadena, Calif.

[73] Assignee: California Institute of Technology, Pasadena, Calif.

[21] Appl. No.: 598,316

[22] Filed: Feb. 8, 1996

Related U.S. Application Data

[63] Continuation-in-part of Ser. No. 281,340, Jul. 27, 1994, abandoned.
[51] Int. Cl.⁶ .................. A61K 31/44; C07D 221/18; C07D 491/00; C07D 513/00
[52] U.S. Cl. .................. 514/279; 514/280; 546/43
[58] Field of Search ............... 546/43; 514/279, 514/280

[56] References Cited

U.S. PATENT DOCUMENTS

| | | | |
|---|---|---|---|
| 4,916,065 | 4/1990 | Ohkuma et al. | 546/34 |
| 5,116,845 | 5/1992 | Ohkuma | 514/279 |
| 5,162,330 | 11/1992 | Saitoh et al. | 514/279 |
| 5,276,159 | 1/1994 | Smith et al. | 546/43 |
| 5,281,710 | 1/1994 | Smith et al. | 546/34 |
| 5,500,432 | 3/1996 | Nicolaou et al. | 514/281 |
| 5,622,958 | 4/1997 | Danishefsky et al. | 514/280 |

FOREIGN PATENT DOCUMENTS 9202522  2/1992  WIPO.

OTHER PUBLICATIONS

Yoon, T., et al., "Experiments Directed Toward a Total Synthesis of Dynemicin A: A Solution to the Stereochemical Problem," *J. Org. Chem.*, 59(14):3752–3754 (1994).

Shair, M.D., et al., "A Remarkable Cross Coupling Reaction to Construct the Enediyne Linkage Relevant to Dynemicin A: Synthesis of the Deprotected ABC System," *J. Org. Chem.*, 59(14):3755–3757 (1994).

Myers et al., *J. Am. Chem. Soc.*, 116:11550–11557 (1994).

"Total Synthesis of Dynemicin A Achieved," *Chemical & Eng. News*, Jan. 23, 1995, p. 22.

Taunton, J., et al., "Total Systheses of Di– and Tri–O–methyl Dynemicin A Methyl Esters," *Jm. Am. Chem. Soc.*, 115(22):10378–10379 (1993).

Porco, J.A., et al., "Transannular Diels–Alder Route to Systems Related to Dynemicin A," *J. Am. Chem. Soc.*, 112:7410–7411 (1990).

Wood, J.L., et al., "Application of the Allylic Diazene Rearrangement: Synthesis of the Enediyne–Bridged Tricyclic Core of Dynemicin A," *J. Am. Chem. Soc.*, 114(14):5898–5900 (1992).

Chikashita, H., et al., "Synthesis of the Angular Anthraquinone Subunit of Dynemicin A," *J. Org. Chem.*, 56(5):1692–1694 (1991).

*Primary Examiner*—Mukund J. Shah
*Assistant Examiner*—Bruck Kifle
*Attorney, Agent, or Firm*—Flehr Hohbach Test Albritton & Herbert LLP

[57] ABSTRACT

Non-naturally occuring dynemicin analogs are provided, which are useful as DNA cleaving agents, cytotoxic agents, and/or anti-tumor compounds. Methods of making dynemicin analogs are also provided.

14 Claims, 16 Drawing Sheets

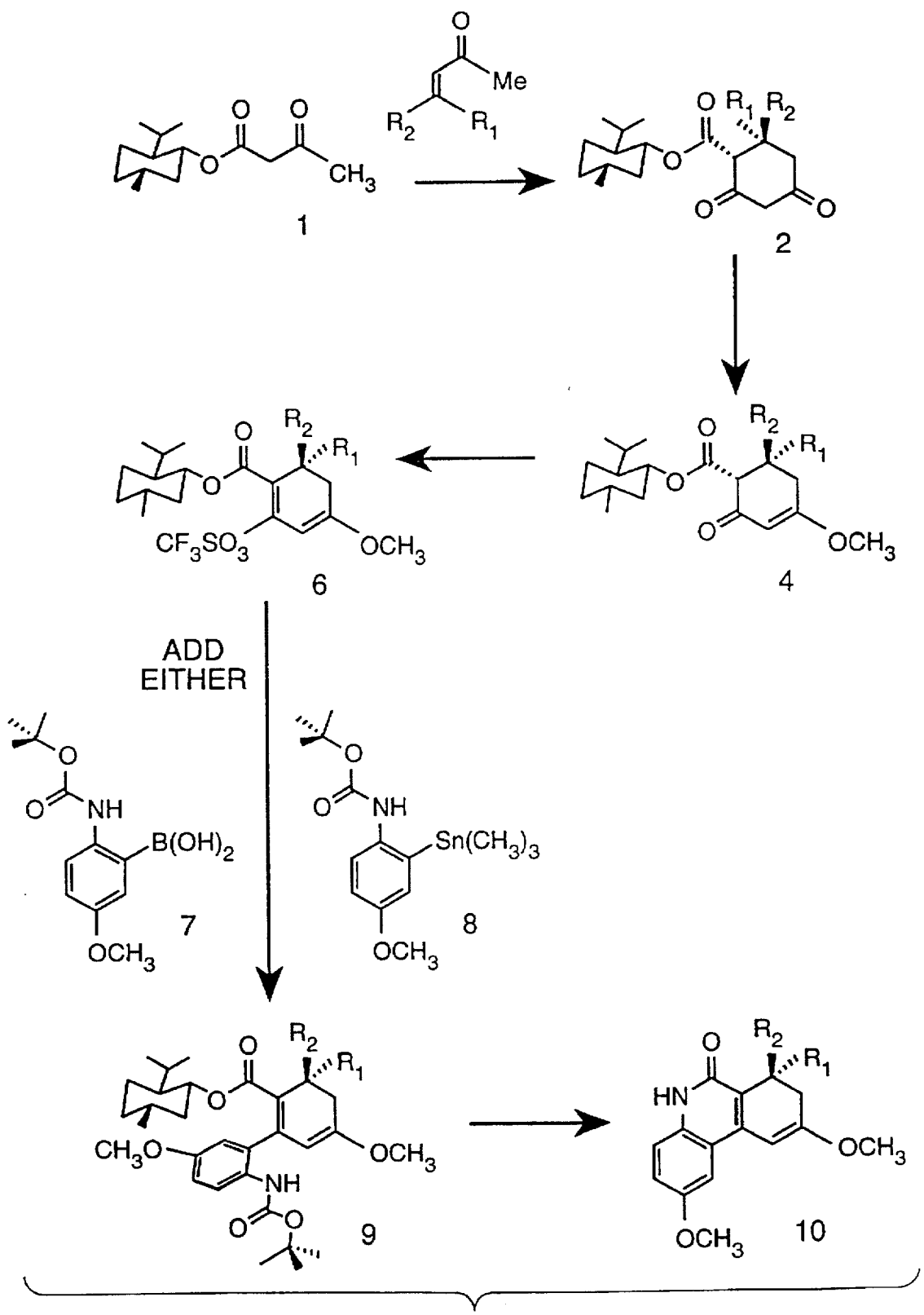
FIG._1A

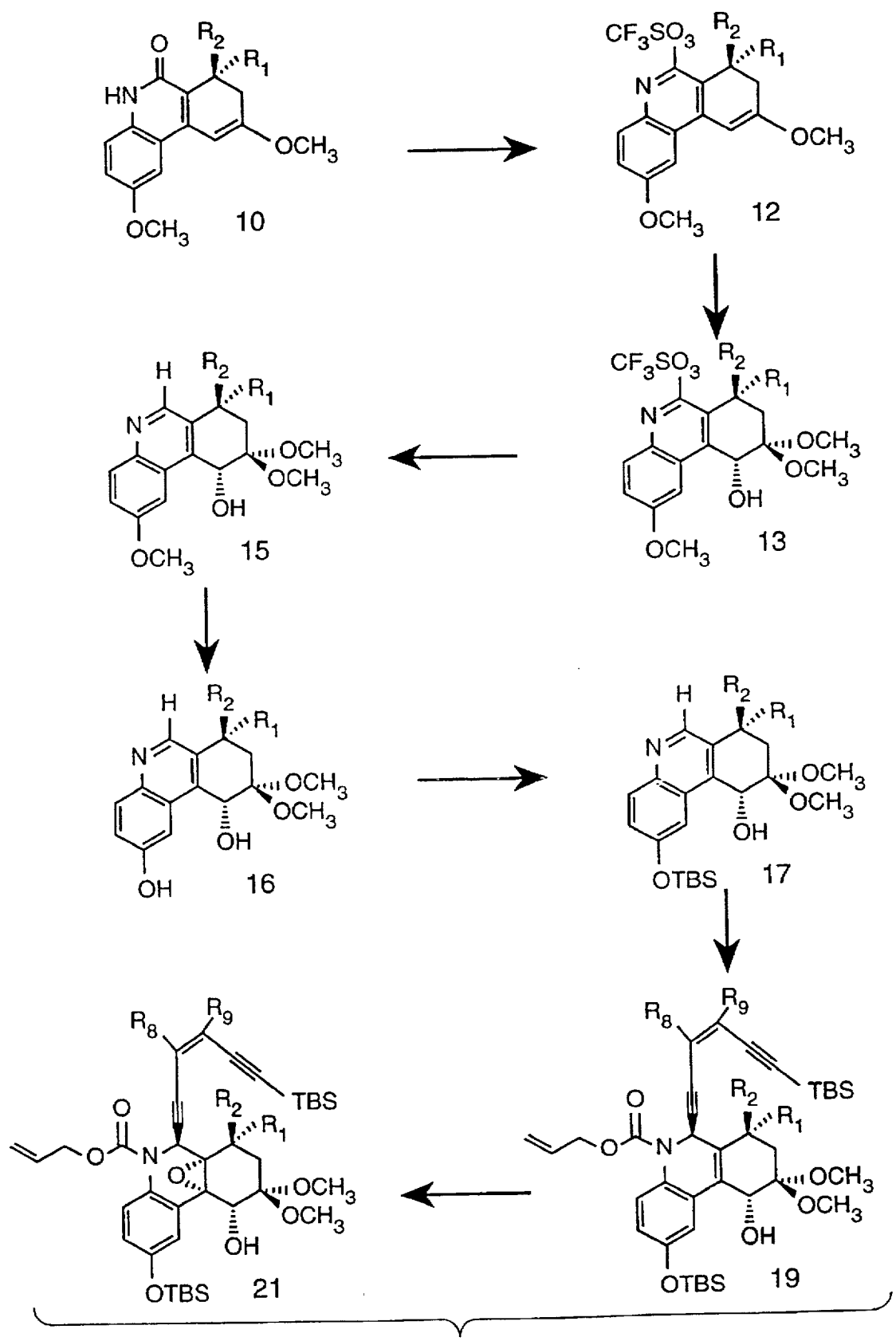
FIG._1B

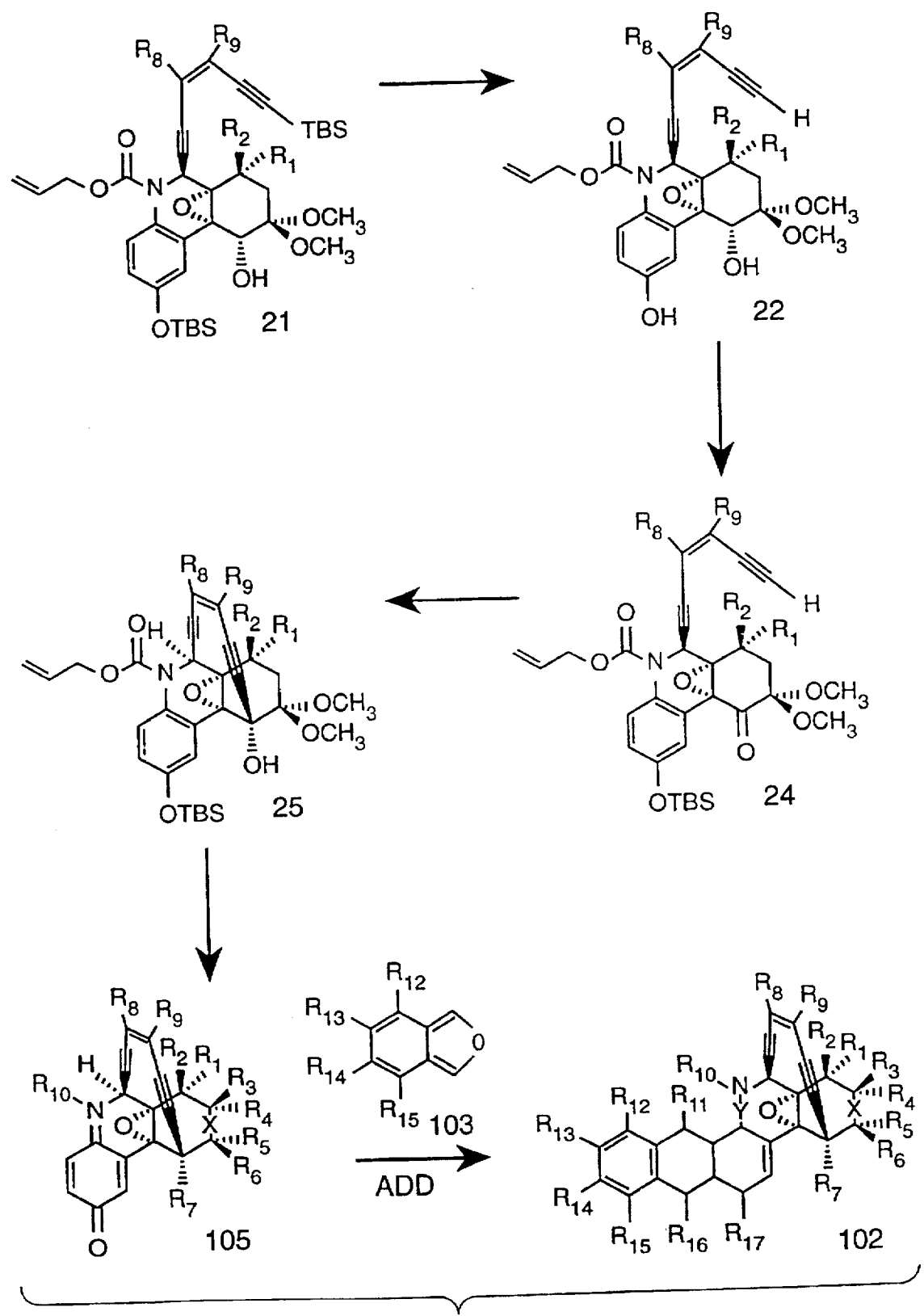
FIG._1C

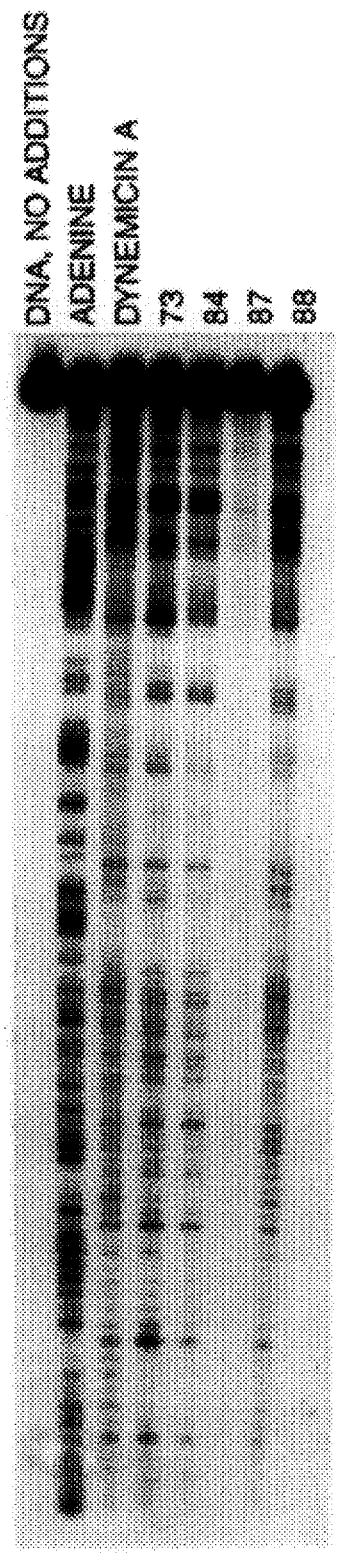
FIG._2

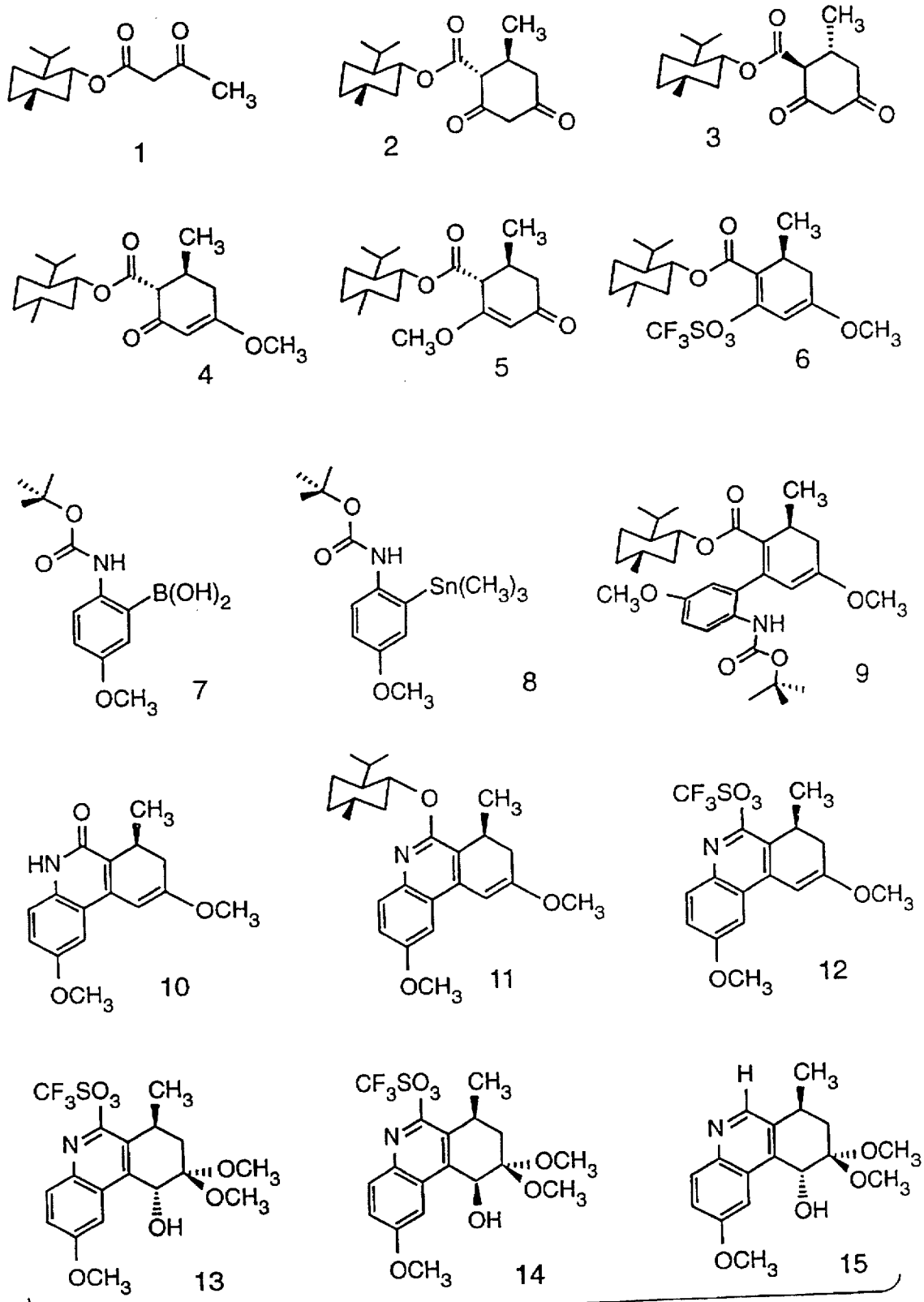
FIG._3A

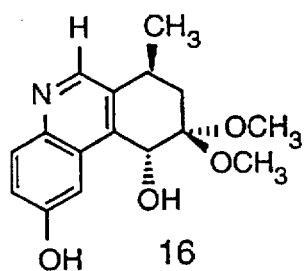
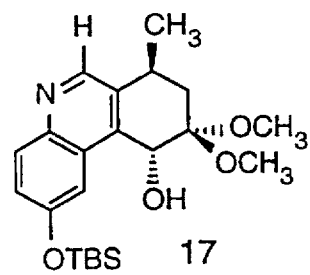
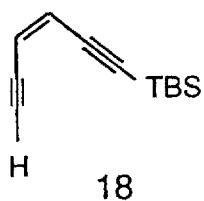
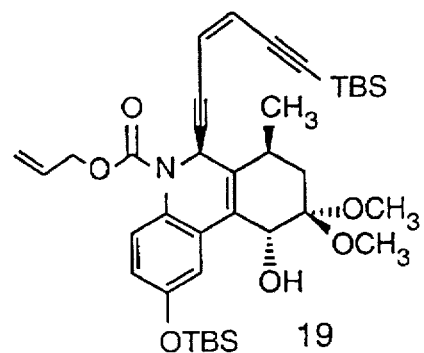
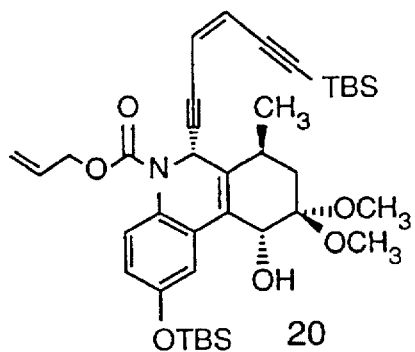
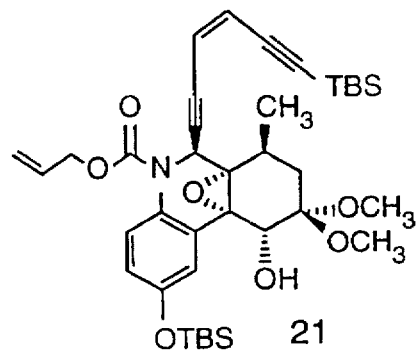
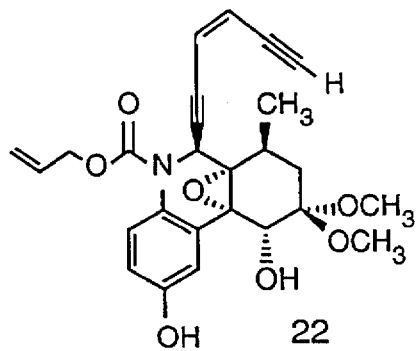
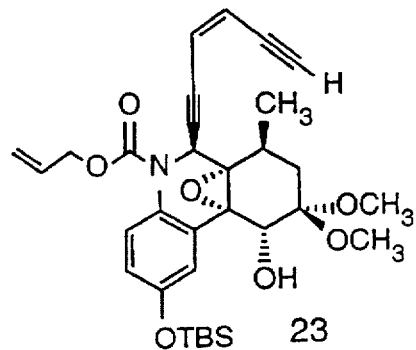
*FIG._3B-1*

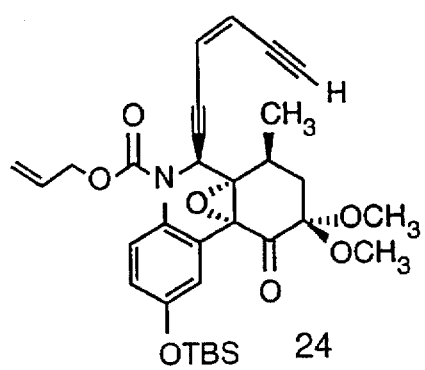
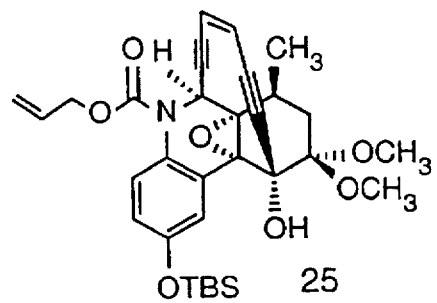
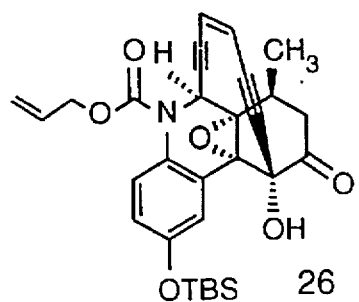
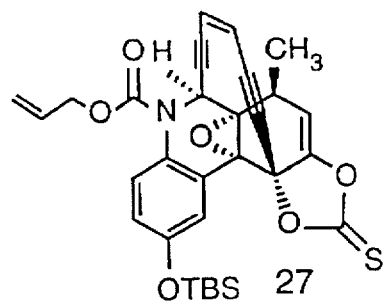
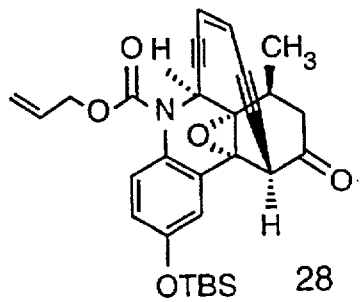
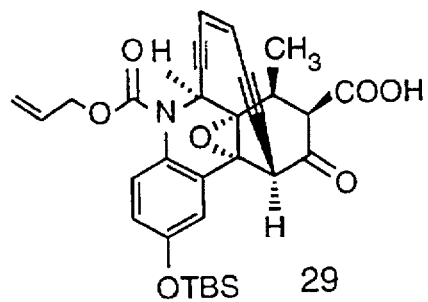
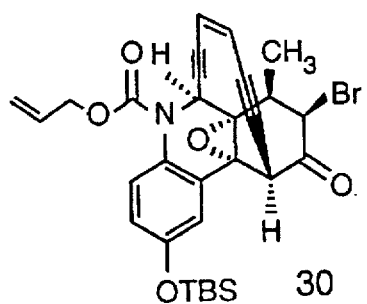
FIG._3B-2

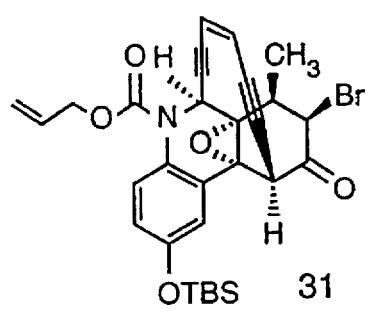
31
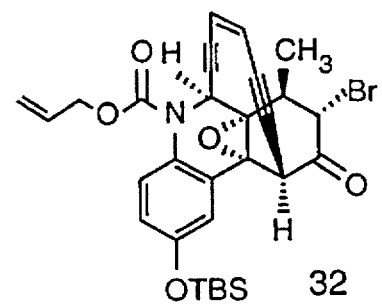
32
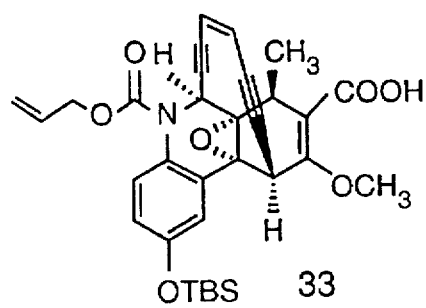
33
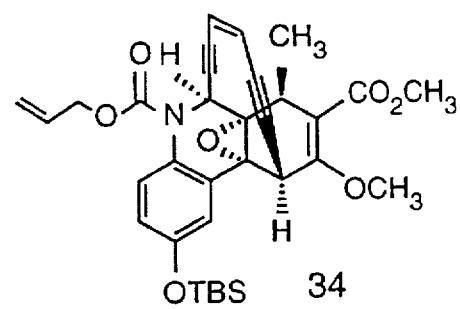
34
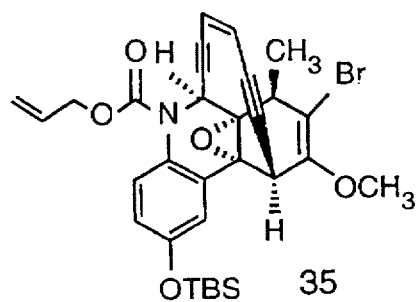
35
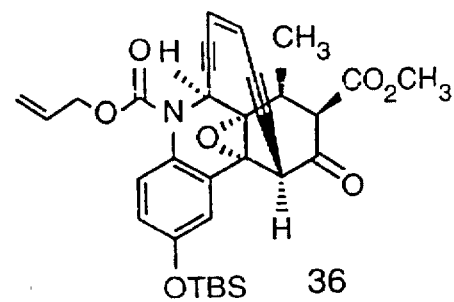
36
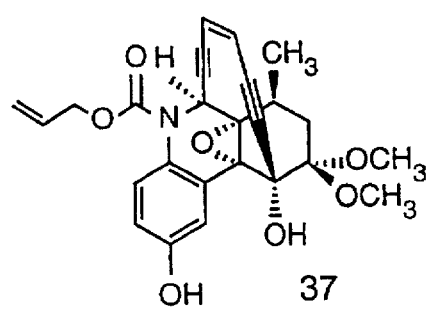
37
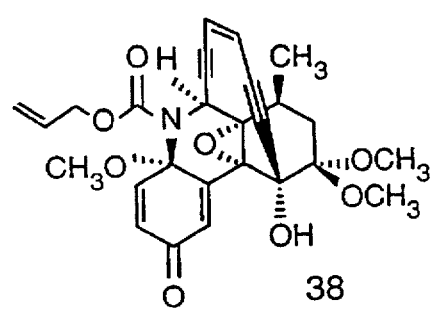
38
*FIG._3C-1*

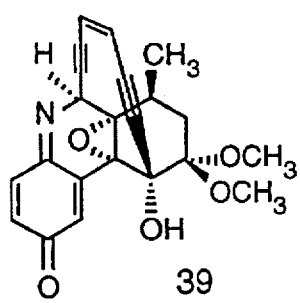 39
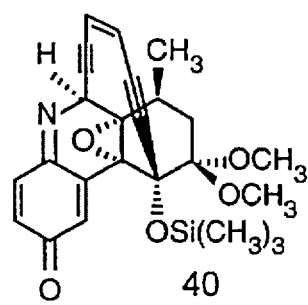 40
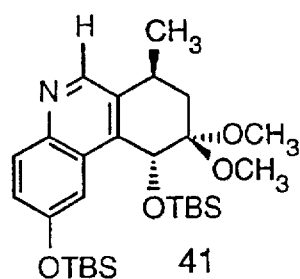 41
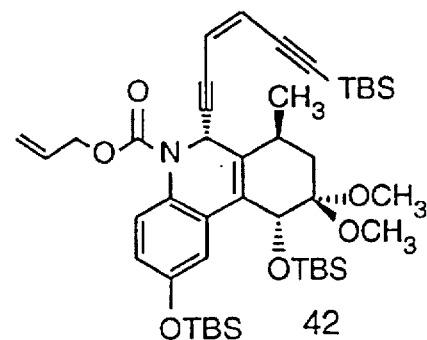 42
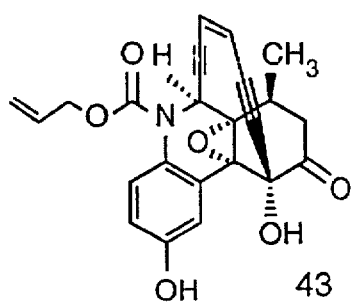 43
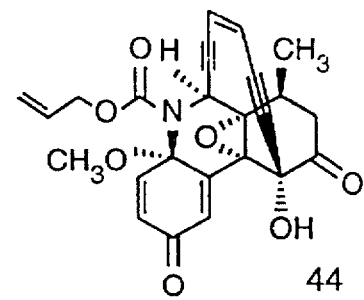 44
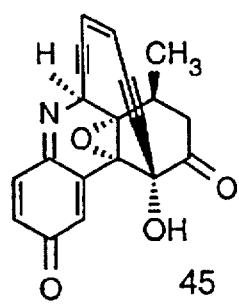 45
*FIG._3C-2*

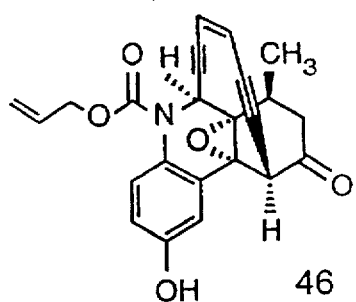
46
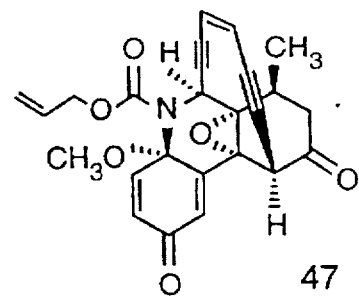
47
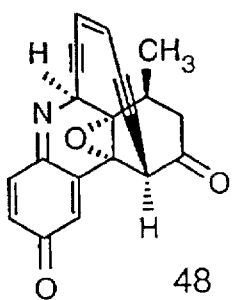
48
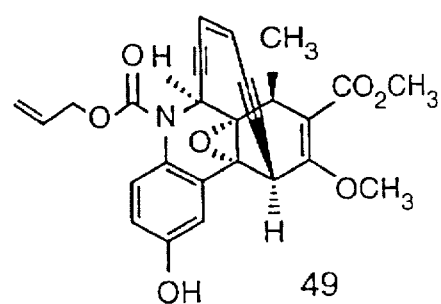
49
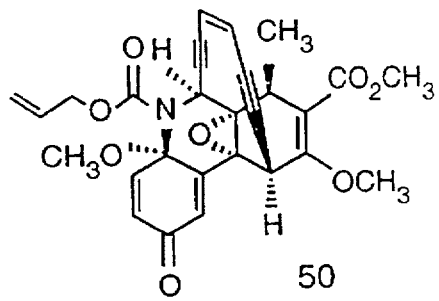
50
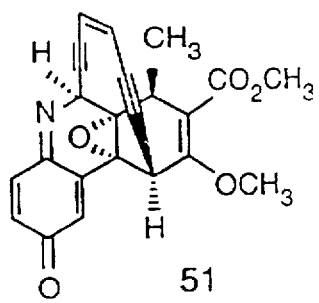
51
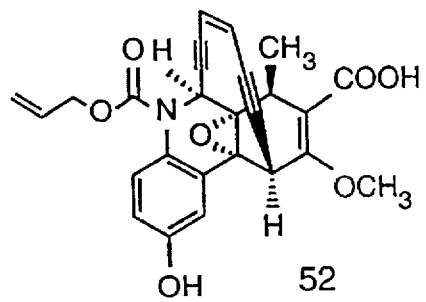
52
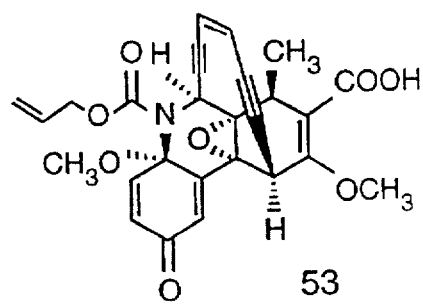
53
*FIG._3D-1*

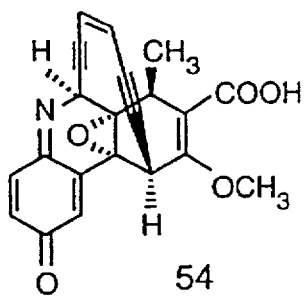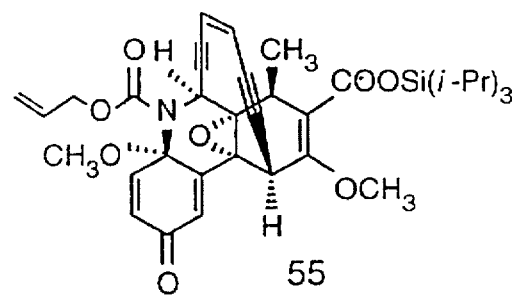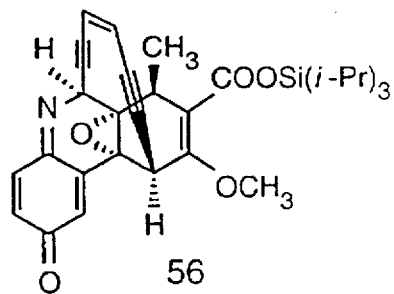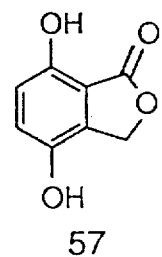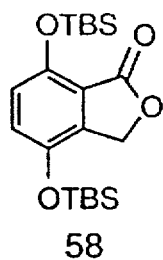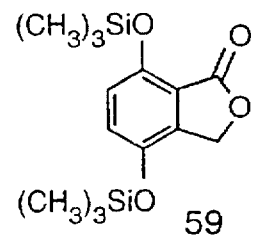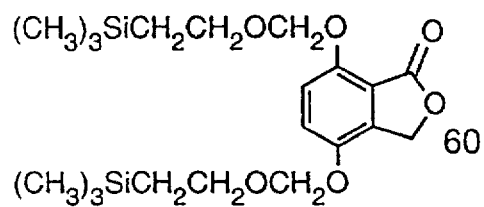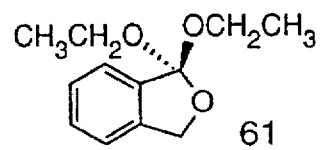
*FIG._3D-2*

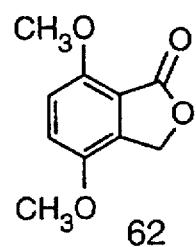 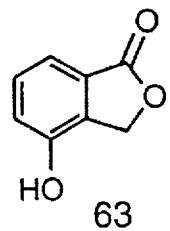
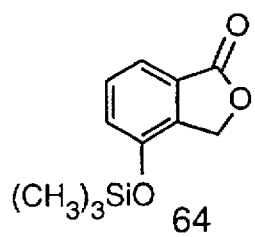 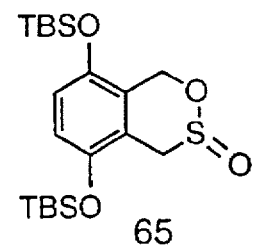
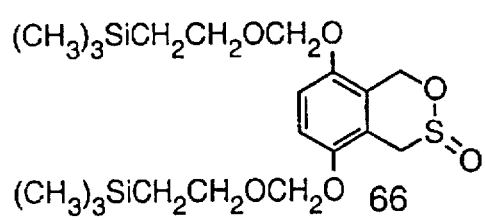 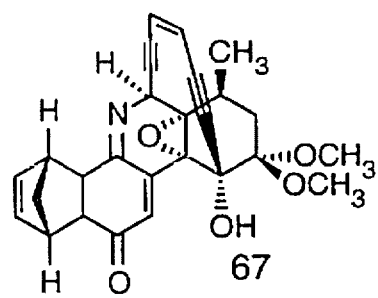
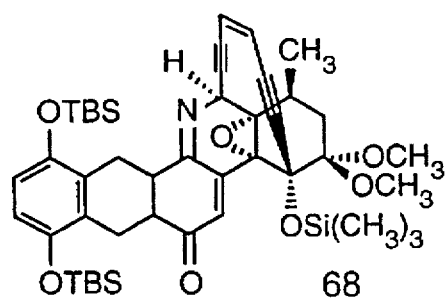 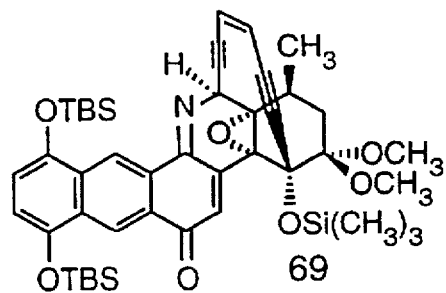
FIG._3E-1

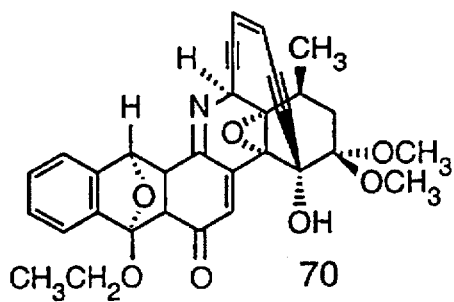
70
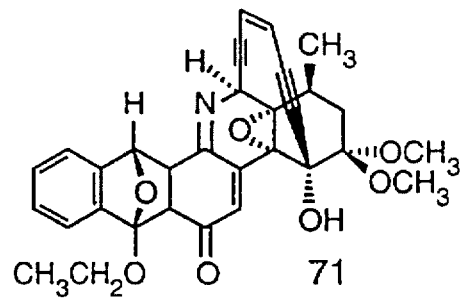
71
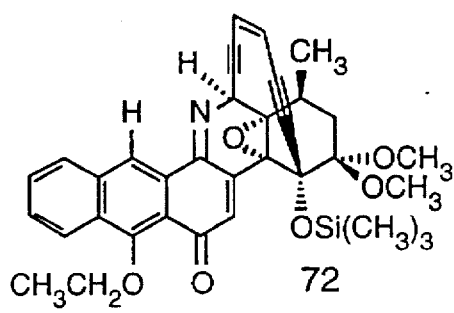
72
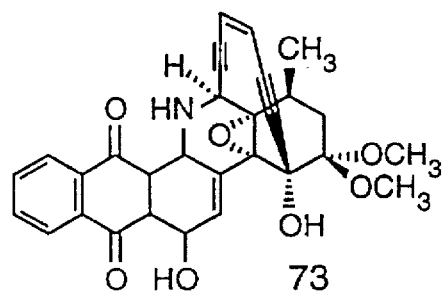
73
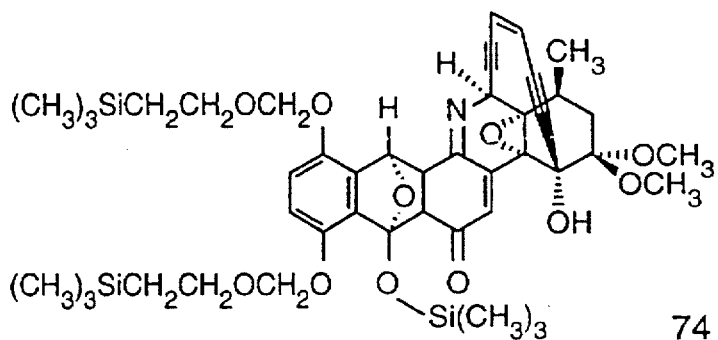
74
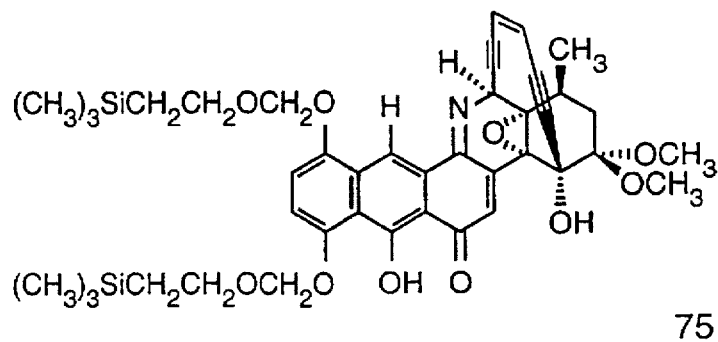
75
*FIG._3E-2*

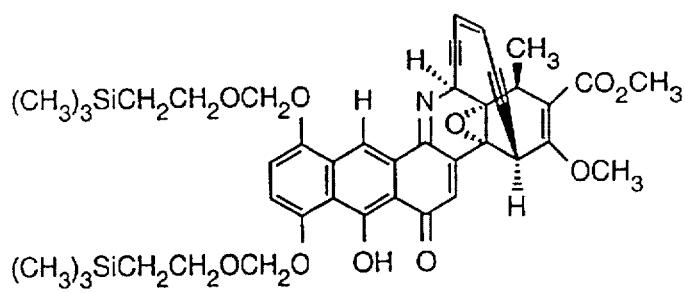
76
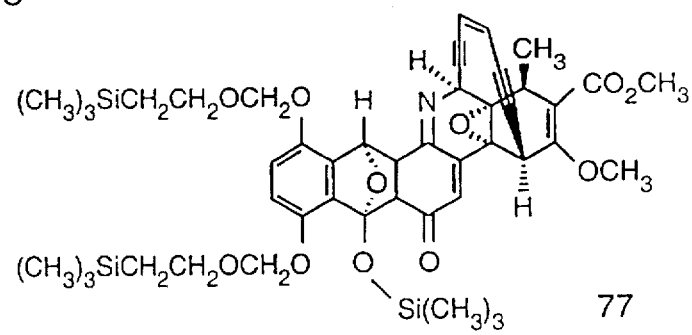
77
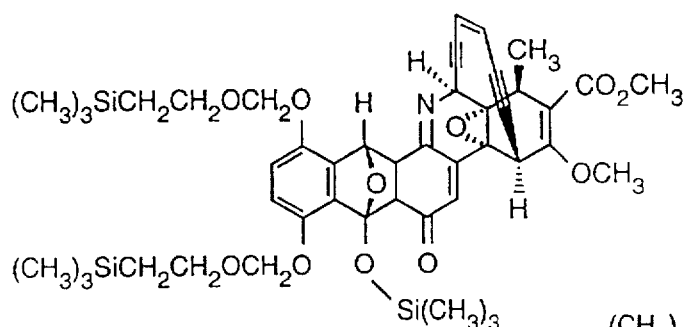
78
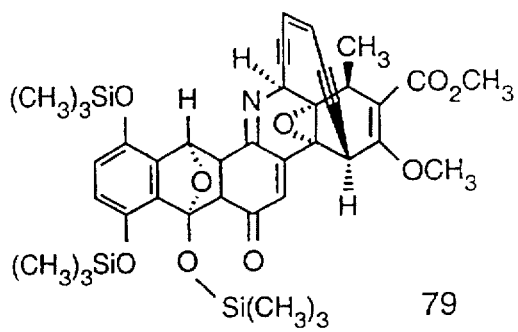
79
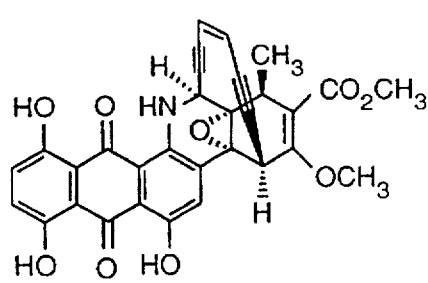
80
FIG._3F-1

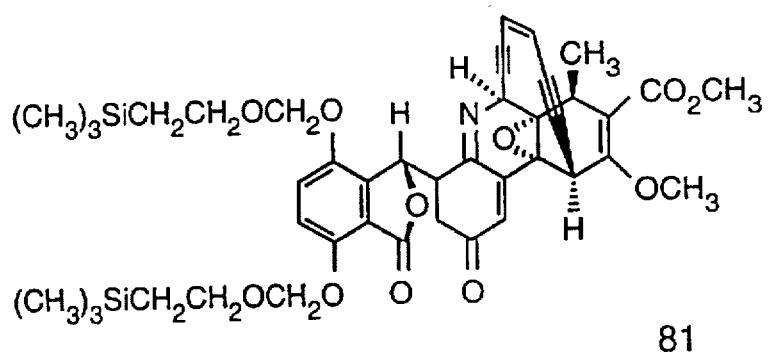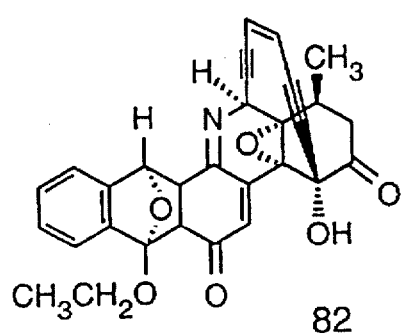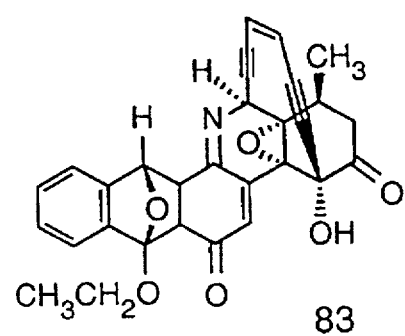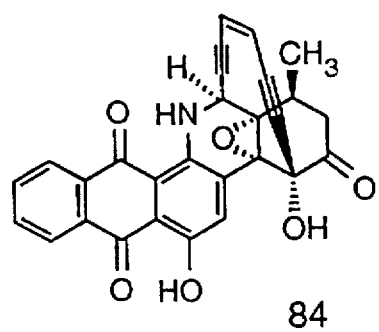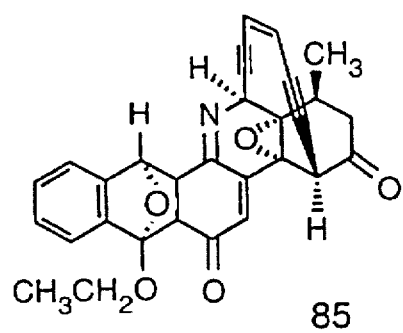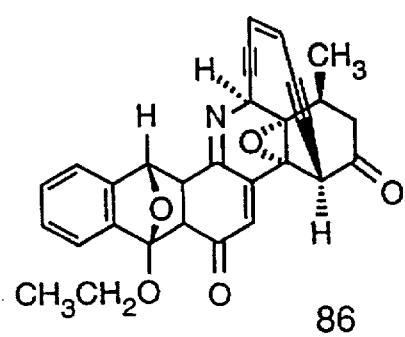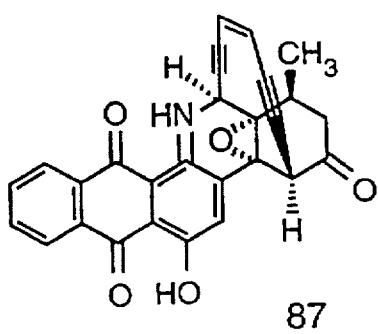
FIG._3F-2

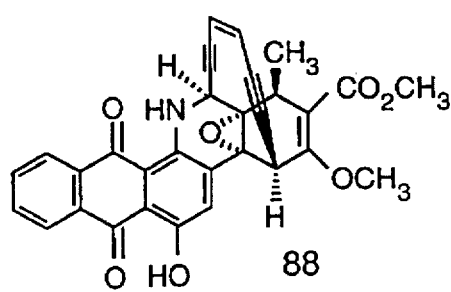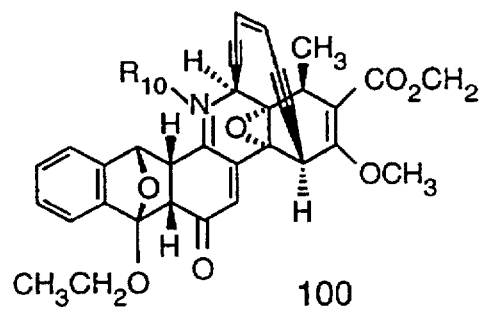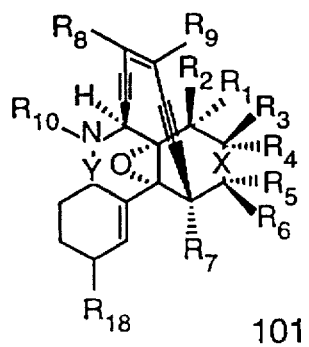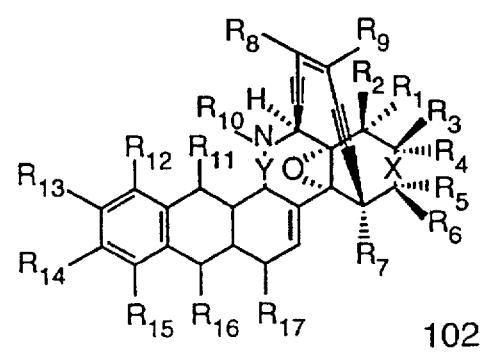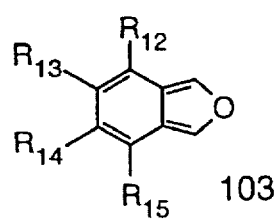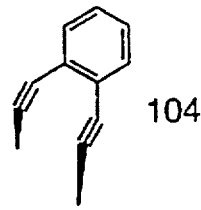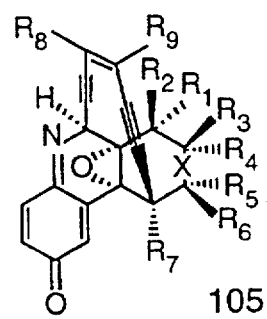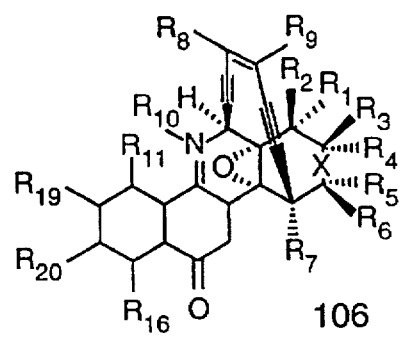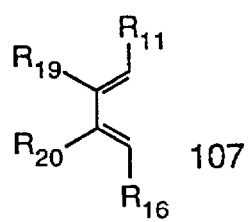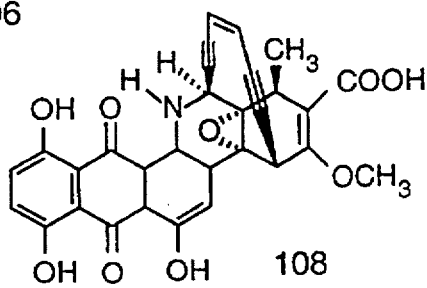
FIG._3G

DYNEMICIN ANALOGS

CROSS-REFERENCE TO RELATED APPLICATIONS

The present application is a continuation-in-part of U.S. patent application Ser. No. 08/281,340, filed Jul. 27, 1994, abandoned.

FIELD OF THE INVENTION

The invention relates to dynemicin analogs and to methods of making such dynemicin analogs.

BACKGROUND OF THE INVENTION

Dynemicin A, shown below, is a potent antibacterial and anticancer agent recently isolated from *Micromonospora chersina* (see U.S. Pat. No. 4,916,065):

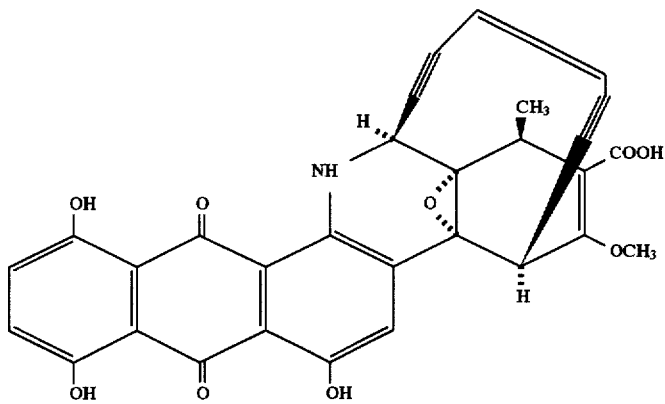

Structure 108

Dynemicin A shares molecular structure similarities with the calicheamicin and esperamicin antibiotic classes, in that it contains an enediyne bridge. Due to its Dynemicin A shares molecular structure similarities with the calicheamicin and esperamicin antibiotic classes, in that it contains an enediyne bridge. Due to its complex structure and sensitive functional groups, its synthesis has proven difficult if not impossible.

For example, portions of the dynemicin molecule have been synthesized (Porco et al., J. Am. Chem. Soc. 1990, 112:7410–7411; Chikashita et al., J. Org. Chem. 1991, 56:1692–1694; Wood et al., J. Am. Chem. Soc. 1992, 114:5898–5900). Di- and tri-O-methyl dynemicin A methyl esters have also reportedly been made (Taunton et al., J. Am. Chem. Soc. 1993, 115:10378–10379).

As a result of this difficulty, several groups have developed synthetic pathways for dynemicin intermediates. For example, U.S. Pat. Nos. 5,276,159 and 5,281,710 describe a variety of dynemicin intermediates. It is far from clear, however, whether any dynemicin analogs containing an anthraquinone structure can be made from the protocols disclosed.

U.S. Pat. No. 5,162,330 describes dynemicin C, obtained by cultivating a mutant strain of *Micromonospora chersina*. A triacetate derivative reportedly was prepared via acetylation.

However, a flexible synthesis has not been developed. Accordingly, it is an object of the present invention to provide novel dynemicin analogs. Such analogs preferably have DNA cleaving, antibiotic and antitumor activities. A further object is to provide methods for the synthesis of such dynemicin analogs.

SUMMARY OF THE INVENTION

In accordance with the foregoing objects, the invention provides novel dynemicin analogs having the formulas depicted below in structures 123, 124, and 125:

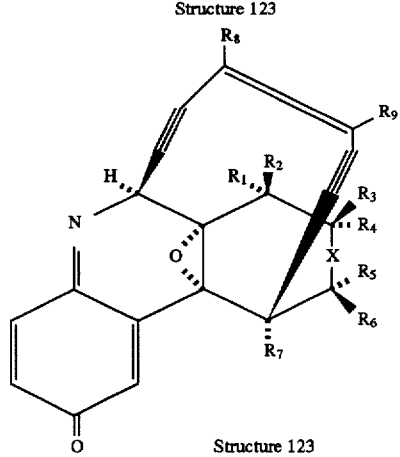

Structure 123

Structure 123 wherein $R_1$ is hydrogen, hydroxy, alkyl, aryl, amine, alkyl amine, alkyl ether, alkoxy, carboxy, carbonyl oxygen, substituted carbonyl, sulfur containing moiety, phosphorus containing moiety, halide, a protecting group;

R2 is hydrogen, hydroxy, alkyl, aryl, amine, alkyl amine, alkyl ether, alkoxy, carboxy, substituted carbonyl, sulfur containing moiety, phosphorus containing moiety, halide, a protecting group, or is absent when R1 is carbonyl oxygen;

R7 is hydrogen, hydroxy, alkyl, aryl, amine, alkyl amine, alkyl ether, alkoxy, carboxy, substituted carbonyl, sulfur containing moiety, phosphorus containing moiety, halide, or a protecting group;

$R_8$ is hydrogen, hydroxy, alkyl, aryl, amine, alkyl amine, alkyl ether, alkoxy, carboxy, substituted carbonyl, sulfur containing moiety, phosphorus containing moiety, halide, a protecting group or with $R_9$ and the unsaturated vinylene between $R_8$ and $R_9$ form an aryl group;

$R_9$ is hydrogen, hydroxy, alkyl, aryl, amine, alkyl amine, alkyl ether, alkoxy, carboxy, substituted carbonyl, sulfur containing moiety, phosphorus containing moiety, halide, a protecting group or with $R_8$ and the unsaturated vinylene between $R_8$ and $R_9$ an aryl group; and X is a double or a single bond;

wherein when X is a single bond, $R_3$ is hydrogen, carbonyl oxygen, hydroxy, alkyl, aryl, alkoxy, carboxy, substituted carbonyl, sulfur containing moiety, phosphorus containing moiety, amine, alkyl amine, alkyl ether, halide or a protecting group;

$R_4$ is hydrogen, hydroxy, alkyl, aryl, alkoxy, carboxy, substituted carbonyl, sulfur containing moiety, phosphorus containing moiety, amine, alkyl amine, alkyl ether, halide, a protecting group, or is absent when $R_3$ is carbonyl oxygen;

$R_5$ is hydrogen, carbonyl oxygen, hydroxy, alkyl, aryl, alkoxy, carboxy, substituted carbonyl, sulfur containing moiety, phosphorus containing moiety, amine, alkyl amine, alkyl ether, halide or a protecting group;

$R_6$ is hydrogen, hydroxy, alkyl, aryl, alkoxy, carboxy, substituted carbonyl, sulfur containing moiety, phosphorus containing moiety, amine, alkyl amine, alkyl ether, halide, a protecting group, or is absent when $R_5$ is carbonyl oxygen;

wherein when X is a double bond, $R_3$ is is absent;

$R_4$ is hydrogen, hydroxy, alkyl, aryl, alkoxy, carboxy, substituted carbonyl, sulfur containing moiety, phosphorus containing moiety, amine, alkyl amine, alkyl ether, halide or a protecting group;

$R_5$ is is absent; and $R_6$ is hydrogen, hydroxy, alkyl, aryl, alkoxy, carboxy, substituted carbonyl, sulfur containing moiety, phosphorus containing moiety, amine, alkyl amine, alkyl ether, halide or a protecting group.

Structure 124

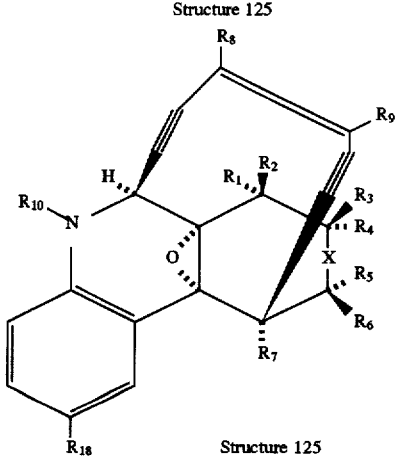

Structure 124 wherein the R groups are as defined above and

R10 is substituted carbonyl; and

R21 is alkoxy.

Structure 125

Structure 125 wherein the R groups are as defined above and

R18 is hydrogen, hydroxy, alkyl, aryl, amine, alkyl amine, alkyl ether, alkoxy, carboxy, substituted carbonyl, sulfur containing moiety, phosphorus containing moiety, halide, or a protecting group.

Also provided are anthraquinone dynemicin analogs such as depicted in structures 1 19, 120 and 121:

Structure 119

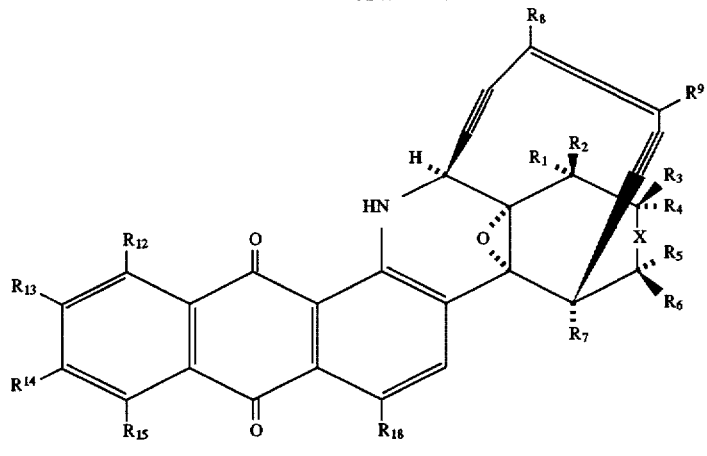

Structure 119 wherein

R₁ is hydrogen, hydroxy, alkyl, aryl, amine, alkyl amine, alkyl ether, alkoxy, carboxy, carbonyl oxygen, substituted carbonyl, sulfur containing moiety, phosphorus containing moiety, halide, or a protecting group;

R2 is hydrogen, hydroxy, alkyl, aryl, amine, alkyl amine, alkyl ether, alkoxy, carboxy, substituted carbonyl, sulfur containing moiety, phosphorus containing moiety, halide, a protecting group, or is absent when R1 is carbonyl oxygen;

R7 is hydrogen, hydroxy, alkyl, aryl, amine, alkyl amine, alkyl ether, alkoxy, carboxy, substituted carbonyl, sulfur containing moiety, phosphorus containing moiety, halide, or a protecting group;

R₈ is hydrogen, hydroxy, alkyl, aryl, amine, alkyl amine, alkyl ether, alkoxy, carboxy, substituted carbonyl, sulfur containing moiety, phosphorus containing moiety, halide, a protecting group or with R₉ and the unsaturated vinylene between R₈ and R₉ form an aryl group;

R₉ is hydrogen, hydroxy, alkyl, aryl, amine, alkyl amine, alkyl ether, alkoxy, carboxy, substituted carbonyl, sulfur containing moiety, phosphorus containing moiety, halide, a protecting group or with R₈ and the unsaturated vinylene between R₈ and R₉ an aryl group;

R12 is hydrogen, hydroxy, alkyl, aryl, amine, alkyl amine, alkyl ether, alkoxy, carboxy, substituted carbonyl, sulfur containing moiety, phosphorus containing moiety, halide, or a protecting group;

R13 is hydrogen, hydroxy, alkyl, aryl, amine, alkyl amine, alkyl ether, alkoxy, carboxy, substituted carbonyl, sulfur containing moiety, phosphorus containing moiety, halide, a protecting group, or together with the unsaturated vinylene group between R13 and R14 from an aryl group;

R14 is hydrogen, hydroxy, alkyl, aryl, amine, alkyl amine, alkyl ether, alkoxy, carboxy, substituted carbonyl, sulfur containing moiety, phosphorus containing moiety, halide, a protecting group, or together with the unsaturated vinylene group between R13 and R14 from an aryl group;

R15 is hydrogen, hydroxy, alkyl, aryl, amine, alkyl amine, alkyl ether, alkoxy, carboxy, substituted carbonyl, sulfur containing moiety, phosphorus containing moiety, halide, or a protecting group;

R18 is hydrogen, hydroxy, alkyl, aryl, amine, alkyl amine, alkyl ether, alkoxy, carboxy, substituted carbonyl, sulfur containing moiety, phosphorus containing moiety, halide, or a protecting group; and X is a double or a single bond;

wherein when X is a single bond,

R₃ is hydrogen, carbonyl oxygen, hydroxy, alkyl, aryl, alkoxy, carboxy, substituted carbonyl, sulfur containing moiety, phosphorus containing moiety, amine, alkyl amine, alkyl ether, halide or a protecting group;

R₄ is hydrogen, hydroxy, alkyl, aryl, alkoxy, carboxy, substituted carbonyl, sulfur containing moiety, phosphorus containing moiety, amine, alkyl amine, alkyl ether, halide, a protecting group, or is absent when R₃ is carbonyl oxygen;

R₅ is hydrogen, carbonyl oxygen, hydroxy, alkyl, aryl, alkoxy, carboxy, substituted carbonyl, sulfur containing moiety, phosphorus containing moiety, amine, alkyl amine, alkyl ether, halide or a protecting group;

R₆ is hydrogen, hydroxy, alkyl, aryl, alkoxy, carboxy, substituted carbonyl, sulfur containing moiety, phosphorus containing moiety, amine, alkyl amine, alkyl ether, halide, a protecting group, or is absent when R₅ is carbonyl oxygen;

wherein when X is a double bond,

R₃ is absent;

R₄ is hydrogen, hydroxy, alkyl, aryl, alkoxy, carboxy, substituted carbonyl, sulfur containing moiety, phosphorus containing moiety, amine, alkyl amine, alkyl ether, halide or a protecting group;

R₅ is absent; and

R₆ is hydrogen, hydroxy, alkyl, aryl, alkoxy, carboxy, substituted carbonyl, sulfur containing moiety, phosphorus containing moiety, amine, alkyl amine, alkyl ether, halide or a protecting group.

Structure 120:

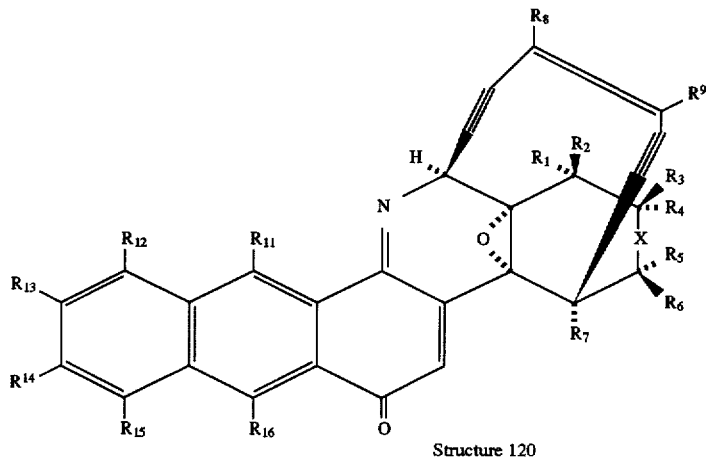

Structure 120 wherein the R1 to R9 groups are defined as above and
R11 is hydrogen, hydroxy, alkyl, alkyl ether, or a protecting group; and
R16 is hydrogen, hydroxy, alkyl, alkyl ether, or a protecting group.

Structure 121:

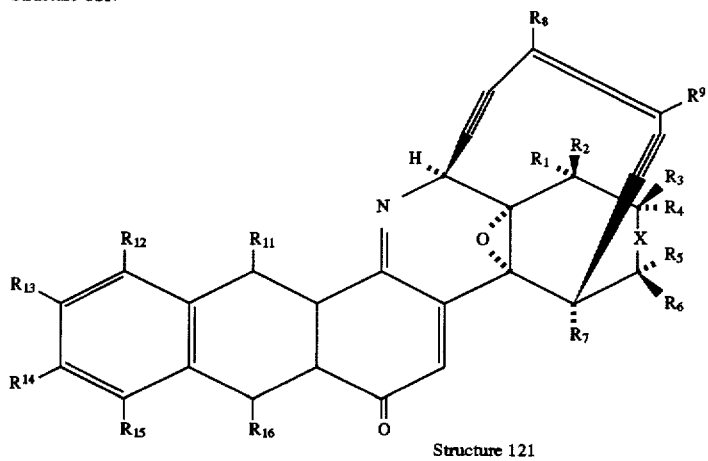

Structure 121 wherein the $R_1$ to $R_{16}$ groups are defined as above.

A further aspect provides methods of making dynemicin analogs comprising reacting dienes with quinone imines.

An additional aspect provides methods of inhibiting the growth of cells, and pharmaceutical compositions comprising the dynemicin analogs of the present invention.

BRIEF DESCRIPTION OF THE DRAWINGS

FIGS. 1A, 1B and 1C depict the general synthetic scheme for the quinone imine dynemicin analog precursor (structure 25), the quinone imine dynemicin analog (structure 101) and the anthraquinone dynemicin analog (structure 102).

FIG. 2 depicts the results of the DNA cleavage experiments of Example 4.

FIGS. 3A, 3B, 3C, 3D, 3E, 3F, and 3G depict some of the structures of the present invention.

DETAILED DESCRIPTION OF THE INVENTION

The invention provides novel dynemicin analogs. A dynemicin analog is defined generally as having one of several structures. The dynemicin analog may be a five membered ring, such as generally depicted in structures 123, 124 or 125, or a seven membered ring, such as generally depicted in structures 119, 120 and 121.

The five membered ring structures include three 6 membered rings, an epoxide ring, and a ring formed by the enediyne bridge. These dynemicin analogs include the quinone imine structures generally depicted in structure 123, as well as the analogs depicted generally in structure 124 and 125. As is appreciated by those in the art, these general structures include the embodiments depicted in structures 110, 111, 112, 113, 114, 115:

Structure 110:

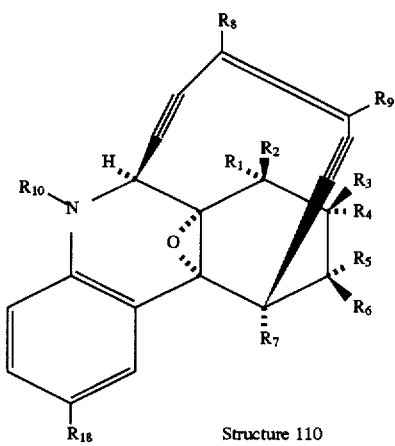

Structure 110

Structure 111:

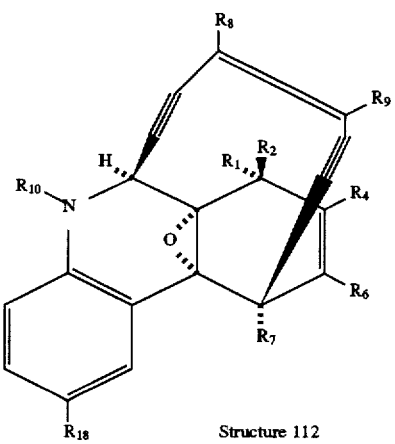

Structure 111

Structure 112:

Structure 112

Structure 113:

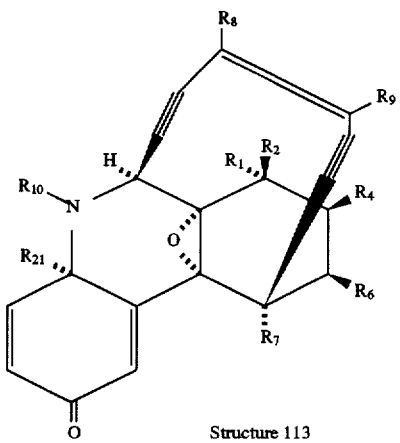

Structure 113

Structure 114:

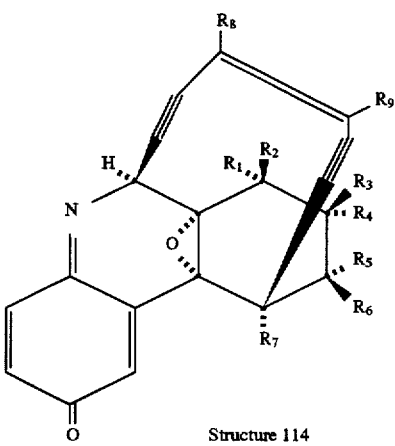

Structure 114

Structure 115:

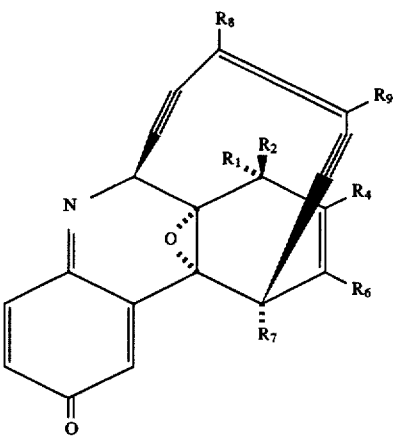

The seven membered ring analogs include include five 6 membered rings, an epoxide ring, and a ring formed by the enediyne bridge. These dynemicin analogs include the anthraquinone analogs structures generally depicted in structure 119, as well as the analogs depicted generally in structure 120 and 121. As is appreciated by those in the art, these general structures include the embodiments depicted in structures 126, 127, 128, 129, 130, and 131:

Structure 126:
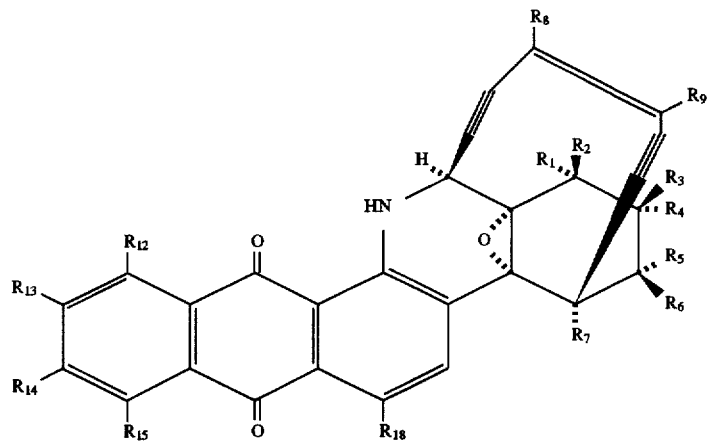
Structure 126
Structure 127:
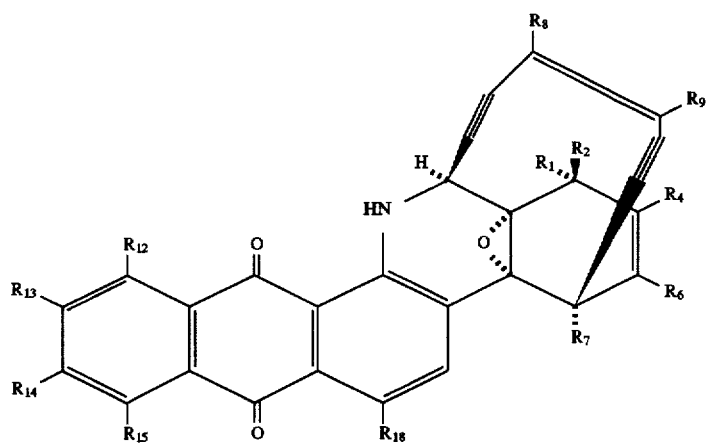
Structure 127
Structure 128:
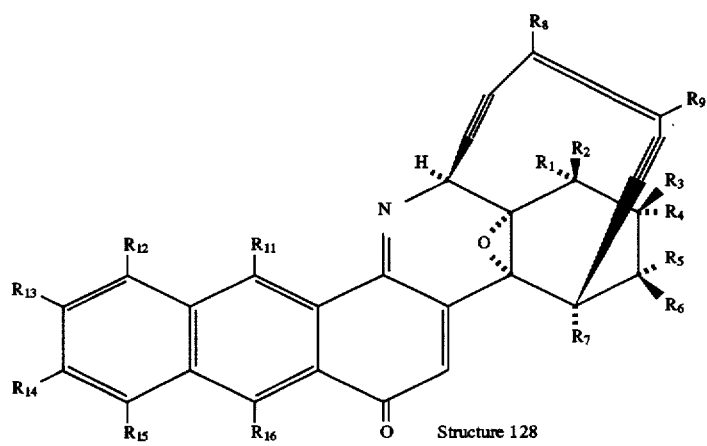
Structure 128

Structure 129:

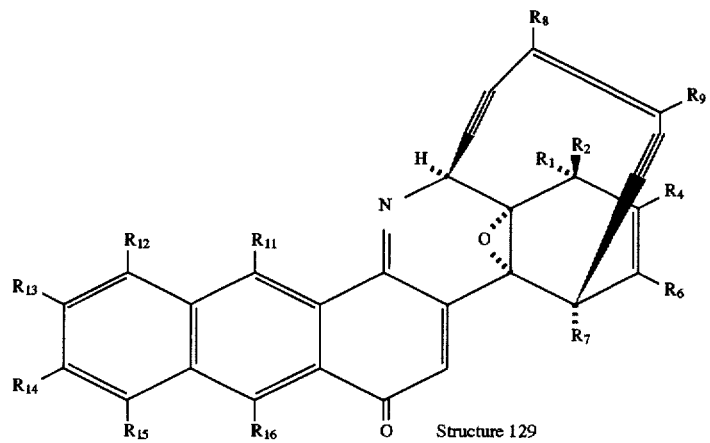

Structure 129

Structure 130:

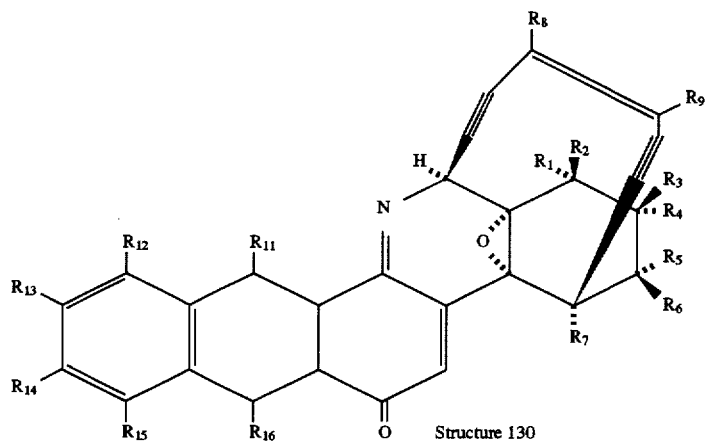

Structure 130

Structure 131:

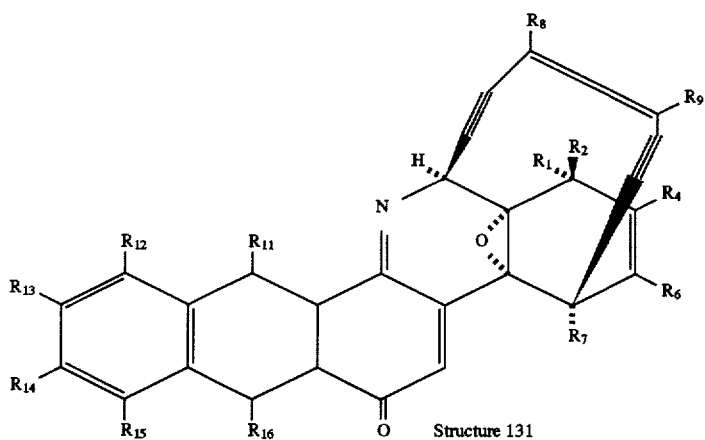

Structure 131

Thus, the definition of a dynemicin analog includes both five membered ring and seven membered ring dynemicin analogs, including the quinone imine and anthraquinone analogs. Generally speaking, the dynemicin analogs have one or more important functionalities, including the enediyne bridge, the epoxide moiety, and the anthraquinone-like ring structure. However, dynemicin analogs may be made which lack one or more of the functionalities or have additional structural components. For example, quinone imine dynemicin analogs which lack the complete anthraquinone structure can be made.

The dynemicin analogs of the invention are not naturally occurring; that is, they do not have the structure outlined in Structure 108. However, the dynemicin analog may differ in only one position from the naturally-occuring dynemicin A, or it may differ in a variety of positions. For example, a dynemicin analog may have a methyl ester at position $R_4$, with the remaining R groups identical to structure 108. In one embodiment, as outlined below, the dynemicin analog may have the structure of naturally occuring dynemicin A but is radiolabelled, and thus is not naturally occuring. Alternatively, a dynemicin analog has an R group in the opposite stereo-orientation from naturally occurring dynemicin A. For example, in structure 102, $R_1$ may be a methyl group and $R_2$ a hydrogen, with all other R groups being the same as the naturally occuring product. Alternatively, all of the R groups can be identical to the naturally occuring dynemicin A, except that the enediyne bridge may be on the opposite side of the molecule.

In a preferred embodiment, the dynemicin analogs are not triacetate derivatives such as is described in U.S. Pat. No. 4,916,065. That is, when the analog has the structure depicted in structure 119, the $R_{12}$, $R_{15}$ and $R_{18}$ groups are not all hydroxy (representing the naturally occurring dynemicin) nor acetate (—OOCCH$_3$), when $R_1$, $R_7$, $R_8$, and $R_9$ are hydrogen, $R_2$ is methyl, X is a double bond, R4 is COOH, and $R_6$ is methoxy. Similarly, in a preferred embodiment the dynemicin analogs are not di- or tri-O-methyl derivatives such as described in Taunton et al., J. Am. Chem. Soc. 115:10378–10379 (1993). That is, in structure 119, the $R_{12}$, $R_{15}$ and $R_{18}$ groups are not all methoxy, or $R_{12}$ and $R_{18}$ are not methoxy, when $R_1$, $R_7$, $R_8$, and $R_9$ are hydrogen, $R_2$ is methyl, X is a double bond, R4 is COOH, and $R_6$ is methoxy.

At the broadest level, the selection of the $R_1$ and $R_2$ groups may be limited by steric considerations at this position. Generally, $R_1$ is hydrogen, hydroxy, alkyl, aryl, amine, alkyl amine, alkyl ether, alkoxy, carboxy, carbonyl oxygen, substituted carbonyl, sulfur containing moiety, phosphorus containing moiety, halide, or a protecting group. In a preferred embodiment, $R_1$ is a hydrogen or methyl group, with hydrogen being preferred.

Similarly, $R_2$ is hydrogen, hydroxy, alkyl, aryl, amine, alkyl amine, alkyl ether, alkoxy, carboxy, substituted carbonyl, sulfur containing moiety, phosphorus containing moiety, halide, or a protecting group. As will be appreciated, only one of $R_1$ or $R_2$ can be carbonyl oxygen, and it can be either. For simplicity, $R_1$ is depicted as including carbonyl oxygen. When $R_1$ is carbonyl oxygen, $R_2$ is absent. In a preferred embodiment, $R_2$ is a straight chain alkyl. In the preferred embodiment, $R_2$ is a methyl group.

By "alkyl group" or grammatical equivalents herein is meant a straight or branched chain alkyl group. If branched, it may be branched at one or more positions, and unless specified, at any position. The alkyl group may range from about 1 to 20 carbon atoms (C1–C20), with a preferred embodiment utilizing from about 1 through 16 carbon atoms (C1–C16), with about C1 through about C5 preferred. However, in some embodiments, the alkyl group may be larger, particularly if it is a straight-chain alkyl. Alkyl includes unsaturated hydrocarbons, including alkenyl and alkynyl.

Also included within the definition of an alkyl group are cycloalkyl groups such as C5 and C6 rings. In some cases, two R groups may be part of a ring structure, that is, they may be linked to form a cyclic structure, including heterocyclic structures. In some cases, the R groups may form an aryl group.

By "aryl" or "aryl group" herein is meant aromatic rings including phenyl, benzyl, and naphthyl, heterocyclic aromatic rings including pyridine, furan, thiophene, pyrrole, indole and purine, and heterocyclic rings with nitrogen, oxygen, sulfur or phosphorus.

The alkyl and aryl groups may be substituted, for example, a phenyl group may be a substituted phenyl group. Suitable substitution groups include, but are not limited to, alkyl and aryl groups, halogens such as chlorine, bromine and fluorine, amines, carboxylic acids, nitro and thiol groups.

By the term "amine" herein is meant an —NRR' group. In this embodiment, R and R' may be the same or different, and may be hydrogen, alkyl or aryl. A preferred amine group is —NH$_2$.

By the term "alkyl amine" herein is meant an alkyl group with an amine group as defined above at any position.

By "hydroxy" herein is meant a —OH group.

By "carboxy" herein is meant a —COOH or —COOR group, wherein R is alkyl or aryl.

By "substituted carbonyl" herein is meant a —COR group, where R may be hydrogen, alkyl, aryl, amine, alkyl amine, ether or thiol ether (that is, the substituted carbonyl is an ester or thiol ester). As outlined below, with particular reference to the $R_{10}$ group of the five membered ring dynemicin analogs, preferred substituted carbonyls are —COR and —COOR.

By "alkoxy" herein is meant an —OR group, where R is an alkyl or aryl group as depicted above. Preferred alkoxy is methoxy (—OCH$_3$).

By "phosphorus containing moiety" herein is meant a functional group containing at least one phosphorus atom. In a preferred embodiment, the phosphorus-containing moiety is a phosphate (—OPO(OH)$_2$ group), pyrophosphates, or a substituted phosphate group of the formula —OPO(OR)(OR'), wherein R and R' are independently selected from alkyl or aryl. Also included within the definition of phosphorus containing moieties are phosphines (—R$_3$P), and phosphonates (—RPO(OR)(OR')).

By "sulfur containing moiety" herein is meant a functional group containing at least one sulfur atom. Thus thiols (—RSH), sulfides (RSR'), sulfoxides (—SO—), sulfones (—SO$_2$—), sulfates (—OSO$_2$O—), and sulfonic acids (—RSO$_2$OH) are all included within the definition of sulfur containing moieties.

By "halide" herein is meant a halide atom. Preferred halides include chlorine, fluorine, bromine and iodine.

By "protecting group" herein is meant a group used to protect a heteroatom such as oxygen, nitrogen, sulfur or phosphorus from subsequent chemical alteration. In a preferred embodiment, the protecting group is used to protect an oxygen heteroatom such as a hydroxy group. Protecting groups are well known in the art, see for example Greene, T. W. *Protective Groups in Organic Synthesis*, John Wiley and Sons, Inc: New York. 1991. Preferred protecting groups include, but are not limited to, the "boc" protecting group, trialkyl silyl groups such as TBS (tert-butyldimethylsilyl, Si(CH$_3$)$_2$C(CH$_3$)$_3$), MEM, MOM, SEM, and THP, as are known in the art.

With specific regard to the $R_{10}$ group, it should be understood that the substituted carbonyl group is acting functionally as a protecting group. Thus, preferred $R_{10}$ groups are acyl groups such as Alloc, a known carbamate.

By "protected alkyl alcohol" herein is meant an alkyl chain with the alcohol oxygen linked to a protecting group, of the general formula $C_n$—O-protecting group, wherein n has the same requirements as the alkyl group. Similarly, a "protected alkyl thiol" has the general formula $C_n$—S-protecting group, and utilizes the same protecting groups as above.

By an "alkyl ether" herein is meant a group of the general formula $C_{n1}$—O—$C_{n2}$. Generally, n1+n2 falls within the range for desirable alkyl group lengths. In a preferred embodiment, n1 is zero; that is, the oxygen atom is the first atom directly attached at a given "R" position. In one embodiment, an alkyl ether may have more than one ether moiety; that is, it may have two or more oxygen atoms, linked via carbon-ether linkages.

By a "alkyl silyl ether" herein is meant a group of the general formula $C_{n1}$—O—$C_{n2}$—Si—$C_{n3}$. As for the alkyl ethers, n1+n2+n3 falls within the range for desirable alkyl group lengths. In a preferred embodiment, both n1 and n2 are zero; that is, the oxygen atom is the first atom and the silicon atom is attached to the oxygen atom as the second atom attached at a given "R" position. For example, —O—Si—$(C_n)_{n1}$ is a preferred alkyl silyl ether, and when n1 is three, it is a trialkyl silyl ether. In one embodiment, an alkyl silyl ether may have more than one ether moiety; that is, it may have two or more oxygen atoms, linked via carbon-ether linkages.

Generally, the steric considerations of the $R_1$ or $R_2$ group on the same side of the molecule as the enediyne bridge are greater than the steric constraints on other R group. That is, in most of the structures depicted herein, the steric constraints on $R_2$ are greater; thus, straight chain alkyl is preferred over branched chains. However, as outlined below, it is possible to make the enediyne bridge attach on the other side; in this case, the requirements of $R_1$ and $R_2$ would be reversed.

The selection of $R_7$ groups is limited only by the generation of the appropriate reaction in the synthesis reaction, outlined below. Thus, $R_7$ may be a hydrogen, a hydroxyl group, alkyl, aryl, amine, alkyl amine, alkyl ether, alkoxy, carboxy, substituted carbonyl, sulfur containing moiety, phosphorus containing moiety, halide, a protecting group, or, when X is a double bond and $R_6$ is an oxygen, forms a cyclic thiocarbonate, as shown in Structure 27. Preferred embodiments utilize hydroxyl and hydrogen groups, with hydrogen being particularly preferred.

In a further embodiment, when the enediyne bridge is on the opposite side of the molecule than is shown in Structures 101, 102, or 105, $R_7$ will also be in the opposite orientation.

The $R_8$ and $R_9$ groups may be identical, or different. In the broadest embodiment, the structure of $R_8$ and $R_9$ are limited only by the generation of the appropriate reagent in the synthesis reaction, outlined below. Thus $R_8$ and $R_9$ are limited by the ability to generate the corresponding structure 18.

Generally, $R_8$ and $R_9$ are each selected from the group consisting of hydrogen, alkyl, hydroxy, aryl, amine, alkyl amine, alkyl ether, alkoxy, carboxy, substituted carbonyl, sulfur containing moiety, phosphorus containing moiety, halide, a protecting group, or $R_8$ and $R_9$, together with the unsaturated vinylene group form an aryl group. In a preferred embodiment, both $R_8$ and $R_9$ are hydrogen.

In one embodiment, $R_8$ and $R_9$, together with the unsaturated vinylene group, form an aryl group. Thus, for example, structure 104, shown below, may be made:

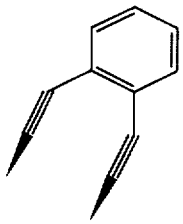

Structure 104

In one embodiment, a targeting group may also be attached to $R_8$ or $R_9$, or both. Generally, the targeting group will be linked via a spacer, for example, a straight chain C1–C10 alkyl group or a peptidyl spacer such as $(Ala)_n$ that links the dynemicin analog to a targeting group. By "targeting group" herein is meant a group which allows the dynemicin analog to be targeted to a specific site or cell type within a patient. For example, the targeting group may be an antibody, such as a monoclonal antibody (MAb), which binds to specific cell types, for example, tumor cells. Anti-tumor Mabs are known in the art; for example, see U.S. Pat. No. 5,276,159. Alternatively, the targeting group may be a receptor ligand, such as a cell surface receptor ligand, which will target the dynemicin analog to the receptor. These ligands include, but are not limited to, proteins, oligosaccharides, hormones, or cytokines.

In an additional embodiment, the targeting group may be attached via the carboxyl group of dynemicin A, or via an alternative ester at position $R_3$.

The methods used for attaching the targeting groups are known in the art. For example, when the targeting group is an oligosaccharide, the position of the glycosyl bond to be formed in the sugar moiety used for forming a chimeric compound is typically activated prior to linkage to the dynemicin analog, as outlined in U.S. Pat. No. 5,276,159. MAbs may be attached via the episilon amino of lysine or in a disulfide linkage with a cysteine residue.

X is either a double or single bond.

The choice of groups $R_3$, $R_4$, $R_5$ and $R_6$ depend on whether the X bond is a single or a double bond.

In a preferred embodiment, the X bond is a single bond.

In this embodiment, $R_3$ may be hydrogen, carbonyl oxygen, hydroxy, alkyl, aryl, alkoxy, carboxy, substituted carbonyl, sulfur containing moiety, phosphorus containing moiety, amine, alkyl amine, alkyl ether, halide or protecting group. When $R_3$ is carbonyl oxygen, it is double bonded to the ring, thus forming a ketone, and $R_4$ is absent. When $R_3$ is a halogen, Br is preferred.

When the X bond is a single bond, $R_4$ may be hydrogen, hydroxy, alkyl, aryl, alkoxy, carboxy, substituted carbonyl, sulfur containing moiety, phosphorus containing moiety, amine, alkyl amine, alkyl ether, halide, a protecting group or is absent when $R_3$ is carbonyl oxygen. Hydroxy is preferred.

In a preferred embodiment, $R_3$ and $R_4$ are both hydrogens.

When the X bond is a single bond, $R_5$ may be hydrogen, carbonyl oxygen, hydroxy, alkyl, aryl, alkoxy, carboxy, substituted carbonyl, sulfur containing moiety, phosphorus containing moiety, amine, alkyl amine, alkyl ether, halide or protecting group. When $R_5$ is carbonyl oxygen, it is double bonded to the ring, and $R_6$ is absent.

When the X bond is a single bond, $R_6$ may be hydrogen, hydroxy, alkyl, aryl, alkoxy, carboxy, substituted carbonyl, sulfur containing moiety, phosphorus containing moiety, amine, alkyl amine, alkyl ether, halide, a protecting group or is absent when $R_5$ is a carbonyl oxygen double bonded to the ring.

In a preferred embodiment, both $R_5$ and $R_6$ are methyoxy groups.

In an additional embodiment, the X bond is a double bond.

In this embodiment, $R_3$ and $R_5$ are absent. $R_4$ may be a hydrogen, hydroxy, alkyl, aryl, alkoxy, carboxy, substituted carbonyl, sulfur containing moiety, phosphorus containing moiety, amine, alkyl amine, alkyl ether, halide or protecting group. Particularly preferred is the methyl ester.

When the X bond is a double bond, $R_6$ may also be a hydrogen, hydroxy, alkyl, aryl, alkoxy, carboxy, substituted carbonyl, sulfur containing moiety, phosphorus containing moiety, amine, alkyl amine, alkyl ether, halide or protecting group. When $R_6$ is an oxygen, it may, with an oxygen at position $R_7$, form a cyclic thiocarbonate as exemplified in structure 27.

For the anthraquinone dynemicin analogs, the $R_1$ through $R_{10}$ groups are as above, and any of the $R_{11}$ to $R_{17}$ groups may be altered. At the broadest level, the $R_{11}$, $R_{12}$, $R_{13}$, $R_{14}$, $R_{15}$, $R_{16}$ and $R_{17}$ groups are limited only by the generation and reaction of the appropriate reagent, Structure 103, in the synthesis reaction, outlined below. Thus, $R_{11}$, $R_{12}$, $R_{13}$, $R_{14}$ $R_{15}$, $R_{16}$ and $R_{17}$ groups that allow the Diels-Alder reagent (generically shown in Structure 103) to be synthesized using known methods and the Diels-Alder reaction shown in the last step of the synthesis reaction shown in FIG. 1 to occur are included within the invention.

For example, $R_{11}$ and $R_{16}$ may be hydrogen, hydroxy, alkyl, alkyl ether, or a protecting group. In some embodiments, as will be appreciated by those in the art, there may be an additional R group attached at these positions depending on the valency of the carbon atom to which $R_{11}$ and $R_{16}$ are attached.

$R_{12}$, $R_{13}$, $R_{14}$ and $R_{15}$ may be hydrogen, hydroxy, alkyl, aryl, amine, alkyl amine, alkyl ether, alkoxy, carboxy, substituted carbonyl, sulfur containing moiety, phosphorus containing moiety, halide, or a protecting group. In a preferred embodiment, at least one and preferably at least two of $R_{12}$, $R_{15}$ and $R_{18}$ are not methyoxy nor hydrogen. Additionally, at least one of $R_{12}$, $R_{15}$ and $R_{18}$ are not acetate. Furthermore, $R_{13}$ and $R_{14}$ together with the unsaturated vinylene group between $R_{13}$ and $R_{14}$ may form an aryl group. In a preferred embodiment, $R_{13}$ and $R_{14}$ are both hydrogen.

In an additional embodiment, the dynemicin analogs of the present invention have the general structure shown below in structure 106:

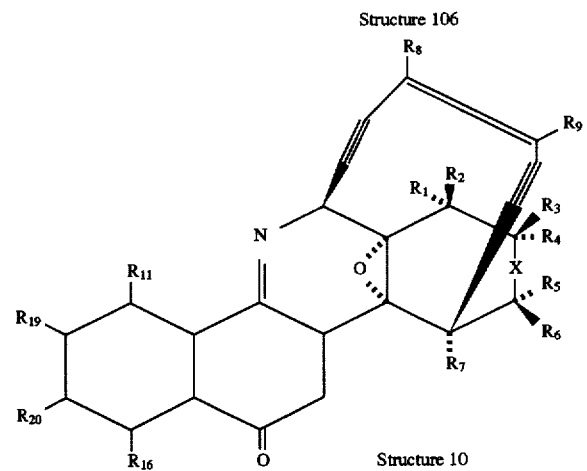

Structure 106 wherein $R_{1-6}$ are the same as above, and $R_{19}$ and $R_{20}$ are the same as $R_{13}$ and $R_{14}$. Structure 106 and analogs may be made using the Diels-Alder reaction using, for example, structure 107 as the reactant.

From the above parameters, there are a variety of dynemicin analogs that are particularly preferred, for example, structures 39, 73, 88, 25 and 84. These are shown below:

Structure 39:

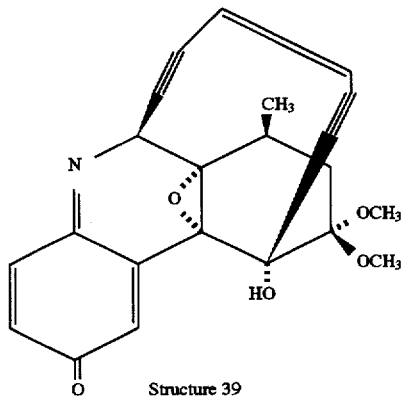

Structure 39

Structure 73:

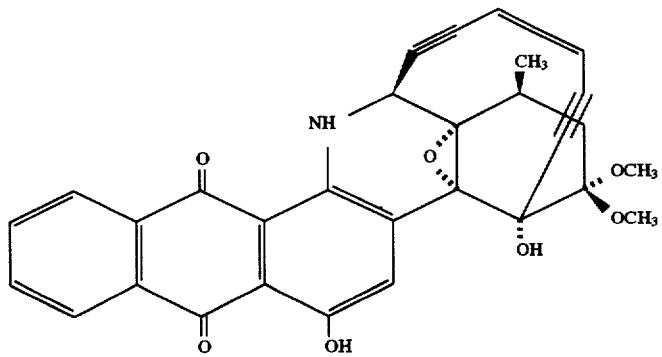

Structure 88

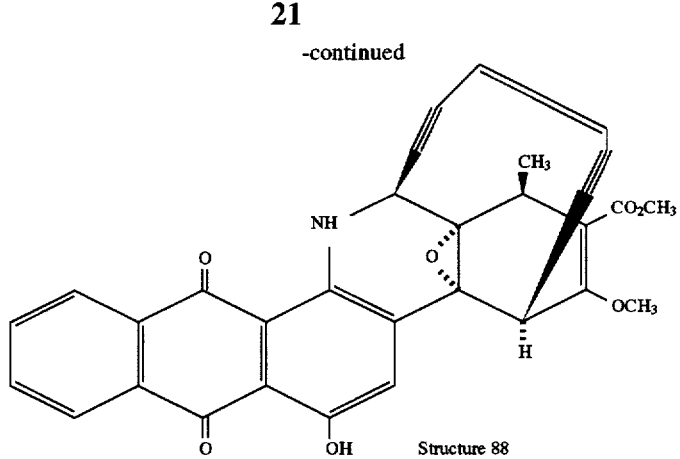

Structure 88

In one embodiment, the dynemicin analogs of the present invention are labelled. By a "labelled dynemicin analog" herein is meant a dynemicin analog that contains at least one element, isotope or chemical compound attached to enable the detection of the dynemicin analog. In general, labels fall into three classes: a) isotopic labels, which may be radioactive; b) immune labels, which may be antibodies or antigens; and c) colored or fluorescent dyes, all of which are known in the art.

In one embodiment, dynemicin may be made using $^{14}C$ or $^{3}H$, such that the dynemicin analog has the same structure as naturally occuring dynemicin but may be detected by means of the radiolabel. Labelled dynemicin analogs will be synthesized by using labelled precursors as shown below in the synthesis, and generally can be incorporated at any position in the structure. In a preferred embodiment, the label or labels are incorporated into the precursor which forms the anthraquinone structure via a Diels-Alder reaction with the quinone imine.

Synthesis of the compounds of the present invention is accomplished using the general scheme outlined in FIG. 1, the specifics of which are shown in the examples.

Generally, the dynemicin analogs are synthesized as follows. A quinone imine dynemicin analog precursor is made, for example, structure 25. Structure 25 may then be converted, using a variety of protocols outlined in the Examples, to alter the $R_3$, $R_4$, $R_5$, $R_6$ and $R_7$ groups of the general structure, as well as to make either the double or single bond at position X. Once this is accomplished, the quinone imine dynemicin analog is formed. Examples of quinone imine dynemicin analogs which are representative of the possible structures include structures 39, 40, 45, 48, 51, 54, and 56. Once a quinone imine dynemicin analog is formed, the anthraquinone dynemicin analogs are formed via Diels-Alder cycloadditions reactions.

More particularly, the general synthetic scheme was developed as follows. In an effort to develop a synthetic route to the dynemicins, a strategy involving the quinone imine (for example, structure 56) as a key intermediate was developed. Although not apparent on the basis of literature precedent, structure is stable, and is suitably activated to deliver the entire right-hand portion of the dynemicins, comprising the strained (Z)-enediyne, epoxide, and vinylogous carbonic acid functional groups, to a variety of acceptor substrates.

Enantiodifferentiation was achieved at the outset of the synthetic route by employing menthol as a chiral auxiliary/resolving agent. Menthyl acetoacetate (1.06 equiv), prepared on the half-kilo scale in 94% yield by thermal transesterification (Witzeman, Tetrahedron Lett. 31:1401 (1990)) of t-butyl acetoacetate with menthol, was condensed with ethyl crotonate (1 equiv) in t-butyl alcohol in the presence of potassium t-butoxide (1.04 equiv) forming the two possible trans-disubstituted 1,3-cyclohexanediones as a 1:1 mixture. A single recrystallization of the crude product mixture (benzene) afforded the diastereomerically pure 1,3-diketone structure 2 (mp 180°–181° C.) in 36% yield. Sterochemical assignments were determined by X-ray crystallographic analysis of the product.

In a typical procedure, 150 g of menthyl acetoacetate was transformed into 65 g of the optically pure, crystalline diketone (structure 2). Treatment of structure 2 with anhydrous methanol and camphorsulfonic acid formed the enol ether (structure 4) regioselectively in 71% yield. Sterochemical assignments were determined by X-ray crystallographic analysis of the product. Deprotonation of structure 4 with sodium hydride in ether and trapping of the resultant enolate with triflic anhydride at −78° C. afforded the corresponding enol triflate (structure 6) in 95% yield. This product was efficiently coupled with t-butyl 2-borono-4-methoxycarbanilate (Pd(PPh$_3$)$_4$, Na$_2$CO$_3$, dioxane, reflux; Miyaura et al., Synth. Commun. 11:513 (1981)) to form the coupling product, structure 9, in 90% yield after recrystallization (mp 141°–142° C.). Thermolysis of structure 9 for 30 min (4-chlorophenol, 180° C.) afforded the quinolone (structure 10) (mp 153°–157° C.) in 84% yield. The solvent is believed to play an important role in this reaction, perhaps as a weak Bronsted acid. Reactions conducted in o-dichlorobenzene at the same temperature, for example, did not proceed to any appreciable extent. Quinolone (structure 10) was transformed into the corresponding trifluoromethanesulfonate derivative with triflic anhydride and 2,6-di-t-butylpyridine in dichloromethane (−78°→0° 86%). Epoxidation of the enol ether double bond using m-chloroperoxybenzoic acid (m-CPBA) in methanol at reflux afforded selectively the α-oriented alcohol structure 13 in 67% yield. Reductive cleavage of the trifluoromethanesulfonate group to form the quinoline (structure 15) was accomplished in 97% yield by heating structure 13 in dioxane at reflux containing formic acid (2.6 equiv), triethylamine (4.0 equiv), and Pd(PPh$_3$)$_4$ (0.04 equiv; Cacchi et al., Tetrahedron Lett., 24:1801 (1983)). To exchange the aryl methyl ether group for the more labile t-butyldimethylsilyl group, structure 15 was treated initially with ethylmagnesium bromide (1.1 equiv) in tetrahydrofuran (THF) at 0° C. (to prevent nucleophilic attack on the dimethyl ketal group) and the resulting magnesium alkoxide was heated with excess sodium ethylmercaptide in N,N- dimethylformamide (DMF) at reflux for 1.5 h. (Feutrill et al., Tetrahedron Lett. (1970) 1327). The diol product of the latter reaction was isolated in 71% yield; protection of the phenol (tert-butyldimethylsilyl chloride, imidazole, DMF; Corey et al., J. Am. Chem. Soc. 94:6190 (1972)) afforded the silyl ether (structure 17) (91%).

At this juncture, the enediyne bridge was introduced using a modification of the methodology of Yamaguchi and co-workers (Tetrahedron Lett. 24:1801 (1983)). For the preferred embodiment, a critical feature of this step concerns the stereochemistry of the carbon-carbon bond formation, where the desired product must result from addition of the magnesium acetylide to the same face of the N-acylpyridinium intermediate as that occupied by the methyl group, i.e. when $R_2$ is a methyl group. This requirement was easily met, and with high stereoselectivity (>20:1), when the addition reaction was conducted with the magnesium salt of alcohol (structure 17). However, the alternative stereochemistry may also be made by conducting the addition reaction with a protected for of the hydroxyl group ($R_7$), e.g. tert-butyldimethylsilyl. Thus, the alcohol (structure 17) was treated with ethylmagnesium bromide (0.9 equiv) in THF at 0° C. and the resulting alkoxide was combined with (Z)-1-bromomagnesio-6-(t-butyldimethylsilyl)hex-3-ene-1,5-diyne (2.0 equiv) in the presence of allyl chloroformate (2.0 equiv) to form the adduct (structure 19) in 89% yield (10-g scale). The high stereoselectivity of this addition reaction is believed to be due to the involvement of a reactive half-chair conformation in which magnesium is chelated to the alkoxide and one or both methoxyl oxygens, placing the methyl group in a pseudoequatorial orientation. Selective epoxidation of the allylic alcohol (structure 19) proceeded smoothly with m-CPBA in a two-phase mixture of dichloromethane and pH 7 aqueous phosphate buffer solution to provide the α-epoxide in 88% yield. Removal of both t-butyldimethylsilyl groups occurred upon treatment of the latter product with tetrabutylammonium fluoride in THF (100%); reprotection of the phenol with t-butyldimethylsilyl chloride and imidazole in DMF (Corey et al., supra) then provided the alcohol (structure 23) in 96% yield. Swern oxidation of structure 23 (oxalyl chloride, DMSO, $CH_2Cl_2$, -40° C.; triethylamine, -78° C.) afforded the ketone (structure 24) in high yield (92%) and set the stage for closure of the enediyne bridge. Toward this end, addition of 1.1 equiv of potassium hexamethyldisilazide solution to a solution of ketone (structure 24) in THF at -78° C. containing 3 equiv of cerium(III) chloride (Myers et al., J. Am. Chem. Soc. 113:694 (1991)) produced the strained addition product (structure 25) in 94% yield after purification by flash column chromatography (Still et al., J. Org. Chem., 43:2923 (1978)).

Completion of the A-ring was initiated by hydrolysis of the dimethyl ketal group of structure 25 with p-toluenesulfonic acid hydrate in acetone at 23° C., furnishing the ketone (structure 26) in 83% yield. Exposure of the latter product to excess 1,1'-thiocarbonyldiimidazole and N,N-dimethylaminopyridine (DMAP, 1.5 equiv) in dichloromethane at reflux produced the cyclic thionocarbonate (structure 27) in 85% yield. When structure 27 was heated with tri-n-butyltin hydride (1.4 equiv) and a catalytic amount of azobisisobutyronitrile in deoxygenated toluene at reflux, the ketone (structure 28) was obtained in 97% yield (Barton et al., J. Chem. Soc. Perkin Trans. 1:1574 (1975); Nicolaou et al., J. Am. Chem. Soc. 112:7416 (1990)). The seemingly straightforward sequence of carboxylation α to the ketone within structure 28 and methyl enol ether formation proved to be one of the most difficult operations in the route. After extensive experimentation, it was discovered that mild conditions for ketone carboxylation (Matsumura et al., Nippon Kaguku Kaishi (1977) 1344; Tirpak et al., J. Org. Chem. 50:4877 (1985)) involving stirring a solution of structure 27 in acetonitrile under a carbon dioxide atmosphere in the presence of magnesium bromide (2.5 equiv) and triethylamine (15 equiv), led to efficient conversion of structure 28 to the corresponding α-keto acid. Addition of a solution of the sensitive keto acid in ether to a suspension of potassium tert-butoxide (5 equiv) in ether at -78° C., and transfer of the resulting solution to a solution of methyl triflate (5 equiv) in toluene at -20° C. afforded the enol methyl ether carboxylic acid (structure 33) in 34% yield for the two-step sequence. Cleavage of the 1-butyldimethylsilyl ether group of structure 33 with triethylamine hydrogen fluoride complex in acetonitrile at 23° C. and oxidation of the resulting phenol with 1.1 equiv of iodosobenzene in methanol at 23° C. afforded the protected quinone imine (structure 53) in 89% yield (we are unaware of exact precedent for this transformation; for related transformations, see Barrett et al., Tetrahedron Lett., 32:2133 (1991) and Swenton et al., J. Org. Chem., 55:2019 (1990)). Removal of the allyl carbamate group of structure 53 to reveal the quinone imine was found to proceed with greater efficiency when the carboxyl group was protected as the corresponding triisopropylsilyl ester (structure 55) (triisopropylsilyl triflate, triethylamine, dichloromethane, -78°→0° C., 85% yield). Treatment of structure 55 with 1.0 equiv of tri-n-butyltin hydride in wet dichloromethane containing $Pd(PPh_3)_2Cl$, as catalyst then afforded the quinone imine (structure 56) in 60% yield. As anticipated, the quinone imine (structure 56) proved to be stable to chromatography on silica gel, to routine manipulations, and to storage. The same sequence of steps, desilylation, oxidation, and deprotection, transformed intermediates (structures 25, 26, 28 and 33) methyl ester into analogous quinone imines in 50–70% yield for the sequence. These compounds are each stable materials that are nevertheless activated toward a variety of carbon-carbon bond forming reactions in the C-ring, most notably Diels-Alder cycloaddition reactions, and have been transformed into both natural and nonnatural dynemicins, as described in the examples.

As will be understood by those in the art, the synthetic pathways outlined herein provide means for the construction of a wide variety of dynemicin analogs with differing structures. For example, as noted above, it is possible to construct a dynemicin analog with the enediyne bridge on the opposite side of the molecule.

In addition, alternative sterochemistries are possible. For example, as shown in FIG. 1, the sterochemistry of the $R_1$ and $R_2$ groups may be varied depending on whether structure 2 or structure 3 is used in the subsequent reactions. Thus, quinone imine dynemicin analogs and anthraquinone dynemicin analogs with, for example, a methyl group in either orientation are possible. In addition, in a preferred embodiment, the menthol added in the first step is (-)-menthol. This leads to the preferred enantiomeric dynemicin analog series. In an additional embodiment, the menthol is (+)-menthol, which leads to the opposite enatiomeric dynemicin series.

In some embodiments, the dynemicin analogs of the present invention are further purified if necessary after synthesis, for example to remove unreacted materials. For example, the dynemicin analogs may be crystallized, or passed through silica gel or flash chromatography columns using solvent mixtures to elute the pure dynemicin analogs. In addition, pure diasteromers may be purified from diasteromeric mixtures if necessary, using the above techniques.

Once produced, the dynemicin analogs of the present invention may be used in a variety of applications.

In one embodiment, the dynemicin analogs of the present invention are used to generate and purify antibodies. In some embodiments, the dynemicin analogs are used as haptens and coupled to protein carriers to generate antibodies, as is known in the art. In other embodiments, the dynemicin analogs are not coupled but are used by themselves. The dynemicin analogs may be coupled using known methods to affinity chromatography columns for the purification of dynemicin analog antibodies or other compounds which bind to the dynemicin analog.

Once generated, the antibodies are useful in a number of applications. In some embodiments, the antibodies will recognize naturally occuring dynemicin; in others, the antibodies are specific for the dynemicin analog. The antibodies may be insolubilized in accord with known methods as agents for the purification of dynemicin and dynemicin analogs. These antibodies are useful in the diagnostic assay of dynemicin or dynemicin analogs, i.e. to screen production cultures or organisms.

The dynemicin analogs of the present invention also find use as nucleic acid cleaving agents. Without being bound by theory, it appears that the anthraquinone portion of the molecule intercalates into the stacked bases of a double helical nucleic acid, for example DNA, and the remainder of the molecule fits into the minor groove of the helix, resulting in tight binding. Upon treatment with various agents, e.g. thiols or biological reducing agents such as NADPH, a sequence or cascade of reactions occurs within the dynemicin analogs leading to DNA cleavage. Thus the dynemicin analogs of the present invention are useful as chemical mutagens. For example, using a DNA-cleaving dynemicin analog and DNA polymerases unable to correctly repair DNA, random mutations are generated. The amount of mutation will vary with the ratio of dynemicin analog to DNA. See Sambrook et al., Molecular Cloning, A Laboratory Manual, Second Edition, 1989. Additionally, the dynemicin analogs can be used to randomly cleave genomes for the construction of libraries, similar to a restriction enzyme.

In a preferred embodiment, the dynemicin analogs are useful to inhibit the growth of cells, particularly rapidly growing cells. Both the qunione imine dynemicin analogs as well as the anthraquinone dynemicin analogs are useful in this application. The cells may be pathogens in a host, for example, bacterial or fungal infections, or may be tumor cells within a host.

In a preferred embodiment, the dynemicin analogs of the present invention are useful as antibiotics. In general, the dynemicin analogs will be administered in a manner similar to other antibiotics. Thus a therapeutically effective dose of a dynemicin analog is administered to a patient. By "therapeutically effective dose" herein is meant a dose that produces the effects for that it is administered. Generally, the dose of dynemicin analog will be determined by comparison to other antibiotics; thus, for example, an amount of dynemicin analog which produces the same extent of microbial death in standard assays as a known dose of a known antibiotic will be used. Customarily, this will be in the range of about 0.001 to about 10 mg/kg.

In a preferred embodiment, the dynemicin analogs are useful as antitumor agents, similar to dynemicin A. Without being bound by theory, rapidly dividing cells such as tumor cells contain DNA in conformations generally acessible to intercalating agents such as dynemicin analogs, are thus more susceptible to intercalating agents than slower growing cells, such as non-tumor cells, whose DNA is not undergoing rapid replication. Thus the genomes of rapidly dividing cells will be cleaved by the dynemicin analog, frequently resulting in cell and tumor death.

In addition, as shown in Example 4, the some or all of the dynemicin analogs may be involved in the inhibition of topoisomerase. When screened against 59 cell lines, the pattern of growth inhibition by a particular compound gives a "fingerprint" which may be associated with a particular function, for example based on chemotherapeutic agents already known and tested in the system. In the case of the dynemicin analogs, it appears that they share a "fingerprint", although little or no structural similarities, with inhibitors of topoisomerase, for example, camtothecin.

In this embodiment, a therapeutically effective dose of a dynemicin analog is administered to a patient. The exact dose will depend on a variety of factors, including the type of tumor to be treated, the size and number of the tumors, the age, body weight, general health, sex, diet, time of administration, drug interaction and the severity of the cancer, and will be ascertainable by one skilled in the art using known techniques. In general, the dynemicin analogs of the present invention are administered at about 0.001 to about 10 mg/kg per day.

The administration of the dynemicin analogs of the present invention can be done in a variety of ways, including, but not limited to, orally, subcutaneously, intravenously, intranasally, transdermally, intraperitoneally, intramuscularly, intrapulmonary, vaginally, rectally, or intraocularly.

The pharmaceutical compositions of the present invention comprise a dynemicin analog in a form suitable for administration to a patient, as will be apparent to those skilled in the art.

The quinone imine dynemicin analogs and anthroquinone dynemicin analogs of the present invention have defined melting points, and thus the compounds are also useful in the calibration of thermocouplers and thermometers, as will be appreciated by those in the art.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLES

Example 1

Preparation of Quinone Imine Dynemicin Analog Precursor

Structure 25 was used to create a variety of quinone imine dynemicin analogs, which were then converted to anthraquinone dynemicin analogs. Structure 25 was synthesized using reactions 1-23.

Reaction 1

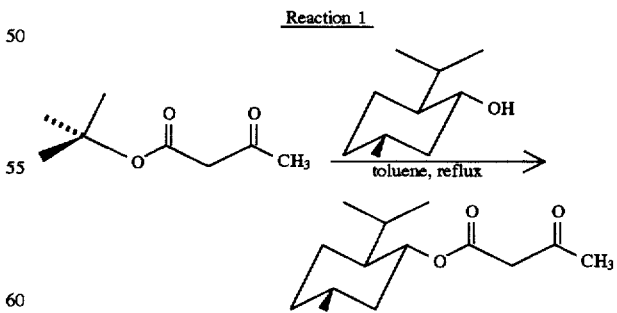

(1R,3R,4S)-p-Menth-3-yl Acetoacetate (1)

A solution of (−)-menthol (23.0 g, 147 mmol, 1 equiv) and 1-butyl acetoacetate (20.0 ml, 121 mmol, 0.80 equiv) in toluene (50 mL) was heated at reflux for 12 h, then was cooled to 23° C. Volatiles were removed in vacuo and toluene (20 mL) and 1-butyl acetoacetate (12.2 mL, 73.5 mmol, 0.50 equiv) were added to the residue. The resulting solution was heated at reflux for 12 h, then was cooled to 23° C. The cooled reaction mixture was concentrated in vacuo and the residue was purified by distillation under reduced pressure (bp 90° C., 30 mmHg) to afford (1R,3R,4S)-p-menth-3-yl acetoacetate (1) as a low-melting solid (33.3 g, 94%).

white powder (mp 180°–181° C., 64.5 g, 36%). To isolate the diastereomeric diketone product, (1R,3R,4S)-p-menth-3-yl(1S,2R)-2-methyl-4,6-dioxocyclohexanecarboxylate (3), the mother liquors were concentrated and the solid residue was dissolved in boiling ethyl acetate (ca. 200 mL). Hexanes (50 mL) were added to the hot solution and the mixture was allowed to cool to 23° C. Further cooling to −20° C. induced crystallization of diketone diastereomer 3 over a period of 12 h (mp 140°–141° C., 45 g, 25%).

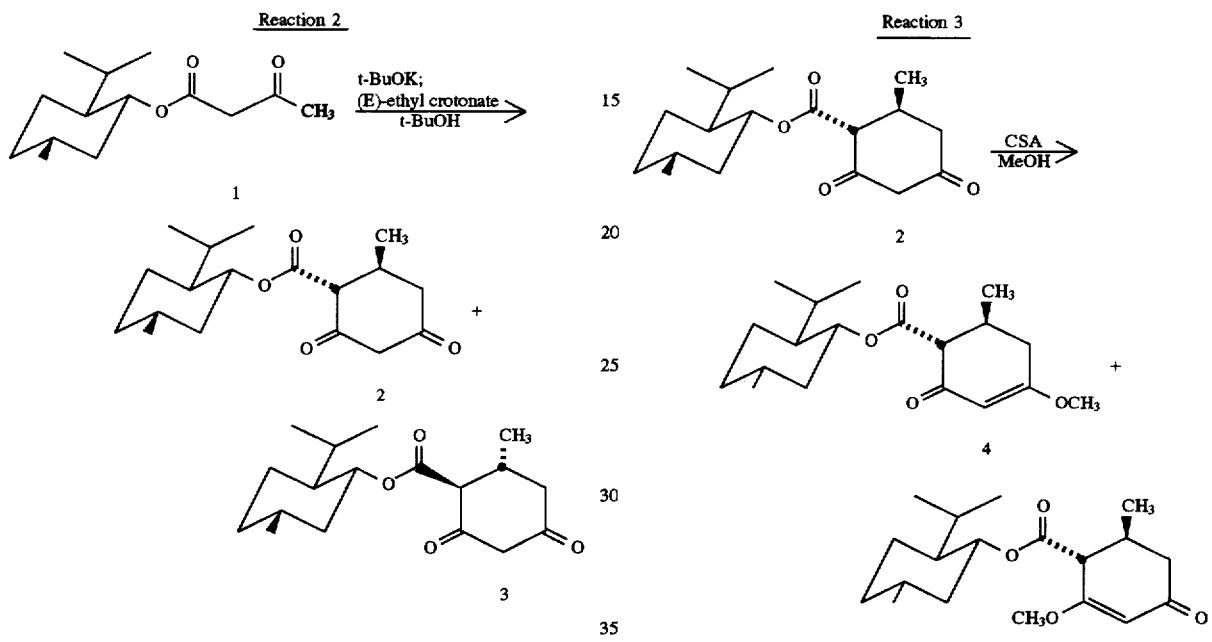

1R,3R,4S)-p-Menth-3-yl(1R,2S)-2-Methyl-4,6-dioxocyclo-hexanecarboxylate (2)

A 2-L 3-necked round bottom flask fitted with a reflux condenser, a mechanical stirrer, and a glass stopper was charged with t-butyl alcohol (300 mL) and potassium 1-butoxide (68.7 g, 612 mmol, 1.04 equiv). The glass stopper was removed and, with efficient mechanical stirring, (1R,3R,4S)-p-menth-3-yl acetoacetate (1, 150 g, 624 mmol, 1.06 equiv) was added rapidly to the yellow slurry. The open neck of the reaction flask was fitted with a 100-mL addition funnel containing (E)-ethyl crotonate (73.2 mL, 588 mmol, 1 equiv). The largely solid reaction mixture was heated to reflux with a heating mantle. At this point, (E)-ethyl crotonate was added to the refluxing, dark yellow slurry over 15 min via the addition funnel. The addition funnel was replaced with a glass stopper and heating at reflux was continued. Solids were observed to dissolve within 1 h after addition of (E)-ethyl crotonate; the product began to crystallize from solution after about 1.5 h. After a total reflux period of 2.5 h (from addition of (E)-ethyl crotonate), heating was discontinued and the reaction mixture was allowed to cool to 23° C. The cooled reaction mixture was partitioned between aqueous sulfuric acid solution (5% v/v, 500 mL) and dichloromethane (600 mL). The aqueous layer was separated and extracted further with two 600-mL portions of dichloromethane. The combined organic layers were dried over sodium sulfate and then were concentrated. The solid residue was dissolved in boiling benzene (ca. 600 mL) and the resulting solution was allowed to cool slowly to 23° C. whereupon (1R,3R,4S)-p-menth-3-yl(1R,2S)-2-methyl-4,6-dioxocyclo-hexanecarboxylate (2) crystallized as a (1R,3R,4S)-p-Menth-3-yl(1R,6S)-Methoxy-6-methyl-2-oxo-3-cyclohexene-1-carboxylate (4)

A solution of (1R,3R,4S)-p-menth-3-yl(1R,2S)-2-methyl-4,6-dioxocyclohexanecarboxylate (2, 24.0 g, 77.8 mmol, 1 equiv) in methanol (300 mL) was treated with camphorsulfonic acid (ca. 800 mg, 3.9 mmol, 0.05 equiv) and the resulting solution was stirred at 23° C. for 12 h. The reaction mixture was neutralized by the addition of solid potassium carbonate (1.08 g, 7.78 mmol, 0.10 equiv) and the resulting suspension was filtered and the filtrate was concentrated. The residue was concentrated from toluene (2×15 mL) and then was purified by flash column chromatography (20% ethyl acetate-hexanes) to afford (1R,3R,4S)-p-menth-3-yl (1R,6S)-4-methoxy-6-methyl-2-oxo-3-cyclohexene-1-carboxylate (4) as a white solid (mp 78°–80° C., 17.9 g, 71%). The regioisomeric enone, (1R,3R,4S)-p-menth-3-yl (1R,6S)-2-methoxy-6-methyl-4-oxo-2-cyclohexene-1-carboxylate (5) was isolated in separate fractions and was resubjected to the reaction conditions to establish the equilibrium mixture of enones, in which the desired product 4 is strongly favored.

Reaction 4:

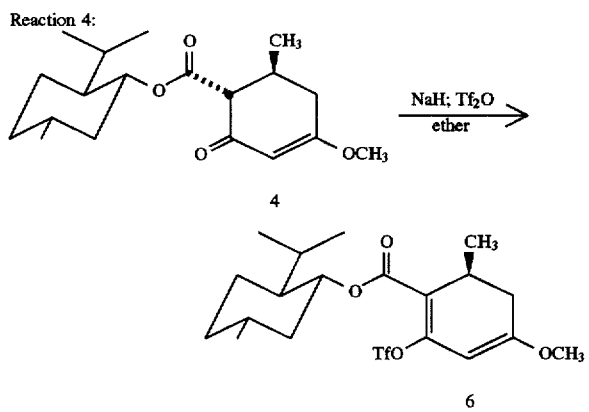

(1R,3R,4S)-p-Menth-3-yl(S)-2-Hydroxy-4-methoxy-6-methyl-1,3-cyclohexadiene-1-carboxylate, Trifluoromethanesulfonate (6)

A solution of (1R,3R,4S)-p-menth-3-yl(1R,6S)-4-methoxy-6-methyl-2-oxo-3-cyclohexene-1-carboxylate (4, 35.5 g, 110 mmol, 1 equiv) in ether (300 mL) was transferred by cannula over 15 min to a stirring suspension of sodium hydride (3.96 g, 165 mmol, 1.50 equiv) in ether (100 mL) at 0° C. The slurry was allowed to warm to 23° C. over approximately 10 min, and was stirred at that temperature for 5 h. Excess sodium hydride was quenched by the addition of 10-mL aliquots of water to the suspension at 30-min intervals until such point as gas evolution was no longer evident. The reaction mixture was then cooled to −78° C. and trifluoromethanesulfonic anhydride (29.6 mL, 176 mmol, 1.60 equiv) was added by syringe over 10 min. Upon completion of the latter addition, the reaction mixture was placed in an ice bath and was stirred for 30 min. The product solution was partitioned between aqueous phosphate buffer solution (pH 7, 0.05M in sodium hydrogen phosphate and 0.05M in potassium dihydrogen phosphate, 400 mL) and ether (400 mL). The aqueous layer was separated and extracted further with ether (2×400 mL). The combined organic layers were dried over sodium sulfate, and then were concentrated. The residue was purified by flash column chromatography (10% ethyl acetate-hexanes) to afford (1R,3R,4S)-p-menth-3-yl(S)-2-hydroxy-4-methoxy-6-methyl-1,3-cyclohexadiene-1-carboxylate, trifluoromethane-sulfonate (6) as a pale yellow oil (47.3 g, 95%). Due to its instability to storage, product 6 was typically carried directly on to the next step in the sequence.

Reaction 5:

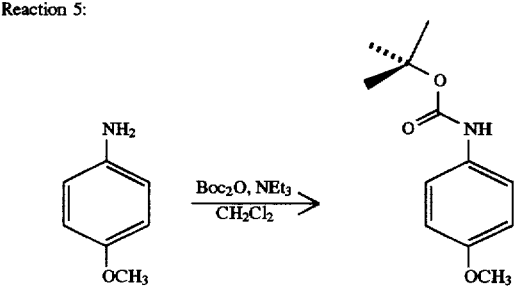

tert-Butyl 4-Methoxycarbanilate

Di-t-butyl dicarbonate (100 g, 458 mmol, 1.20 equiv) was added cautiously over 5 min to a solution of p-anisidine (47.0 g, 382 mmol, 1 equiv) and triethylamine (53.2 mL, 382 mmol, 1 equiv) in dichloromethane (600 mL) at 0° C., producing a mild exotherm. After the exotherm had subsided, the reaction mixture was warmed to 23° C. and was stirred for 5 h at that temperature. The product solution was washed with saturated aqueous ammonium chloride solution (3×500 mL), was dried over sodium sulfate, and was then concentrated in vacuo. The crude product was dissolved in boiling ethyl acetate (800 mL) and hexanes (100 mL) was added to the hot solution. Slow cooling to 23° C., and then to −20° C., induced crystallization of tert-butyl 4-methoxycarbanilate over a period of 12 h. The crystalline product was collected by filtration (mp 93°–94° C., 72.3 g, 85%).

Reaction 6:

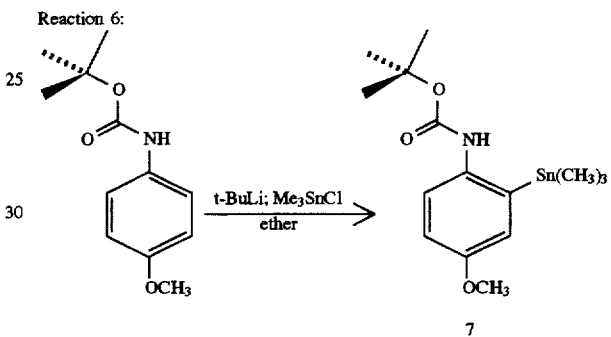

tert-Butyl 4-Methoxy-2-(trimethylstannyl)carbanilate (7)

A solution of t-butyllithium in pentane (1.70M, 148 mL, 251 mmol, 2.50 equiv) was added via cannula to a solution of tert-butyl 4-methoxycarbanilate (22.4 g, 100 mmol, 1 equiv) in ether (500 mL) at −20° C., producing a cloudy yellow solution. After stirring at −20° C. for 5 h, the reaction mixture was cooled to −78° C. and a solution of trimethyltin chloride (50.0 g, 251 mmol, 2.50 equiv) in ether (50 mL) was added via cannula. After the addition, the reaction mixture was warmed to −20° C. and was stirred at that temperature for 30 min, then was stirred in an ice bath for 30 min. The product solution was partitioned between aqueous phosphate buffer solution (pH 7, 0.05M in sodium hydrogen phosphate and 0.05M in potassium dihydrogen phosphate, 600 mL) and ether (400 mL). The aqueous layer was separated and further extracted with ether (2×400 mL). The combined organic layers were dried over sodium sulfate and were concentrated. The product was purified by flash column chromatography (15% ethyl acetate-hexanes) to afford tert-butyl 4-methoxy-2-(trimethylstannyl)carbanilate (7) as a yellow oil (33.3 g, 85%).

Reaction 7:

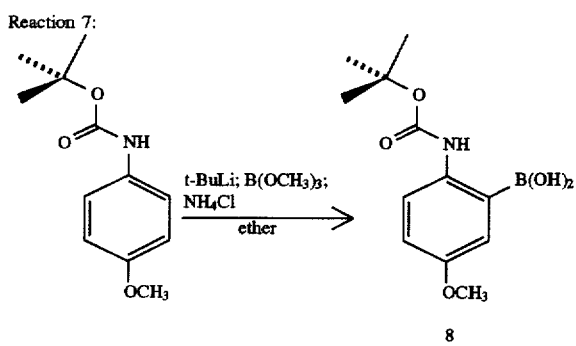

tert-Butyl 2-Borono-4-methoxycarbanilate (8)

A solution of t-butyllithium in pentane (1.70M, 200 mL, 340 mmol, 2.50 equiv) was added via cannula to a solution of tert-butyl 4-methoxycarbanilate (30.4 g, 136 mmol, 1 equiv) in ether (500 mL) at −20° C., producing a cloudy yellow solution. After stirring at −20° C. for 5 h, trimethyl borate (46.3 mL, 408 mmol, 3.00 equiv) was added. The resulting viscous solution was swirled by hand for 5 min, then was allowed to warm to 23° C. and was held at that temperature for 12 h. The product solution was partitioned between saturated aqueous ammonium chloride solution (500 mL) and ethyl acetate (500 mL). The aqueous layer was separated and further extracted with ethyl acetate (2×500 mL). The combined organic layers were dried over sodium sulfate and were concentrated. The product was purified by flash column chromatography (2.5% methanol-dichloromethane initially, grading to 10% methanol-dichloromethane) to provide the tert-Butyl 2-Borono-4-methoxycarbanilate (8) as a yellow powder (19.9 g, 55%).

Reaction 8A and 8B:

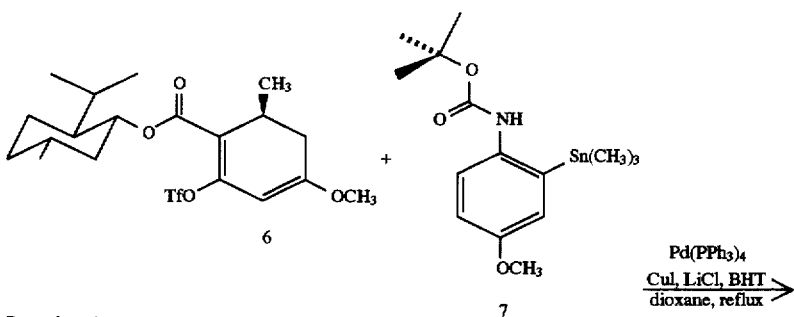

Procedure A

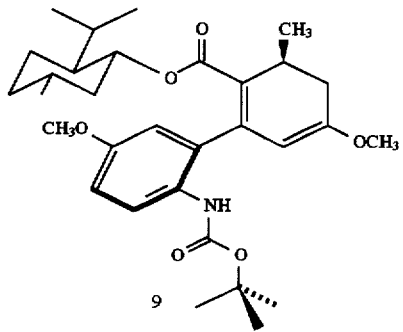

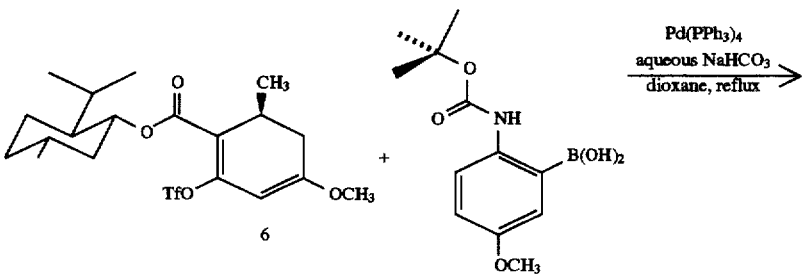

Procedure B

2-[(S)-2-Carboxy-5-methoxy-3-methyl-1,5-cyclohexadien-1-yl]-4-methoxycarbanilic Acid, N-tert-Butyl(1R,3R,4S)-p-Menth-3-yl Ester (9)

Procedure A

Tetrakistriphenylphosphine palladium (1.50 g, 1.30 mmol, 0.05 equiv) and copper iodide (200 mg, 1.05 mmol, 0.04 equiv) were added sequentially to a deoxygenated solution of (1R,3R,4S)-p-menth-3-yl-(S)-2-hydroxy-4-methoxy-6-methyl-1,3-cyclohexadiene-1-carboxylate, trifluoromethanesulfonate (6, 11.2 g, 24.6 mmol, 1 equiv), tert-butyl 4-methoxy-2-(trimethylstannyl)carbanilate (7, 10.4 g, 26.8 mmol, 1.05 equiv), lithium chloride (3.40 g, 112 mmol, 4.40 equiv), and 2,6-di-t-butyl-4-methylphenol (100 mg, 454 mmol, 0.02 equiv) in dioxane (200 mL). The resulting solution was deoxygenated by alternately evacuating the reaction vessel and flushing with argon (5×). The deoxygenated reaction mixture was heated at reflux for 1 h, causing the solution to turn from yellow to black. After cooling to 23° C., the product solution was filtered through a pad of Celite and the filtrate was concentrated in vacuo. The residue was dissolved in ethyl acetate (500 mL) and was washed sequentially with aqueous phosphate buffer solution (pH 7, 0.05M in sodium hydrogen phosphate and 0.05M in potassium dihydrogen phosphate, 2×300 mL) and saturated aqueous sodium chloride solution (300 mL). The organic layer was dried over sodium sulfate and was concentrated. The crude product was dissolved in boiling ethyl acetate (400 mL) and hexanes (100 mL) was added to the hot solution. Slow cooling to 23° C. induced crystallization of the product; further cooling to −20° C. produced additional crystals. The crystals were isolated by filtration. The mother liquor was concentrated and was purified by flash column chromatography (15% ethyl acetate-hexanes), followed by recrystallization (ethyl acetate-hexanes, as above). The combined yield of crystalline product 9 was 10.5 g (81%).

Procedure B

Tetrakistriphenylphosphine palladium (2.78 g, 2.40 mmol, 0.04 equiv) was added to a deoxygenated mixture of aqueous sodium carbonate solution (2.0M, 48.5 mL, 97.0 mmol, 1.45 equiv) and a solution of (1R,3R,4S)-p-menth-3-yl(S)-2-hydroxy-4-methoxy-6-methyl-1,3-cyclohexadiene-1-carboxylate, trifluoromethanesulfonate (6, 30.4 g, 66.9 mmol, 1 equiv) and tert-butyl 2-borono-4-methoxycarbanilate (8, 19.9 g, 74.3 mmol, 1.11 equiv) in dioxane (220 mL). The reaction mixture was deoxygenated by alternately evacuating the reaction vessel and flushing with argon (5×) and then was heated at reflux for 45 min. The product mixture was cooled to 23° C. and was concentrated to half the original volume in vacuo. The concentrated product solution was partitioned between water (400 mL) and ethyl acetate (400 mL). The aqueous layer was separated and extracted further with ethyl acetate (2×400 mL). The combined organic layers were dried over sodium sulfate and were concentrated. The product was purified by chromatography on silica gel (10% ethyl acetate-hexanes initially, grading to 20% ethyl acetate-hexanes) and then by recrystallization [ethyl acetate (800 mL) and hexanes (150 mL)], affording product 9 after two crops of crystals (mp 141°–142° C., 31.9 g, 90%).

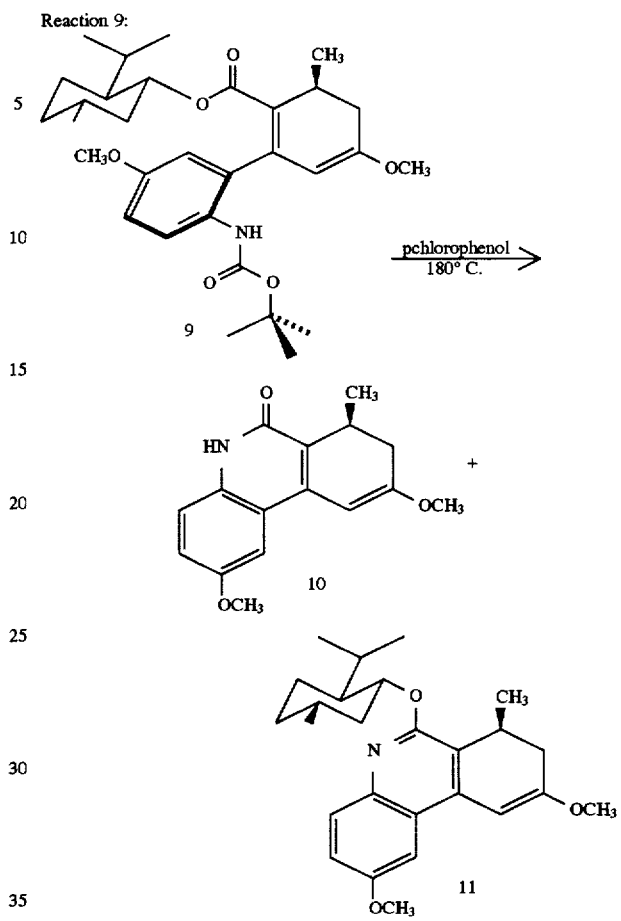

Reaction 9:

(S)-7,8-Dihydro-2,9-dimethoxy-7-methyl-6(5H)-phenanthridin one (10)

A deoxygenated, solid mixture of coupling product 9 (23.5 g, 44.5 mmol) and p-chlorophenol (ca. 400 g) was heated at 180° C. for 30 min, whereupon all solids dissolved. The product solution was cooled to 23° C. and p-chlorophenol was removed by distillation under high vacuum. The residue was purified by flash column chromatography (dichloromethane initially, grading to 10% methanol-dichloromethane) to afford (S)-7,8-dihydro-2,9-dimethoxy-7-methyl-6(5H)-phenanthridinone (10) as a yellow solid (mp 153°–157° C., 10.2 g, 84%). The by-product (S)-7,8-dihydro-6-[(1R,3R,4S)-p-menth-3-yloxy]-2,9-dimethoxy-7-methylphenanthridine (11) was isolated in separate fractions and could be converted to the desired product 10 by resubjection to the reaction conditions (5 h, 98%).

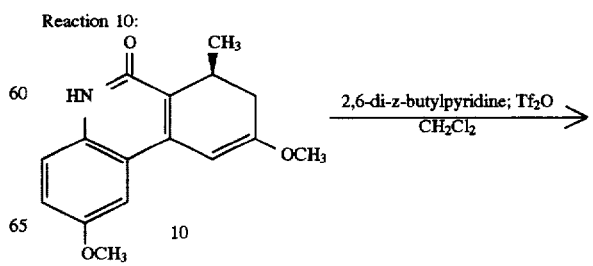

Reaction 10:

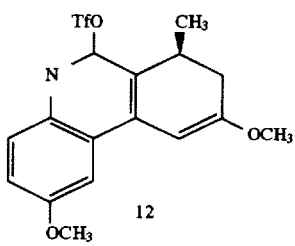

(S)-7,8-Dihydro-2,9-dimethoxy-7-methyl-6-phenanthridinol trifluoromethanesulfonate(Ester) (12)

Trifluoromethanesulfonic anhydride (3.80 mL, 22.4 mmol, 1.10 equiv) was added via syringe to a suspension of (S)-7,8-dihydro-2,9-dimethoxy-7-methyl-6(5H)-phenanthridinone (10, 5.52 g, 20.3 mmol, 1 equiv) and 2,6-di-t-butylpyridine (6.10 mL, 27.1 mmol, 1.33 equiv) in dichloromethane (400 mL) at −78° C. The cold suspension was allowed to warm to 23° C. over 30) min and was stirred at that temperature for 15 min. Solids were observed to dissolve as the reaction proceeded. The reaction mixture was poured into aqueous phosphate buffer solution (pH 7, 0.05M in sodium hydrogen phosphate and 0.05M in potassium dihydrogen phosphate, 200 mL). The aqueous layer was separated and further extracted with two 200-mL portions of dichloromethane. The combined organic layers were dried over sodium sulfate and were concentrated in vacuo. The residue was purified by flash column chromatography (40% dichloromethane-hexanes) to provide (S)-7,8-dihydro-2,9-dimethoxy-7-methyl-6-phenanthridinol trifluoromethanesulfonate (ester) (12) as an off-white solid (mp 129.5°–130.5° C., 7.09 g, 86%).

Reaction 11:

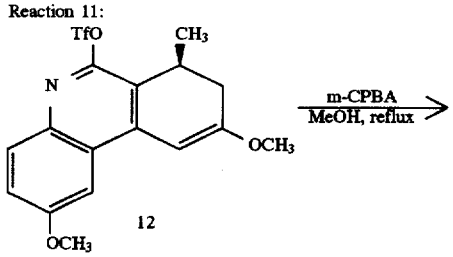

(7S,10R)-7,8,9,10-Tetrahydro-2,9,9-trimethoxy-7-methyl-6,10-phenanthridinediol6-(Trifluoromethane-sulfonate) (13)

A solution of (S)-7,8-dihydro-2,9-dimethoxy-7-methyl-6-phenanthridinol trifluoromethanesulfonate (ester) (12, 3.00 g, 7.40 mmol, 1 equiv) and m-CPBA (5.10 g, 14.9 mmol, 2.00 equiv) in methanol (120 mL) was heated at reflux for 1 h. After cooling to 23° C., the reaction solution was partitioned between 1:1 saturated aqueous sodium bicarbonate solution:saturated aqueous sodium thiosulfate solution (200 mL) and dichloromethane (200 mL). The aqueous layer was separated and extracted further with dichloromethane (2×200 mL). The combined organic layers were dried over sodium sulfate and were concentrated. The residue was purified by flash column chromatography (25% ethyl acetate-hexanes initially, grading to 40% ethyl acetate-hexanes) away from structure 14 to afford (7S,10R)-7,8,9,10-tetrahydro-2,9,9-trimethoxy-7-methyl-6,10-phenanthridinediol 6-(trifluoro-methanesulfonate) (13) as a yellow foam (2.12 g, 63%).

Reaction 12:

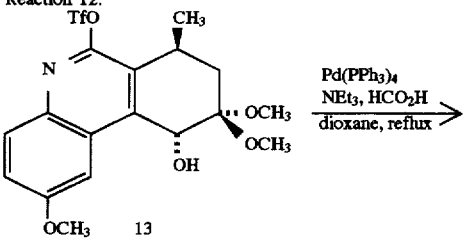

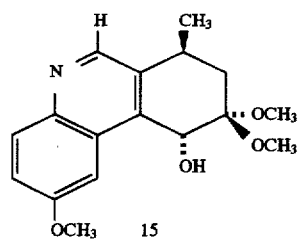

(7S,10R)-7,8,9,10-Tetrahydro-2,9,9-trimethoxy-7-methyl-10-phenanthridinol (15)

Tetrakistriphenylphosphine palladium (778 mg, 673 mmol, 0.04 equiv) was added to a deoxygenated solution of (7S,10R)-7,8,9,10-tetrahydro-2,9,9-trimethoxy-7-methyl-6,10-phenanthridinediol 6-(trifluoromethanesulfonate) (13, 7.60 g, 16.8 mmol, 1 equiv) and triethylamine (9.40 mL, 67.3 mmol, 4.00 equiv) in dioxane (300 mL) at 23° C. The resulting solution was deoxygenated by alternately evacuating the reaction vessel and flushing with argon (5x). Formic acid (1.70 mL, 43.8 mmol, 2.63 equiv) was added slowly over 5 min via syringe and the resulting solution was heated at reflux for 20 min, then was allowed to cool to 23° C. The reaction mixture was partitioned between saturated aqueous sodium chloride solution (300 mL) and ethyl acetate (300 mL). The aqueous layer was separated and further extracted with ethyl acetate (2×300 mL). The combined organic layers were dried over sodium sulfate and were concentrated in vacuo. The residue was purified by flash column chromatography (ether initially, grading to 20% ethyl acetate-ether) to provide (7S,10R)-7,8,9,10-tetrahydro-2,9,9-trimethoxy-7-methyl-10-phenanthridinol (15) as a white foam (mp 135°–136° C., 4.94 g, 97%).

Reaction 13:

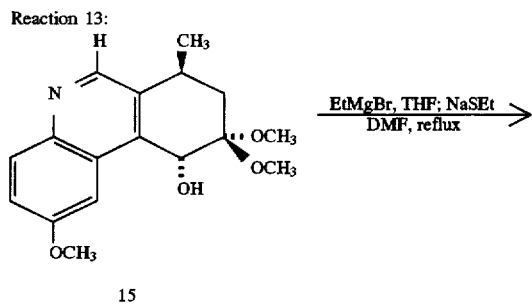

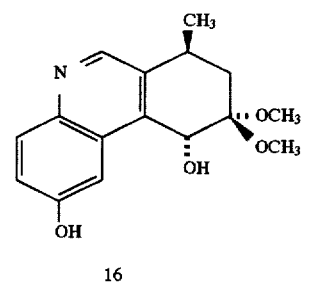

(7S,10R)-7,8,9,10-Tetrahydro-9,9-dimethoxy-7-methyl-2,10-phenanthridinediol (16)

A solution of ethylmagnesium bromide in tetrahydrofuran (1.0M, 8.90 mL, 8.90 mmol, 1.10 equiv) was added by syringe to a solution of (7S,10R)-7,8,9,10-tetrahydro-2,9,9-trimethoxy-7-methyl-10-phenanthridinol (15, 2.46 g, 8.10 mmol, 1 equiv) in tetrahydrofuran (5 mL) at −78° C. The reaction flask was transferred to an ice bath for 10 min, then was cooled to −78° C. A 100-mL flame-dried Schlenk-type flask was charged with sodium hydride (1.17 g, 48.7 mmol, 6.00 equiv) and N,N-dimethylformamide (20 mL) was added slowly over 5 min. The resulting slurry was cooled to 0° C. and ethanethiol (1.80 mL, 24.3 mmol, 3.00 equiv) was added dropwise over 15 min by syringe, causing a vigorous exotherm. After the exotherm had subsided, the slurry was warmed to 23° C. and was stirred at that temperature for 10 min. The tetrahydrofuran solution of the magnesium alkoxide prepared above was added to the slurry via cannula over 5 min. Tetrahydrofuran was then removed in vacuo and the reaction mixture was heated at reflux for 1.5 h. The resulting thick brown slurry was cooled to 23° C. and was partitioned between saturated aqueous ammonium chloride solution (500 mL) and ethyl acetate (500 mL). The aqueous layer was separated and extracted further with ethyl acetate (500 mL) and 20% methanol in dichloromethane (500 mL). The aqueous layer was neutralized by the addition of aqueous hydrochloric acid solution (1% v/v, 400 mL) and was extracted with ethyl acetate (2×500 mL). The combined organic layers were dried over sodium sulfate and were concentrated in vacuo. The residue was purified by flash column chromatography (2.5% methanol-dichloromethane initially, grading to 5% methanol-dichloromethane) to afford (7S,10R)-7,8,9,10-tetrahydro-9,9-dimethoxy-7-methyl-2,10-phenanthridinediol (16) as a yellow solid (1.66 g, 71%).

Reaction 14:

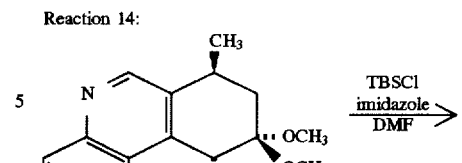

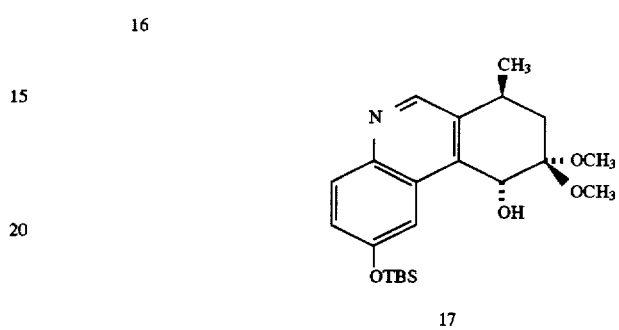

(7S,10R)-2-(tert-Butyldimethylsiloxy)-7,8,9,10-tetrahydro-9,9-dimethoxy-7-methyl-10-phenanthridinol (17)

Imidazole (1.01 g, 14.8 mmol, 2.60 equiv) and t-butyldimethylsilyl chloride (1.11 g, 7.39 mmol, 1.30 equiv) were added sequentially to a solution of (7S,10R)-7,8,9,10-tetrahydro-9,9-dimethoxy-7-methyl-2,10-phenanthridinediol (16, 1.64 g, 5.69 mmol, 1 equiv) in N,N-dimethylformamide (10 mL) at 23° C. After stirring for 1 h at 23° C., the reaction mixture was partitioned between water (100 mL) and ethyl acetate (100 mL). The aqueous layer was separated and extracted further with two 100-mL portions of ethyl acetate. The combined organic layers were dried over sodium sulfate and were concentrated. The residue was purified by flash column chromatography (30% ethyl acetate-hexanes) to afford (7S,10R)-2-(tert-butyldimethylsiloxy)-7,8,9,10-tetrahydro-9,9-dimethoxy-7-methyl-10-phenanthridinol (17) as a light yellow foam (2.10 g, 91%).

Reaction 15:

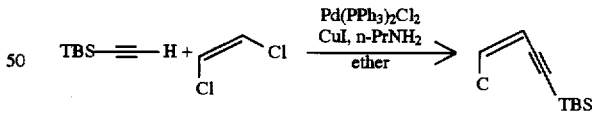

(Z)-1-Chloro-4-(tert-butyldimethylsilyl)-1-buten-3-yne

A solution of tert-butyldimethylsilylacetylene (14.5 g, 103 mmol, 1 equiv), n-propyl amine (42.5 mL, 517 mmol, 5.00 equiv), and (Z)-1,2-dichloroethene (32.5 mL, 413 mmol, 4.00 equiv) in ether (150 mL) was deoxygenated at −78° C. by alternately evacuating the reaction vessel and flushing with argon (8×). The deoxygenated solution was transferred to an ice bath and copper iodide (2.95 g, 15.5 mmol, 0.15 equiv) was added. The mixture was cooled to −78° C. and was deoxygenated as above. In a similar fashion, bis(triphenylphosphine)palladium(II) chloride (3.64 g, 5.17 mmol, 0.05 equiv) was added at 0° C. and the reaction solution was deoxygenated at −78° C. The deoxygenated reaction mixture was warmed to 23° C. and was stirred at that temperature for 3 h. The product solution was washed with 1:1 saturated aqueous potassium carbonate solution:saturated aqueous ammonium chloride solution (3×150 mL), was dried over sodium sulfate, and was concentrated. The residue was purified by distillation under reduced pressure (bp 60°–65° C., mmHg) to afford (Z)-1-chloro-4-(tert-butyldimethylsilyl)-1-buten-3-yne as a clear oil (12.5 g, 60%).

Reaction 16:

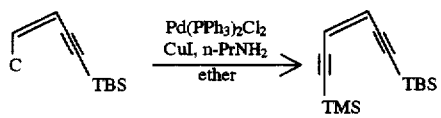

(Z)-1-(tert-Butyldimethylsilyl)-6-trimethylsilyl-3-hexen-1,5-diyne

Tetrakistriphenylphosphine (4.75 g, 4.10 mmol, 0.48 equiv) was added to a solution of (Z)-1-chloro-4-(tert-butyldimethylsilyl)-1-buten-3-yne (17.2 g, 85.7 mmol, 1 equiv) in ether (160 mL) at −78° C. The resulting suspension was deoxygenated by alternately evacuating the reaction vessel and flushing with argon (5×), then was warmed to 23° C. In another flask, copper iodide (2.45 g, 12.8 mmol, 0.15 equiv) was added to a solution of trimethylsilylacetylene (17.0 mL, 120 mmol, 1.40 equiv) and n-propyl amine (27.5 mL, 334 mmol, 3.90 equiv) in ether (100 mL) at −78° C. The solution was deoxygenated (as above, 5×), then was stirred in an ice bath for 10 min causing the light green solution to turn reddish brown. The reddish brown solution was cooled to −78° C. and the palladium-containing suspension prepared above was added over 5 min via a wide-bore cannula. The mixture was deoxygenated (as above, 5×), then was stirred in an ice bath for 3 h and at 23° C. for 1 h. The reaction mixture was partitioned between saturated aqueous ammonium chloride solution (200 mL) and hexanes (300 mL). The aqueous layer was separated and extracted further with hexanes (2×300 mL). The combined organic layers were dried over sodium sulfate and were concentrated. The residue was filtered, then was purified by distillation under reduced pressure (bp 70°–80° C., 0.5 mmHg) to provide (Z)-1-(tert-butyl-dimethylsilyl)-6-trimethylsilyl-3-hexen-1,5-diyne as a light brown oil (20.4 g, 90%).

Reaction 17:

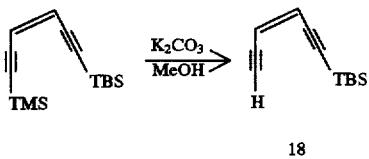

tert-Butyl[(Z)-3-hexene-1,5-diynyl]dimethylsilane (18)

Solid potassium carbonate (5.36 g, 38.9 mmol, 1.10 equiv) was added to a solution of (Z)-1-(tert-butyldimethylsilyl)-6-trimethylsilyl-3-hexen-1,5-diyne (9.26 g, 35.3 mmol, 1 equiv) in methanol (100 mL) at 23° C. and the resulting suspension was stirred at 23° C. for 1 h. The reaction mixture was partitioned between saturated aqueous sodium chloride solution (200 mL) and hexanes (200 mL). The aqueous layer was separated and extracted further with hexanes (200 mL). The combined organic layers were dried over sodium sulfate and were concentrated. The product was purified by flash column chromatography (hexanes) to furnish tert-butyl[(Z)-3-hexene-1,5-diynyl] dimethylsilane (18) as a brown oil (6.35 g, 95%).

Reaction 18:

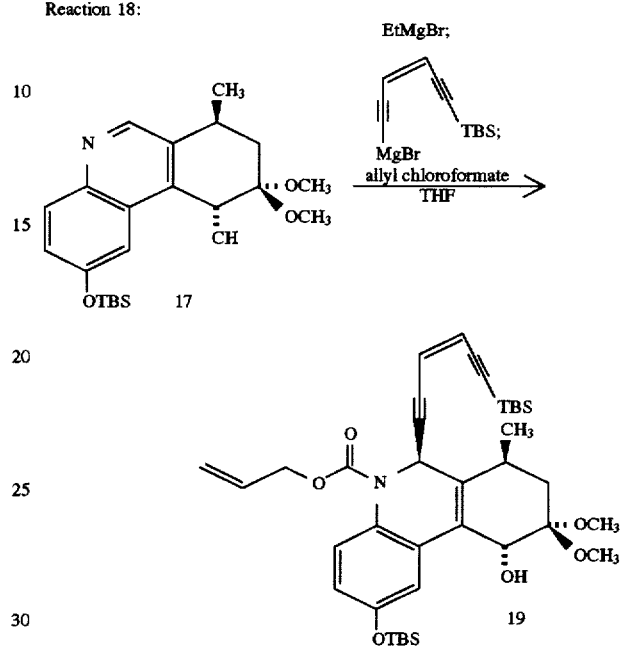

Allyl(6S,7S,10R)-2-(tert-Butyldimethylsiloxy)-6-[(Z)-6-(tert-butyldimethylsilyl)-3-hexene-1,5-diynyl]-7,8,9,10-tetrahydro-10-hydroxy-9,9-dimethoxy-7-methyl-5(6H)-phenanthridinecarboxylate (19)

A solution of ethylmagnesium bromide in tetrahydrofuran (1.0M, 13.6 mL, 13.6 mmol, 0.90 equiv) was added to a solution of (7S,10R)-2-(tert-butyldimethylsiloxy)-7,8,9,10-tetrahydro-9,9-dimethoxy-7-methyl-10-phenanthridinol (17, 6.10 g, 15.1 mmol, 1 equiv) in tetrahydrofuran (30 mL) at −78° C. The mixture was stirred in an ice bath for 10 min, then was cooled to −78° C. In a separate flask, a solution of ethylmagnesium bromide in tetrahydrofuran (1.0M, 22.7 mL, 22.7 mmol, 1.50 equiv) was added to a solution of tert-butyl[(Z)-3-hexene-1,5-diynyl]dimethylsilane (18, 5.75 g, 30.2 mmol, 2.00 equiv) in tetrahydrofuran (20 mL) at 0° C. The resulting solution was warmed to 23° C., then was heated briefly to reflux with a heat gun. After the mixture had cooled to 23° C., it was transferred via cannula over 3 min to the cold solution of magnesium alkoxide derived from the TBS quinoline. Allyl chloroformate (1.20 mL, 14.4 mmol, 2.00 equiv) was added, and the solution was stirred in an ice bath for 2 h. The reaction mixture was partitioned between aqueous phosphate buffer solution (pH 7, 0.05M in sodium hydrogen phosphate and 0.05M in potassium dihydrogen phosphate, 150 mL) and ethyl acetate (150 mL). The aqueous layer was separated and extracted further with ethyl acetate (2×150 mL). The combined organic layers were dried over sodium sulfate and were concentrated. The residue was purified by flash column chromatography (10% ethyl acetate-hexanes initially, grading to 20% ethyl acetate-hexanes) to afford allyl(6S,7S,10R)-2-(tert-butyldimethylsiloxy)-6-[(Z)-6-(tert-butyldimethylsilyl)-3-hexene-1,5-diynyl]-7,8,9,10-tetrahydro-10-hydroxy-9,9-dimethoxy-7-methyl-5(6H)-phenanthridinecarboxylate (19)

as a light yellow foam (9.16 g, 89%). The other product, structure 20, was not used.

Reaction 19:

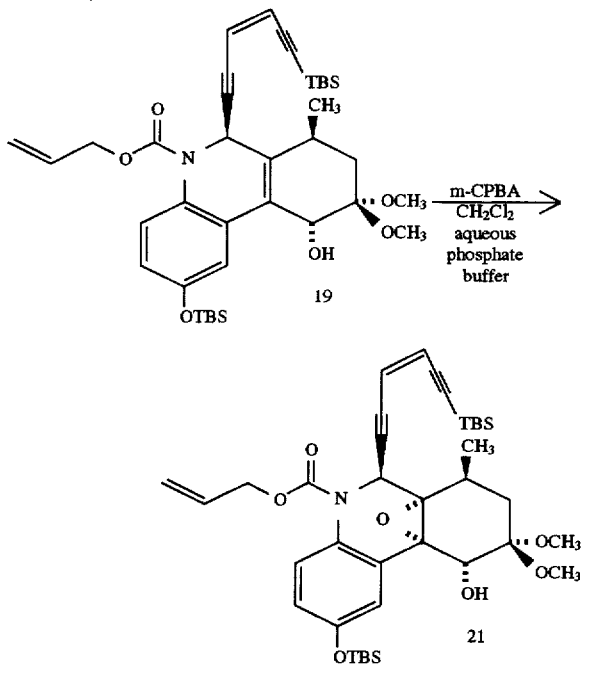

Allyl(6S,6aS,7S,10R,10aS)-2-(tert-Butyldimethylsiloxy)-6-[(Z)-6-(tert-butyldimethylsilyl)-3-hexene-1,5-diynyl]-7,8,0,10-tetrahydro-10-hydroxy-9,9-dimethoxy-7-methyl-6a,10a-epoxyphenanthridine-5 (6H)-carboxylate (21)

m-Chloroperoxybenzoic acid (1.04 g, 3.31 mmol, 2.08 equiv) was added to a biphasic solution of allyl(6S,7S,10R)-2-(tert-butyldimethylsiloxy)-6-[(Z)-6-(tert-butyldimethylsilyl)-3-hexene-1,5-diynyl]-7,8,9,10-tetrahydro-10-hydroxy-9,9-dimethoxy-7-methyl-5(6H)-phenanthridinecarboxylate (19, 1.08 g, 1.59 mmol, 1 equiv) in dichloromethane (50 mL) and aqueous phosphate buffer (pH 7, 0.05M in sodium hydrogen phosphate and 0.05M in potassium dihydrogen phosphate, 50 mL) at 0° C. The reaction mixture was stirred at 0° C. for 18 h. A second portion of m-chloroperoxybenzoic acid (614 mg, 1.96 mmol, 1.23 equiv) was added and the reaction mixture was stirred at 0° C. for another 5 h. A final portion of m-chloroperoxybenzoic acid (459 mg, 1.46 mmol, 0.92 equiv) was added at this point and the reaction mixture was stirred at 0° C. for 3.5 h. The product solution was poured into 1:1 saturated aqueous sodium bicarbonate solution:saturated aqueous sodium thiosulfate solution (400 mL). The aqueous layer was separated and extracted further with dichloromethane (2×100 mL). The combined organic layers were dried over sodium sulfate and were concentrated. The residue was purified by flash column chromatography (20% ethyl acetate-hexanes) to provide allyl(6S,6aS,7S,10R,10aS)-2-(tert-butyldimethylsiloxy)-6-[(Z)-6-(tert-butyldimethylsilyl)-3-hexene-1,5-diynyl]-7,8,0,10-tetrahydro-10-hydroxy-9,9-dimethoxy-7-methyl-6a,10a-epoxyphenanthridine-5(6H)-carboxylate (21) as a yellow foam (967 mg, 88%).

Reaction 20:

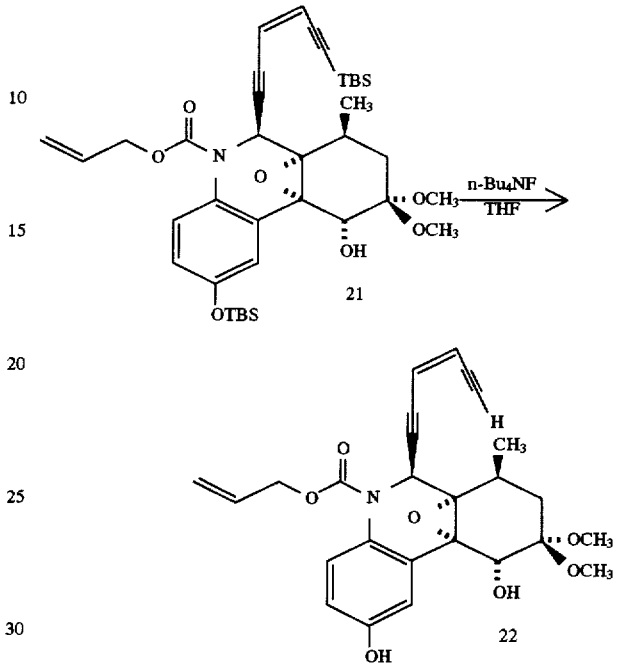

Allyl(6S,6aS,7S,10R,10aS)-6-[(Z)-3-Hexene-1,5-diynyl]-7,8,0,10-tetrahydro-2,10-dihydroxy-9,9-dimethoxy-7-methyl-6a,10a-epoxyphenanthridine-5 (6H)-carboxylate (22)

A 1.0M solution of tetrabutylammonium fluoride in tetrahydrofuran (9.50 mL, 9.50 mmol, 2.00 equiv) was added to a solution of allyl(6S,6aS,7S,10R,10aS)-2-(tert-butyldimethylsiloxy)-6-[(Z)-6-(tert-butyldimethylsilyl)-3-hexene-1,5-diynyl]-7,8,0,10-tetrahydro-10-hydroxy-9,9-dimethoxy-7-methyl-6a,10a-epoxyphenanthridine-5(6H)-carboxylate (21, 3.30 g, 4.75 mmol, 1 equiv) in tetrahydrofuran (100 mL) at 0° C. After stirring at 0° C. for 10 min, the product solution was partitioned between aqueous phosphate buffer solution (pH 7, 0.05M in sodium hydrogen phosphate and 0.05M in potassium dihydrogen phosphate, 150 mL) and dichloromethane (150 mL). The aqueous layer was separated and extracted further with dichloromethane (2×150 mL). The combined organic layers were dried over sodium sulfate and were concentrated. The residue was purified by flash column chromatography (60% ethyl acetate-hexanes) to afford allyl(6S,6aS,7S,10R,10aS)-6-[(Z)-3-hexene-1,5-diynyl]-7,8,0,10-tetrahydro-2,10-dihydroxy-9,9-dimethoxy-7-methyl-6a,10a-epoxyphenanthridine-5(6H)-carboxylate (22) as a yellow foam (2.21 g, 100%).

Reaction 21:

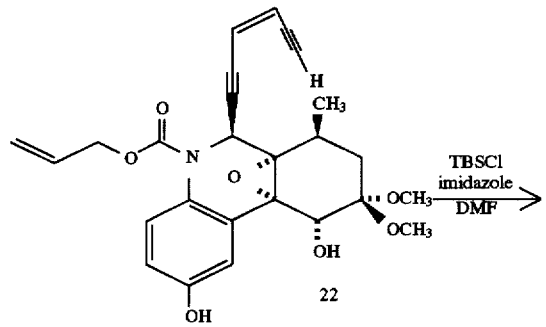

Reaction 22:

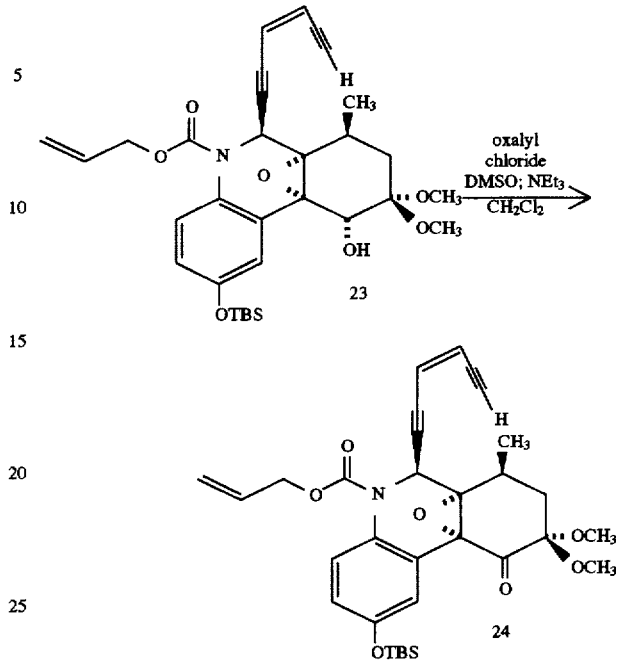

Allyl(6S,6aS,7S,10R,10aS)-2-(tert-Butyldimethylsiloxy)-6-1(Z)-3-hexene-1,5-diynyl]-7,8,9,10-tetrahydro-10-hydroxy-9,9-dimethoxy-7-methyl-6a,10a-epoxyphenanthridine-5(6H)-carboxylate (23)

A solution of allyl(6S,6aS,7S,10R,10aS)-6-[(Z)-3-hexene-1,5-diynyl]-7,8,9,10-tetrahydro-2,10-dihydroxy-9,9-dimethoxy-7-methyl-6a,10a-epoxyphenanthridine-5(6H)-carboxylate (22, 6.10 g, 13.1 mmol, 1 equiv) in N,N-dimethylformamide (80 mL) at 23° C. was treated sequentially with imidazole (2.32 g, 34.1 mmol, 2.60 equiv) and 1-butyldimethylsilyl chloride (2.60 g, 17.0 mmol, 1.30 equiv). After stirring at 23° C. for 1 h, the reaction solution was partitioned between water (300 mL) and ethyl acetate (300 mL). The aqueous layer was separated and extracted further with two 300-mL portions of ethyl acetate. The combined organic layers were dried over sodium sulfate and were concentrated. The residue was purified by flash column chromatography (20% ethyl acetate-hexanes) to provide allyl(6S,6aS,7S,10R,10aS)-2-(tert-butyldimethylsiloxy)-6-[(Z)-3-hexene-1,5-diynyl]-7,8,9,10-tetrahydro-10-hydroxy-9,9-dimethoxy-7-methyl-6a,10a-epoxyphenanthridine-5 (6H)-carboxylate (23) as a yellow foam (7.27 g, 96%).

Allyl(6S,6aS,7S,10aR)-2-(tert-Butyldimethylsiloxy)-6-[(Z)-3-hexene-1,5-diynyl]-7,8,9,10-tetrahydro-9,9-dimethoxy-7-methyl-10-oxo-6a,10a-epoxyphenanthridine-5(6H)-carboxylate (24)

Dimethyl sulfoxide (4.22 mL, 59.5 mmol, 15.0 equiv) was added to a solution of oxalyl chloride (3.46 mL, 39.7 mmol, 10.0 equiv) in dichloromethane (75 mL) at −78° C. After stirring at −78° C. for 20 min, a solution of allyl(6S,6aS,7S,10R,10aS)-2-(tert-butyldimethylsiloxy)-6-[(Z)-3-hexene-1,5-diynyl]-7,8,9,10-tetrahydro-10-hydroxy-9,9-dimethoxy-7-methyl-6a,10a-epoxyphenanthridine-5(6H)-carboxylate (23, 2.30 g, 3.97 mmol, 1 equiv) in dichloromethane (75 mL) was added over 10 min via cannula to the cold reaction solution. The reaction mixture was warmed to −40° C. and was held at that temperature for 10 h. The reaction mixture was then cooled to −78° C., triethylamine (16.6 mL, 119 mmol, 30.0 equiv) was added, and the resulting solution was stirred in an ice bath for 30 min. The product solution was poured into aqueous phosphate buffer solution (pH 7, 0.05M in sodium hydrogen phosphate and 0.05M in potassium dihydrogen phosphate, 150 mL). The aqueous layer was separated and extracted further with dichloromethane (2×150 mL). The combined organic layers were dried over sodium sulfate and were concentrated. The residue was purified by flash column chromatography (2% ethyl acetate-dichloromethane initially, grading to 5% ethyl acetate-dichloromethane) to afford allyl(6S,6aS,7S,10aR)-2-(tert-butyldimethylsiloxy)-6-[(Z)-3-hexene-1,5-diynyl]-7,8,9,10-tetrahydro-9,9-dimethoxy-7-methyl-10-oxo-6a,10a-epoxyphenanthridine-5 (6H)-carboxylate (24) as a light brown foam (2.10 g, 92%).

Reaction 23:

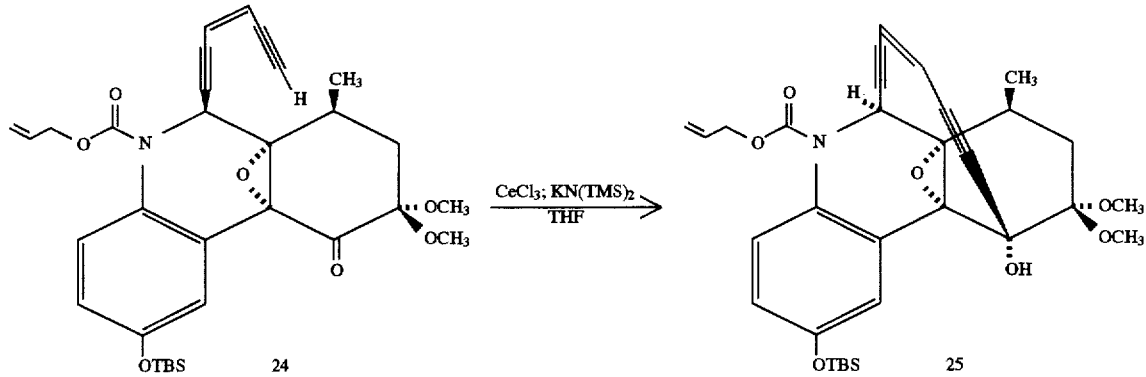

Allyl(6S,6aS,7S,10R,10aS,14Z)-2-(tert-
Butyldimethylsiloxy)-7,8,9,10-tetrahydro-10-
hydroxy-9,9-dimethoxy-7-methyl-6a,10a-epoxy-6,
10-[3]hexene[1,5]diynophenanthridine-5(6H)-
carboxylate (25)

A suspension of cerium trichloride (1.70 g, 6.90 mmol, 4.93 equiv) and allyl(6S,6aS,7S,10aR)-2-(tert-butyldimethylsiloxy)-6-[(Z)-3-hexene-1,5-diynyl]-7,8,9,10-tetrahydro-9,9-dimethoxy-7-methyl-10-oxo-6a,10a-epoxyphenanthridine-5(6H)-carboxylate (24, 810 mg, 1.40 mmol, 1 equiv) in tetrahydrofuran (30 mL) was stirred at 23° C. for 30 min. The suspension was then cooled to −78° C. and a solution of potassium hexamethyldisilylazide in toluene (0.5M, 4.50 mL, 2.25 mmol, 1.61 equiv) was added dropwise over 5 min causing the yellow suspension to turn light brown, then brown, then dark grayish brown. The reaction flask was transferred to an ice bath and saturated aqueous ammonium chloride solution (150 mL) was added. The biphasic mixture was extracted with ethyl acetate (3×150 mL). The combined organic layers were dried over sodium sulfate and were concentrated. The residue was purified by flash column chromatography (25% ethyl acetate-hexanes) to afford allyl(6S,6aS,7S,10R,10aS,14Z)-2-(tert-butyldimethylsiloxy)-7,8,9,10-tetrahydro-10-hydroxy-9,9-dimethoxy-7-methyl-6a,10a-epoxy-6,10-[3] hexene[1,5]diynophenanthridine-5(6H)-carboxylate (25) as a pale yellow foam (761 mg, 94%).

Example 2

Preparation of Quinone Imine Dynemicin Analogs

The quinone imine dynemicin analog structure 25, which is made in Example 1, is used as a precursor to construct other quinone imine dynemicin analogs. Using the reactions below, structure 25 was used to make structure 39, using reactions 30, 31 and 32. Structure 40 was made using reactions 30, 31, 33 and 34. Structure 48 was made using reactions 24, 25, 26, 36 and 37. Structure 51 was made using reactions 24, 25, 26, 28, 29, 38, 39, and 40. Structure 54 was made using reactions 24, 25, 26, 27, 41, 42, and 43. Structure 56 was made using reactions 24, 25, 26, 27, 41, 44, and 45.

Reaction 24:

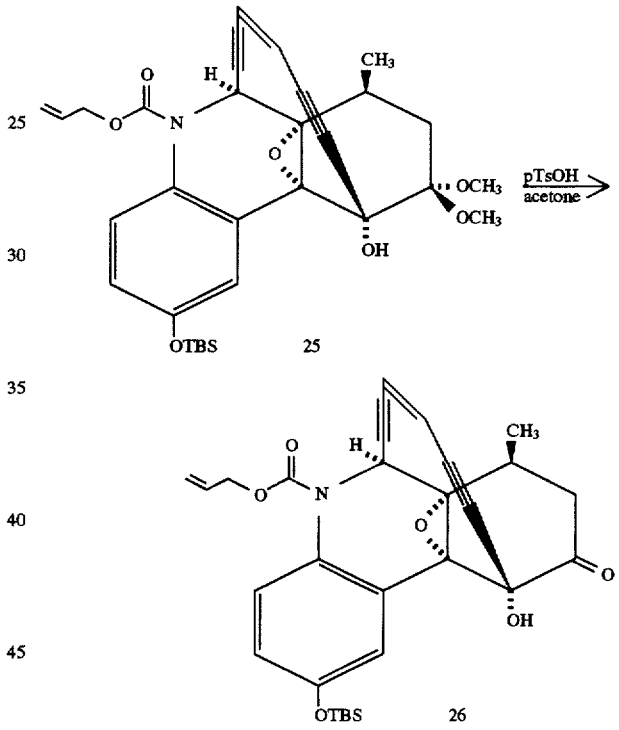

Allyl(6S,6aS,7S,10R,10aS,14Z)-2-(tert-Butyldimethyl-
siloxy)-7,8,9,10-tetrahydro-10-hydroxy-7-methyl-9-
oxo-6a,10a-epoxy-6,10-[3]-hexene[1,5]diynophenan-
thridine-5(6H)-carboxylate (26)

A solution of allyl(6S,6aS,7S,10R,10aS,14Z)-2-(tert-butyldimethylsiloxy)-7,8,9,10-tetrahydro-10-hydroxy-9,9-dimethoxy-7-methyl-6a,10a-epoxy-6,10-[3]hexene[1,5] diynophenanthridine-5(6H)-carboxylate (25, 5.43 g, 9.40 mmol, 1 equiv) in acetone (300 mL) was stirred with p-toluensulfonic acid monohydrate (7.15 g, 37.6 mmol, 4.00 equiv) at 23° C. for 2 h. The reaction solution was partitioned between saturated aqueous sodium bicarbonate solution (300 mL) and ethyl acetate (300 mL). The aqueous layer was separated and extracted further with ethyl acetate (2×300 mL). The combined organic layers were dried over sodium sulfate and were concentrated. The residue was purified by flash column chromatography (25% ethyl acetate-hexanes) to afford allyl(6S,6aS,7S,10R,10aS,14Z)-2-(tert-butyldimethylsiloxy)-7,8,9,10-tetrahydro-10-hydroxy-7-methyl-9-oxo-6a,10a-epoxy-6,10-[3]hexene[1,5]diynophenanthridine-5(6H)-carboxylate (26) as a pale yellow foam (4.03 g, 81%).

Reaction 25:

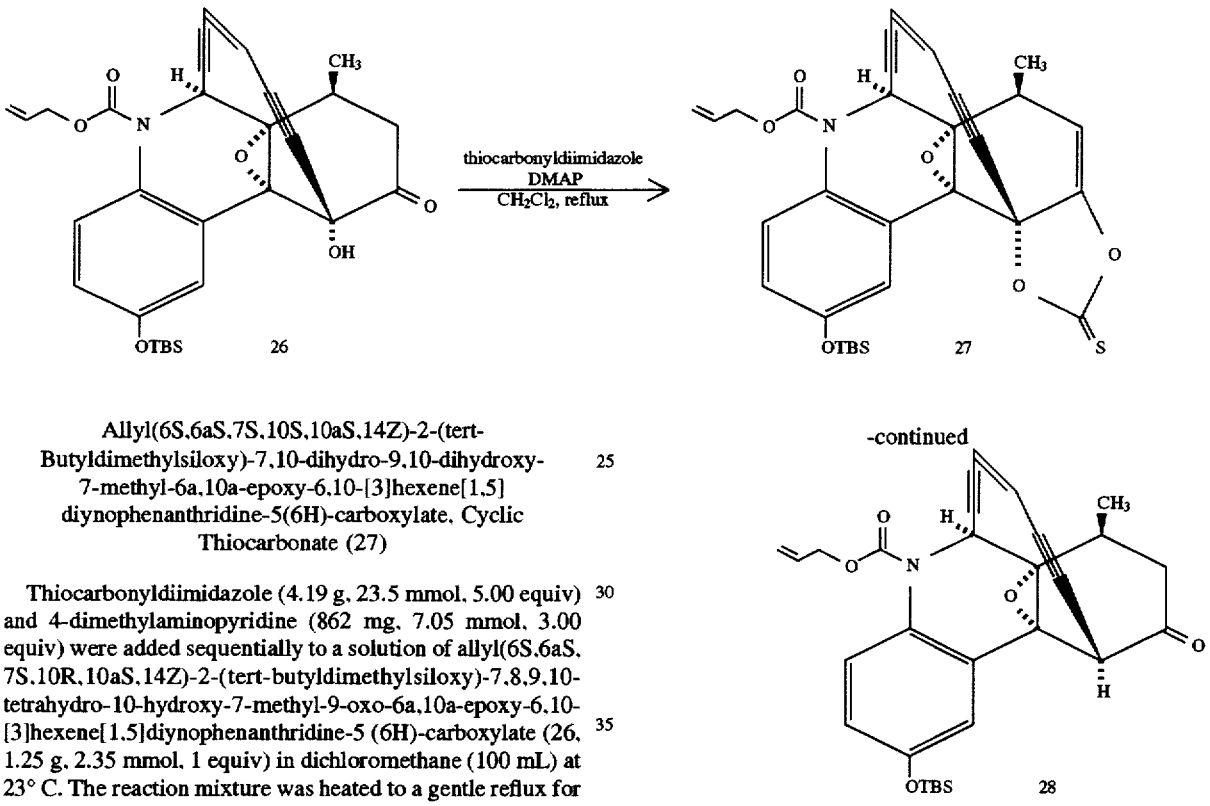

Allyl(6S,6aS,7S,10S,10aS,14Z)-2-(tert-Butyldimethylsiloxy)-7,10-dihydro-9,10-dihydroxy-7-methyl-6a,10a-epoxy-6,10-[3]hexene[1,5]diynophenanthridine-5(6H)-carboxylate, Cyclic Thiocarbonate (27)

Thiocarbonyldiimidazole (4.19 g, 23.5 mmol, 5.00 equiv) and 4-dimethylaminopyridine (862 mg, 7.05 mmol, 3.00 equiv) were added sequentially to a solution of allyl(6S,6aS,7S,10R,10aS,14Z)-2-(tert-butyldimethylsiloxy)-7,8,9,10-tetrahydro-10-hydroxy-7-methyl-9-oxo-6a,10a-epoxy-6,10-[3]hexene[1,5]diynophenanthridine-5 (6H)-carboxylate (26, 1.25 g, 2.35 mmol, 1 equiv) in dichloromethane (100 mL) at 23° C. The reaction mixture was heated to a gentle reflux for 7 h. A second portion of thiocarbonyldiimidazole (838 mg, 4.70 mmol, 2.00 equiv) and 4-dimethylaminopyridine (287 mg, 2.35 mmol, 1 equiv) were added and the reaction mixture was heated to a gentle reflux for an additional 14 h. The reaction mixture was cooled to 23° C. and volatiles were removed in vacuo. The residue was purified by flash column chromatography (30% hexanes-dichloromethane) to afford allyl(6S,6aS,7S,10S,10aS,14Z)-2-(tert-butyldimethylsiloxy)-7,10-dihydro-9,10-dihydroxy-7-methyl-6a,10a-epoxy-6,10-[3]hexene[1,5]diynophenanthridine-5(6H)-carboxylate, cyclic thiocarbonate (27) as an off-white foam (1.15 g, 85%).

Reaction 26:

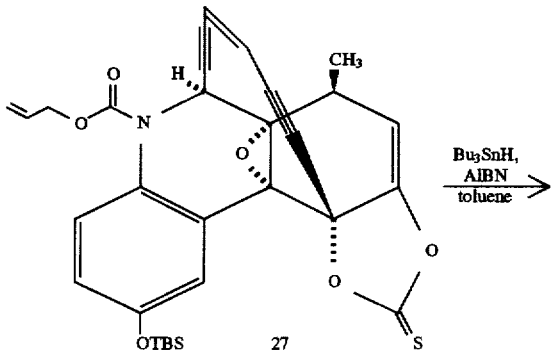

Allyl(6S,6aS,7S,10S,10aR,14Z)-2-(tert-Butyldimethylsiloxy)-7,8,9,10-tetrahydro-7-methyl-9-oxo-6a,10a-epoxy-6,10-[3]hexene[1,5]diynophenanthridine-5(6H)-carboxylate (28)

Tributyltin hydride (722 μL, 2.68 mmol, 1.40 equiv) and azobis(isobutyronitrile) (75.0 mg, 457 μmol, 0.23 equiv) were added sequentially to a solution of allyl(6S,6aS,7S,10S,10aS,14Z)-2-(tert-butyldimethylsiloxy)-7,10-dihydro-9,10-dihydroxy-7-methyl-6a,10a-epoxy-6,10-[3]hexene[1,5]diynophenanthridine-5(6H)-carboxylate, cyclic thiocarbonate (27, 1.10 g, 1.92 mmol, 1 equiv) in toluene (75 mL). The resulting pale yellow solution was deoxygenated by three consecutive freeze-pump-thaw cycles. The mixture was then heated at 70° C. for 30 min. Volatiles were removed in vacuo, and the residue was purified by flash column chromatography (dichloromethane initially, then 1% ethyl acetate-dichloromethane) to furnish allyl(6S,6aS,7S,10S,10aR,14Z)-2-(tert-butyldimethyl-siloxy)-7,8,9,10-tetrahydro-7-methyl-9-oxo-6a,10a-epoxy-6,10-[3]hexene[1,5]diynophenanthridine-5(6H)-carboxylate (28) as an off-white foam (957 mg, 97%).

Reaction 27:

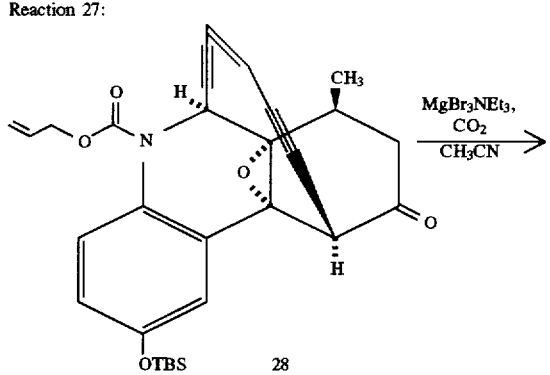

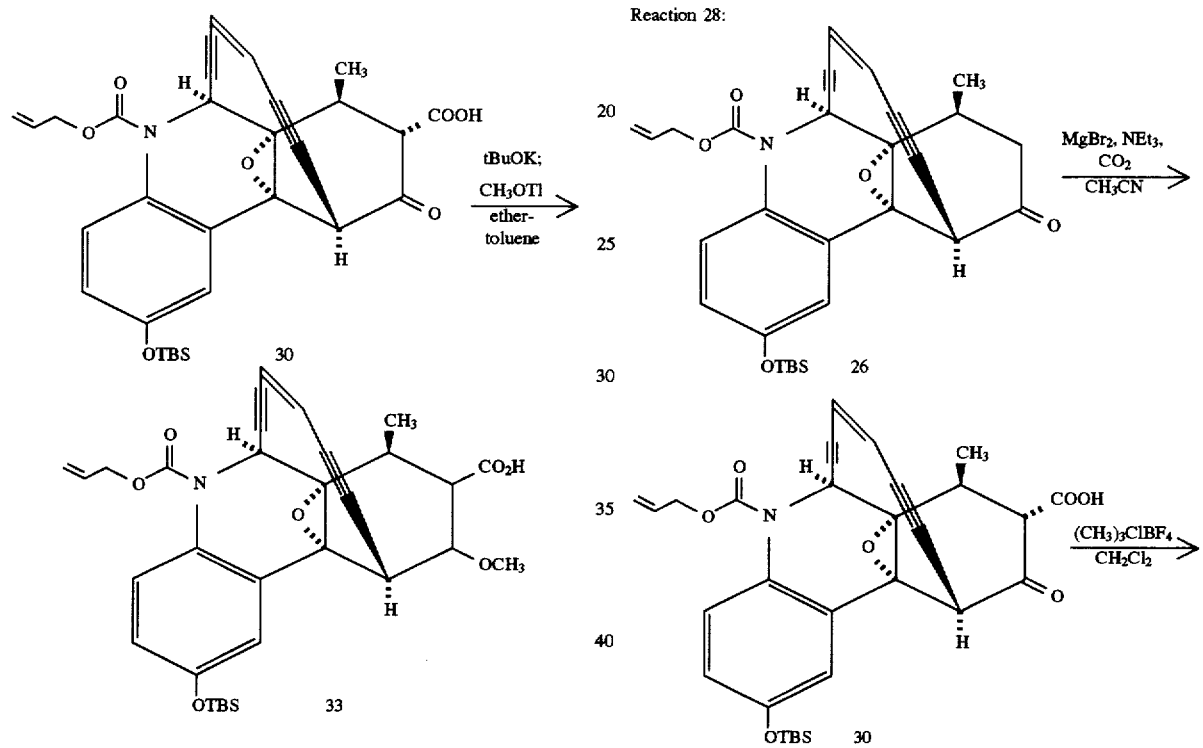

Triethylamine (203 µL, 1.45 mmol, 15.0 equiv) was added to a solution of allyl(6S,6aS,7S,10S,10aR,14Z)-2-(tert-butyldimethylsiloxy)-7,8,9,10-tetrahydro-7-methyl-9-oxo-6a,10a-epoxy-6,10-[3]hexene[1,5]diynophenanthridine-5 (6H)-carboxylate (28, 50.0 mg, 97.0 µmol, 1 equiv) and magnesium bromide (45.0 mg, 242 µmol, 2.50 equiv) in acetonitrile (2 mL) at 23° C. under an atmosphere of carbon dioxide. After stirring for 1 h at 23° C., the reaction solution was concentrated in vacuo. The residue was partitioned between aqueous hydrochloric acid solution (1% v/v, 5 mL) and ether (5 mL). The aqueous layer was separated and was further extracted with ether (2×5 mL). The combined organic layers were washed with saturated aqueous sodium chloride solution (15 mL), were dried over sodium sulfate, and were concentrated to a volume of 500-µL. The concentrated ethereal solution was cooled to −78° C. and was transferred via cannula to a suspension of potassium t-butoxide (44.0 mg, 388 mmol, 4.00 equiv) in ether (500 µL) at −78° C. The transfer was quantitated with additional ether (1 mL). The reaction mixture was stirred at −78° C. for 5 min, then was transferred via cannula over 5 min to a solution of methyl triflate (55.0 mL, 485 mmol, 5.00 equiv) in toluene (2 mL) at −20° C. The transfer was quantitated with additional toluene (1 mL). The reaction mixture was stirred at −20° C. for 40 min. Excess methyl triflate was quenched by the sequential addition of triethylamine (1 mL) and methanol (3 mL). The product solution was partitioned between aqueous hydrochloric acid solution (1N, 10 mL) and dichloromethane (10 mL). The aqueous layer was separated and extracted further with dichloromethane (2×10 mL). The combined organic layers were dried over sodium sulfate and were concentrated. The product was purified by flash column chromatography (25% ethyl acetate-hexanes initially, then 50% ethyl acetate-hexanes) to provide 5-allyl hydrogen(6S,6aS,7S,10R,10aR,14Z)-2-(tert-butyldimethylsiloxy)-7,10-dihydro-9-methoxy-7-methyl-6a,10a-epoxy-6,10-[3]hexene[1,5]diynophenanthridine-5,8 (6H)-dicarboxylate (33) as a pale yellow foam (19 mg, 34%).

Reaction 28:

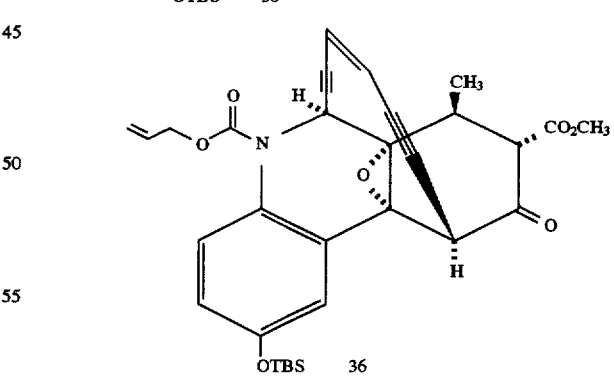

Triethylamine (203 µL, 1.45 mmol, 15.0 equiv) was added to a solution of allyl(6S,6aS,7S,10S,10aR,14Z)-2-(tert-butyldimethylsiloxy)-7,8,9,10-tetrahydro-7- methyl-9-oxo-6a,10a-epoxy-6,10-[3]hexene[1,5]diynophenanthridine-5 (6H)-carboxylate (28, 50.0 mg, 97.0 µmol, 1 equiv) and magnesium bromide (45.0 mg, 242 µmol, 2.50 equiv) in acetonitrile (2 mL) at 23° C. under an atmosphere of carbon dioxide. After stirring for 1 h at 23° C., the reaction solution was concentrated in vacuo. The residue was dissolved in dichloromethane (5 mL) and was cooled to 0° C. Trimethyloxonium tetrafluoroborate (717 mg, 4.58 mmol, 50.0 equiv) was added to the solution. The resulting suspension was warmed to 23° C. and was held at this temperature for 2.5 h. The product suspension was partitioned between saturated aqueous sodium bicarbonate solution (25 mL) and dichloromethane (15 mL). The aqueous layer was separated and extracted further with dichloromethane (2×15 mL). The combined organic layers were dried over sodium sulfate and were concentrated. The product was purified by flash column chromatography (15% ethyl acetate-hexanes) to provide 5-allyl methyl(6S,6aS,7S,8R,10S,10aR,14Z)-2-(tert-butyldimethylsiloxy)-7,8,9,10-tetrahydro-7-methyl-9-oxo-6a,10a-epoxy-6,10-[3]hexene[1,5] diynophenanthridine-5,8(6H)-dicarboxylate (36) as a yellow oil (41 mg, 73%).

Reaction 29:

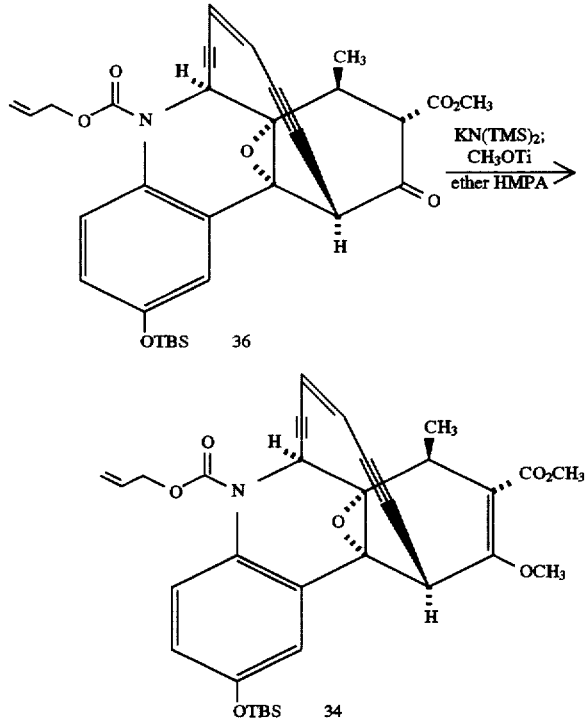

A solution of potassium hexamethyldisilylazide in toluene (0.5M, 648 µL, 324 µmol, 3.00 equiv) was added to a solution of 5-allyl methyl(6S,6aS,7S,8R,10S,10aR,14Z)-2-(tert-butyldimethylsiloxy)-7,8,9,10-tetrahydro-7-methyl-9-oxo-6a,10a-epoxy-6,10-[3]hexene[1,5] diynophenanthridine-5,8(6H)-dicarboxylate (36, 62.0 mg, 108 mmol, 1 equiv) in ether (5 mL) and hexamethylphosphoramide (25 µL) at −78° C. After stirring the resulting solution at −78° C. for 5 min, methyl triflate (37.0 µL, 324 µmol, 3.00 equiv) was added. The reaction mixture was then warmed to 23° C. and was held at this temperature for 1 h. The product solution was partitioned between saturated aqueous sodium bicarbonate solution (20 mL) and ether (15 mL). The aqueous layer was separated and further extracted with ether (20 mL). The combined organic layers were dried over sodium sulfate and were concentrated. The product was purified by flash column chromatography (20% ethyl acetate-hexanes) to furnish 5-allyl methyl(6S,6aS,7S,10R,10aR,14Z)-2-(tert-butyldimethylsiloxy)-7,10-dihydro-9-methoxy-7-methyl-6a,10a-epoxy-6,10-[3]hexene[1,5] diynophenanthridine-5,8(6H)-dicarboxylate (34) as a yellow foam (39 mg, 61%).

Reaction 30:

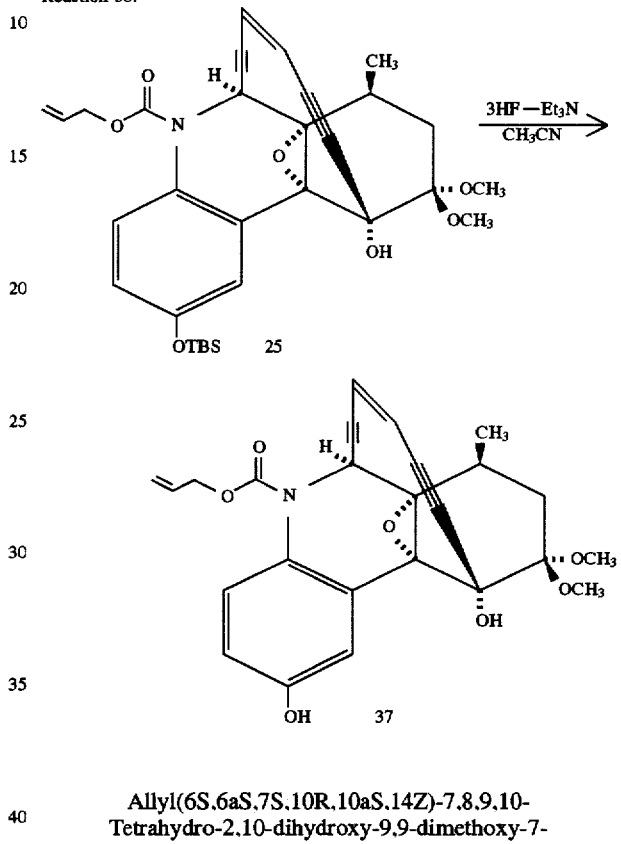

Allyl(6S,6aS,7S,10R,10aS,14Z)-7,8,9,10-Tetrahydro-2,10-dihydroxy-9,9-dimethoxy-7-methyl-6a,10a-epoxy-6,10-[3]hexene[1,5] diynophenanthridine-5(6H)-carboxylate (37)

Triethylamine trihydrofluoride (0.50 mL, 3.1 mmol, 4.5 equiv) was added to a solution of allyl(6S,6aS,7S,10R,10aS,14Z)-2-(tert-butyldimethylsiloxy)-7,8,9,10-tetrahydro-10-hydroxy-9,9-dimethoxy-7-methyl-6a,10a-epoxy-6,10-[3]hexene[1,5]diyno-phenanthridine-5(6H)-carboxylate (25, 390 mg, 0.675 mmol, 1 equiv) in acetonitrile (10 mL) at 23° C. The reaction mixture was stirred at 23° C. for 3 h, then was partitioned between saturated aqueous sodium bicarbonate solution (75 mL) and ethyl acetate (40 mL). The aqueous layer was separated and extracted further with ethyl acetate (40 mL). The combined organic layers were dried over sodium sulfate and were concentrated. The residue was purified by flash column chromatography (20% ethyl acetate in dichloromethane) to yield allyl(6S,6aS,7S,10R,10a,14Z)-7,8,9,10-tetrahydro-2,10-dihydroxy-9,9-dimethoxy-7-methyl-6a,10a-epoxy-6,10-[3]hexene[1,5] diynophenanthridine-5(6H)-carboxylate (37) as a light yellow oil (313 mg, 100%).

Reaction 31:

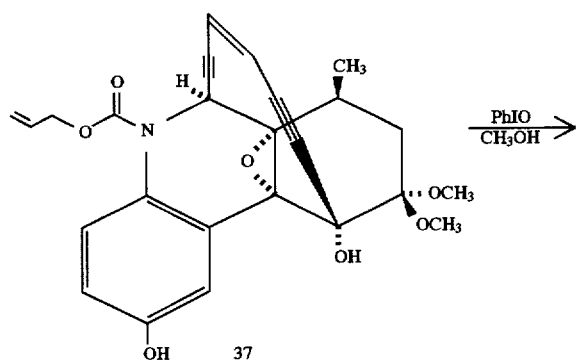

Allyl(4aS,6S,6aS,7S,10R,10aS,14Z)-2,4a,7,8,9,10-Hexahydro-10-hydroxy-4a,9,9-trimethoxy-7-methyl-2-oxo-6a,10a-epoxy-6,10-[3]hexene[1,5][diynophenanthridine-5(6H)-carboxylate (38)

Iodosobenzene (130 mg, 0.591 mmol, 1.14 equiv) was added to a solution of allyl(6S,6aS,7S,10R,10aS,14Z)-7,8,9,10-tetrahydro-2,10-dihydroxy-9,9-dimethoxy-7-methyl-6a,10a-epoxy-6,10-[3]hexene[1,5]diynophenanthridine-5(6H)-carboxylate (37, 240 mg, 0.518 mmol, 1 equiv) in dry methanol (30 mL) at 23° C. The reaction mixture was stirred at 23° C. for 10 min. The product solution was then partitioned between 1:1 saturated aqueous sodium bicarbonate solution:saturated aqueous sodium thiosulfate solution (70 mL), saturated aqueous sodium chloride solution (50 mL), and ethyl acetate (50 mL). The aqueous layer was separated and extracted further with ethyl acetate (50 mL). The combined organic layers were dried over sodium sulfate and were concentrated. The residue was purified by flash column chromatography (40% hexanes in ethyl acetate) to give allyl(4aS,6S,6aS,7S,10R,10aS,14Z)-2,4a,7,8,9,10-hexahydro-10-hydroxy-4a,9,9-trimethoxy-7-methyl-2-oxo-6a,10a-epoxy-6,10-[3]hexene[1,5]diynophenanthridine-5 (6H)-carboxylate (38) as a light yellow oil (228 mg, 89%).

Reaction 32:

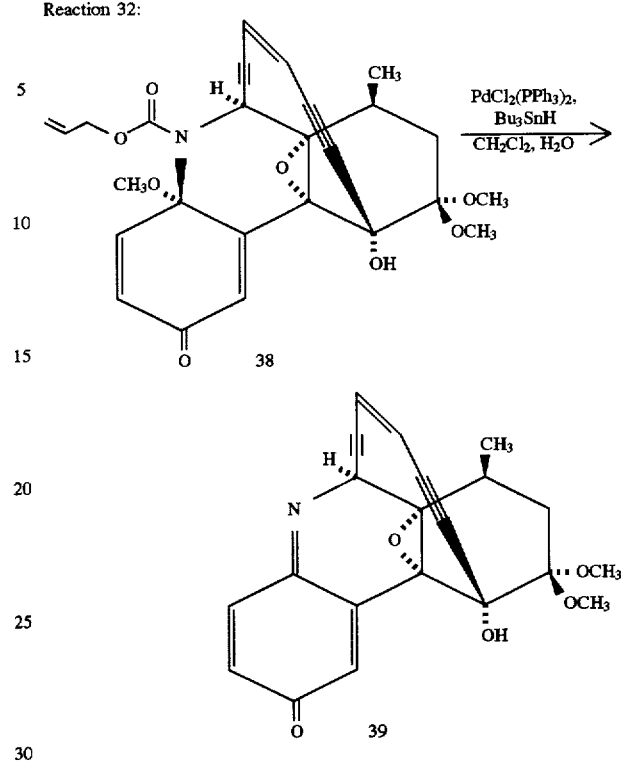

(6S,6aS,7S,10R,10aS,14Z)-7,8,9,10-Tetrahydro-10-hydroxy-9,9-dimethoxy-7-methyl-6a,10a-epoxy-6,10-[3]-hexene[1,5]diynophenanthridin-2(6H)-one (39)

Tributyltin hydride (130 μL, 0.483 mmol, 1.04 equiv) was injected into a deoxygenated suspension of enone (38, 228 mg, 0.463 mmol, 1 equiv), bistriphenylphosphinepalladium (II) chloride (153 mg, 0.218 mmol, 0.471 equiv) and water (100 μL) in dichloromethane (20 mL) at 23° C. The reaction mixture was stirred for 5 min at 23° C., then was loaded directly onto a column of solvated (20% ethyl acetate in hexanes) flash-grade silica gel. Elution (20% ethyl acetate in hexanes initially, grading to 60% ethyl acetate in hexanes) provided (6S,6aS,7S,10R,10aS,14Z)-7,8,9,10-tetrahydro-10-hydroxy-9,9-dimethoxy-7-methyl-6a,10a-epoxy-6,10-[3]hexene[1,5]-diynophenanthridin-2(6H)-one (39) as a yellow oil (143 mg, 82%).

Reaction 33:

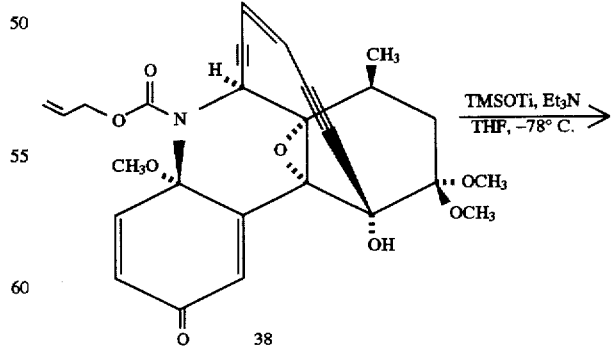

55

Reaction 33: -continued

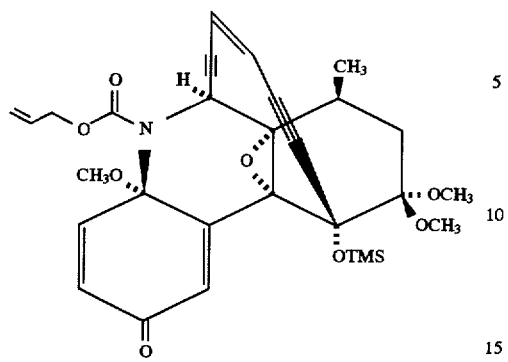

Allyl(4aS,6S,6aS,7S,10R,10aS,14Z)-2,4a,7,8,9,10-Hexahydro-10-trimethylsilyloxy-4a,9,9-trimethoxy-7-methyl-2-oxo-6a,10a-epoxy-6,10-[3]hexene[1,5]diynophenanthridine-5(6H)-carboxylate Trimethylsilyl trifluoromethanesulfonate (240 μL, 1.22 mmol, 5.04 equiv) was added to a solution of allyl(4aS,6S,6aS,7S,10R,10aS,14Z)-2,4a,7,8,9,10-hexahydro-10-hydroxy-4a,9,9-trimethoxy-7-methyl-2-oxo-6a,10a-epoxy-6,10-[3]hexene[1,5]diyno-phenanthridine-5(6H)-carboxylate (38, 119 mg, 0.242 mmol, 1 equiv) and triethylamine (340 μL, 2.44 mmol, 10.1 equiv) in tetrahydrofuran (5 mL) at −78° C. The reaction mixture was transferred to an ice bath and was stirred for 10 min at 0° C. The product solution was partitioned between saturated aqueous sodium bicarbonate solution (50 mL) and ethyl acetate (40 mL). The aqueous layer was separated and extracted further with ethyl acetate (40 mL). The combined organic layers were dried over sodium sulfate and were concentrated. The residue was purified by flash column chromatography (40% ethyl acetate in hexanes) to provide allyl(4aS,6S,6aS,7S,10R,10aS,14Z)-2,4a,7,8,9,10-hexahydro-10-trimethylsilyloxy-4a,9,9-trimethoxy-7-methyl-2-oxo-6a,10a-epoxy-6,10-[3]hexene[1,5]diynophenanthridine-5(6H)-carboxylate as a light yellow oil (118 mg, 87%).

Reaction 34:

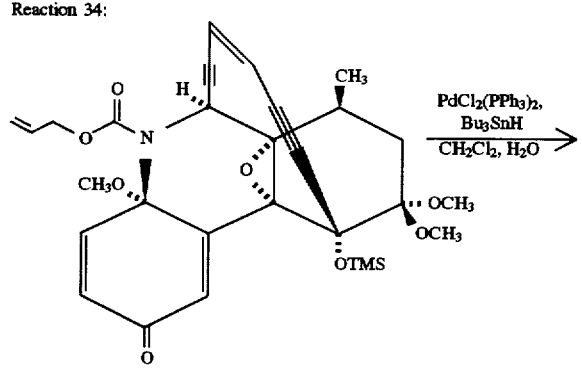

56

Reaction 34: -continued

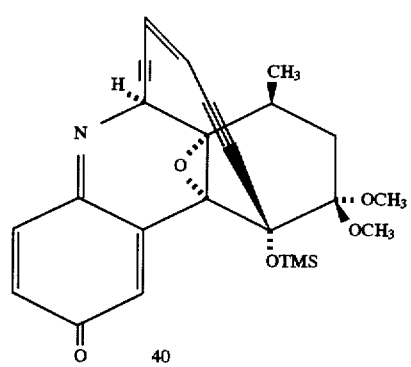

(6S,6aS,7S,10R,10aR,14Z)-7,8,9,10-Tetrahydro-9,9-dimethoxy-7-methyl-10-(trimethylsiloxy)-6a,10a-epoxy-6,10-[3]hexene[1,5]diynophenanthridin-2(6H)-one (40)

Tributyltin hydride was injected in two portions (8.0 μL, 0.030 mmol, 0.67 equiv; 4.0 mL, 0.015 mmol, 0.33 equiv) with a 10 min interval between injections into a deoxygenated suspension of allyl(4aS,6S,6aS,7S,10R,10aS,14Z)-2,4a,7,8,9,10-hexahydro-10-trimethylsilyloxy-4a,9,9-trimethoxy-7-methyl-2-oxo-6a,10a-epoxy-6,10-[3]hexene[1,5]diynophenanthridine-5(6H)-carboxylate (25 mg, 0.044 mmol, 1 equiv), bistriphenylphosphinepalladium(II) chloride (3.0 mg, 0.0043 mmol, 0.096 equiv) and water (150 μL) in dichloromethane (8 mL) at 23° C. The reaction mixture was then stirred for 5 min at 23° C. The product solution was concentrated in vacuo and the residue was purified by flash column chromatography (40% ethyl acetate in hexanes) to provide (6S,6aS,7S,10R,10aR,14Z)-7,8,9,10-tetrahydro-9,9-dimethoxy-7-methyl-10-(trimethyl-siloxy)-6a,10a-epoxy-6,10-[3]hexene[1,5]diynophenanthridin-2(6H)-one (40) as a yellow oil (14 mg, 70%).

Reaction 35:

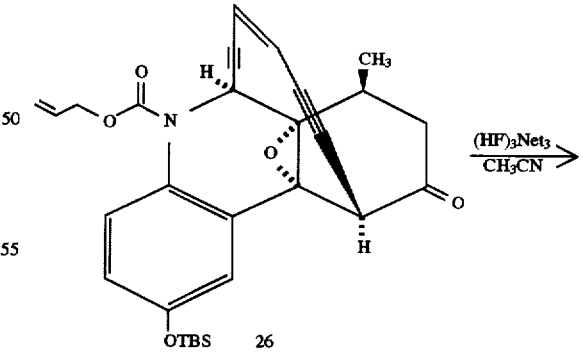

Reaction 35:

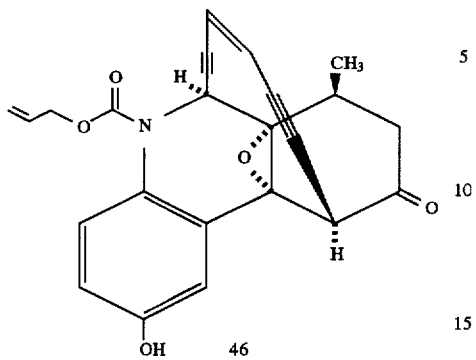

Allyl(6S,6aS,7S,10S,10aR,14Z)-7,8,9,10-Tetrahydro-2-hydroxy-7-methyl-9-oxo-6a,10a-epoxy-6,10-[3]hexene[1,5]diynophenanthridine-5(6H)-carboxylate (46)

A solution of allyl(6S,6aS,7S,10S,10aR,14Z)-2-(tert-butyldimethylsiloxy)-7,8,9,10-tetrahydro-7-methyl-9-oxo-6a,10a-epoxy-6,10-[3]hexene[1,5]diynophenanthridine-5(6H)-carboxylate (28, 140 mg, 0.27 mmol, 1 equiv) in acetonitrile (5 mL) was treated with triethylamine trihydrofluoride (0.40 mL, 2.5 mmol, 9.5 equiv), and the resulting solution was stirred at 23° C. for 2 h. The reaction mixture was partitioned between saturated aqueous sodium bicarbonate solution (100 mL) and dichloromethane (100 mL). The aqueous layer was separated and extracted further with dichloromethane (30 mL). The combined organic layers were dried over sodium sulfate and then were concentrated. Flash column chromatography (40% ethyl acetate in hexanes) of the residue provided Allyl(6S,6aS,7S,10S,10aR,14Z)-7,8,9,10-tetrahydro-2-hydroxy-7-methyl-9-oxo-6a,10a-epoxy-6,10-[3]hexene[1,5]diynophenanthridine-5(6H)-carboxylate (46) as a clear, colorless oil (104 mg, 95%).

Reaction 36:

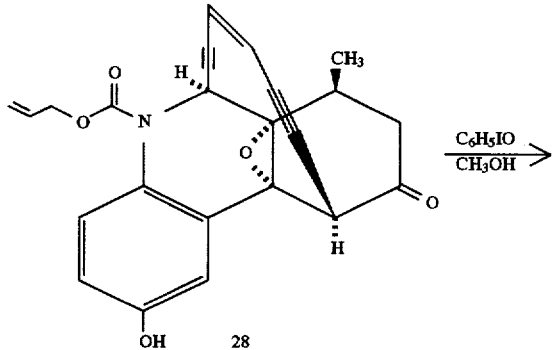

Reaction 36:

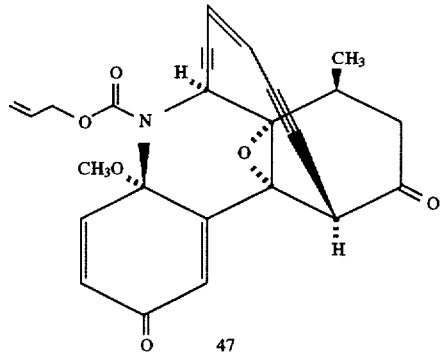

Allyl(4aS,6S,6aS,7S,10S,10aR,14Z)-2,4a,7,8,9,10-Hexahydro-4a-methoxy-7-methyl-2,9-dioxo-6a,10a-epoxy-6,10-[3]hexene[1,5]diyno-phenanthridine-5(6H)-carboxylate (47)

A solution of allyl(6S,6aS,7S,10S,10aR,14Z)-7,8,9,10-tetrahydro-2-hydroxy-7-methyl-9-oxo-6a,10a-epoxy-6,10-[3]hexene[1,5]diynophenanthridine-5(6H)-carboxylate (46, 104 mg, 0.26 mmol, 1 equiv) in methanol (30 mL) was treated with iodosobenzene (172 mg, 0.78 mmol, 3.0 equiv), and the resulting solution was stirred at 23° C. for 30 min. The reaction mixture was partitioned between saturated aqueous sodium thiosulfate solution (100 mL) and dichloromethane (100 mL). The aqueous layer was separated and extracted further with three 30-mL portions of dichloromethane. The combined organic layers were extracted with saturated aqueous sodium thiosulfate solution (100 mL), were dried over sodium sulfate, and then were concentrated. Flash column chromatography (20% ethyl acetate in hexanes) of the residue afforded allyl(4aS,6S,6aS,7S,10S,10aR,4Z)-2,4a,7,8,9,10-hexahydro-4a-methoxy-7-methyl-2,9-dioxo-6a,10a-epoxy-6,10-[3]hexene[1,5]diynophenanthridine-5(6H)-carboxylate (47) as a clear, colorless oil (69 mg, 63%).

Reaction 37:

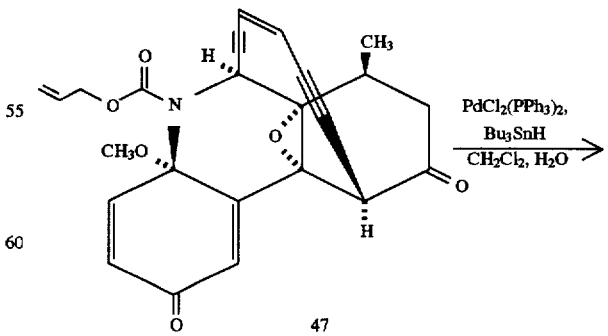

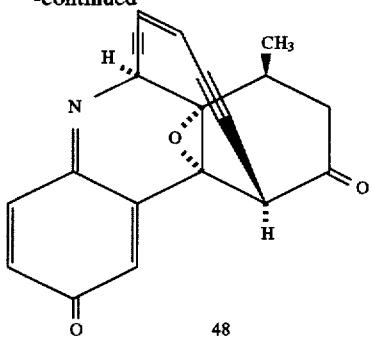

(6S,6aS,7S,10S,10aR,14Z)-7,8-Dihydro-7-methyl-6a,10a-epoxy-6,10-[3]hexene[1,5]diynophenanthridine-2,9(6H,10H)-dione (48)

To a solution of allyl(4aS,6S,6aS,7S10S,10aR,14Z)-2,4a,7,8,9,10-hexahydro-4a-methoxy-7-methyl-2,9-dioxo-6a,10a-epoxy-6,1 0-[3]hexene[1,5]diynophenanthridine-5(6H)-carboxylate (47, 40 mg, 0.093 mmol, 1 equiv) in dichloromethane (25 mL) was added water (0.50 mL), followed by bis(triphenylphosphine)palladium(II)chloride (13 mg, 0.019 mmol, 0.2 equiv). The resulting yellow, biphasic mixture was treated with tributyltin hydride (25 mL, 0.093 mmol, 1.0 equiv), added in five 5-mL aliquots over a period of 10 min, and the reaction mixture was stirred at 23° C. for 5 min. Concentration of the reaction mixture to a volume of approximately 5 mL, followed immediately by flash column chromatography (20% ethyl acetate in hexanes) afforded (6S,6aS,7S,10S,10aR,14Z)-7,8-dihydro-7-methyl-6a,10a-epoxy-6,10-[3]hexene[1,5]-diynophenanthridine-2,9(6H,10H)-dione (48) as a clear, yellow oil (8 mg, 27%).

Reaction 38:

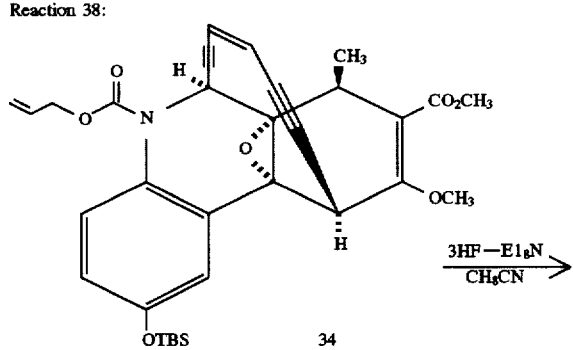

5-Allyl Methyl(6S,6aS,7S,10R,10aR,14Z)-7,10-Dihydro-2-hydroxy-9-methoxy-7-methyl-6a,10a-epoxy-6,10-[3]hexene[1,5]diynophenanthridine-5,8(6H)-dicarboxylate (49)

Triethylamine trihydrofluoride (0.20 mL, 1.2 mmol, 10 equiv) was added to a solution of 5-allyl methyl(6S,6aS,7S,10R,10aR,14Z)-2-(tert-butyldimethylsiloxy)-7,10-dihydro-9-methoxy-7-methyl-6a,10a-epoxy-6,10-[3]hexene[1,5]diynophenanthridine-5,8(6H)-dicarboxylate (34, 70 mg, 0.12 mmol, 1 equiv) in acetonitrile (8 mL) at 23° C. The reaction mixture was stirred at 23° C. for 2 h, then was partitioned between saturated aqueous sodium bicarbonate solution (70 mL) and ethyl acetate (30 mL). The aqueous layer was separated and extracted further with ethyl acetate (30 mL). The combined organic layers were dried over sodium sulfate and were concentrated. The residue was purified by flash column chromatography (40% ethyl acetate in hexanes initially, then 60% ethyl acetate in hexanes) to afford 5-allyl methyl(6S,6aS,7S,10R,10aR,14Z)-7,10-dihydro-2-hydroxy-9-methoxy-7-methyl-6a,10a-epoxy-6,10-[3]hexene[1,5]diynophenanthridine-5,8(6H)-dicarboxylate (49) as a light yellow oil (56 mg, 100%).

Reaction 39:

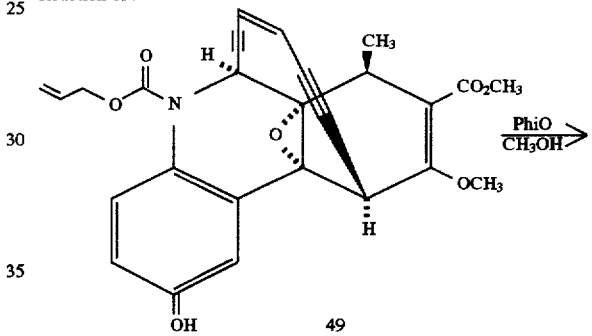

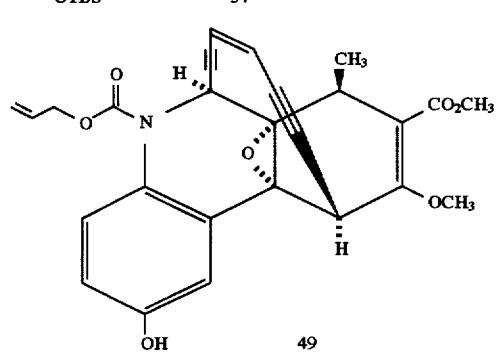

5-Allyl Methyl(4aS,6S,6aS,7S,10R,10aR,14Z)-2,4a,7,10-Tetrahydro-4a,9-dimethoxy-7-methyl-2-oxo-6a,10a-epoxy-6,10-[3]hexene[1,5]diynophenanthridine-5,8(6H)-dicarboxylate (50)

Iodosobenzene (63 mg, 0.29 mmol, 1.2 equiv) was added to a solution of 5-allyl methyl(6S,6aS,7S,10R,10aR,14Z)-7,10-dihydro-2-hydroxy-9-methoxy-7-methyl-6a,10a-epoxy-6,10-[3]hexene[1,5]diynophenanthridine-5,8(6H)-dicarboxylate (49, 115 mg, 0.243 mmol, 1 equiv) in dry methanol (10 mL) at 23° C. The reaction mixture was stirred at 23° C. for 15 min. The product solution was then partitioned between 1:1 saturated aqueous sodium bicarbonate solution:saturated aqueous sodium thiosulfate solution (70 mL), saturated aqueous sodium chloride solution (25 mL), and ethyl acetate (25 mL). The aqueous layer was separated and extracted further with ethyl acetate (2×25 mL). The combined organic layers were dried over sodium sulfate and were concentrated. The residue was purified by flash column chromatography (10% hexanes in dichloromethane initially, then 20% ethyl acetate in dichloromethane) to give 5-allyl methyl(4aS,6S,6aS,7S,10R,10aR,14Z)-2,4a,7,10-tetrahydro-4a,9-dimethoxy-7-methyl-2-oxo-6a,10a-epoxy-6,10-[3]hexene[1,5]diynophenanthridine-5,8(6H)-dicarboxylate (50) as a light yellow oil (97 mg, 80%).

Reaction 40:

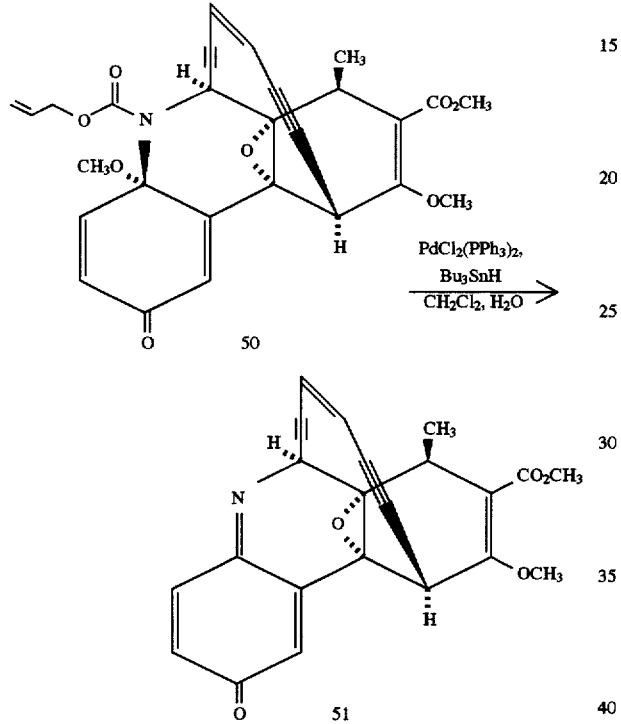

Methyl(6S,6aS,7S,10R,10aR,14Z)-2,6,7,10-Tetrahydro-9-methoxy-7-methyl-2-oxo-6a,10a-epoxy-6,10-[3]hexene[1,5]diynophenanthridine-8-carboxylate (51)

Tributyltin hydride (44 µL, 0.16 mmol, 1.1 equiv) was injected into a deoxygenated suspension of 5-allyl methyl (4aS,6S,6aS,7S,10R,10aR,14Z)-2,4a,7,10-tetrahydro-4a,9-dimethoxy-7-methyl-2-oxo-6a,10a-epoxy-6,10-[3 ]hexene [1,5]diynophenanthridine-5,8(6H)-dicarboxylate (50, 76 mg, 0.15 mmol, 1 equiv), bistriphenylphosphinepalladium (II) chloride (60 mg, 0.85 mmol, 0.57 equiv) and water (50 µL) in dichloromethane (8 mL) at 23° C. The reaction mixture was stirred for 15 min at 23° C., then was loaded directly onto a column of solvated (20% ethyl acetate in hexanes) flash-grade silica gel. Elution (20% ethyl acetate in hexanes initially, then 40% ethyl acetate in hexanes) provided methyl(6S,6aS,7S,10R,10aR,14Z)-2,6,7,10-tetrahydro-9-methoxy-7-methyl-2-oxo-6a,10a-epoxy-6,10-[3]hexene[1,5]diynophenanthridine-8-carboxylate (51) as a yellow oil (45 mg, 77%).

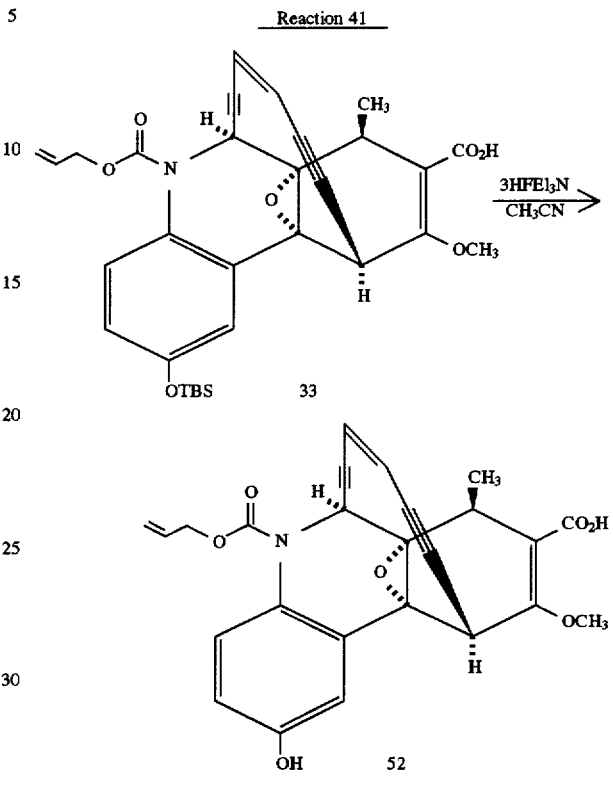

5-Allyl Hydrogen(6S,6aS,7S,10R,10aR,14Z)-7,10-Dihydro-2-hydroxy-9-methoxy-7-methyl-6a,10a-epoxy-6,10-[3]hexene[1,5]diynophenanthridine-5,8 (6H)-dicarboxylate (52)

Triethylamine trihydrofluoride (0.50 mL, 3.1 mmol, 4.5 equiv) was added to a solution of 5-allyl hydrogen(6S,6aS,7S,10R,10aR,14Z)-2-(tert-butyldimethylsiloxy)-7,10-dihydro-9-methoxy-7-methyl-6a,10a-epoxy-6,10-[3]hexene [1,5]diynophenanthridine-5,8(6H)-dicarboxylate (33, 173 mg, 0.320 mmol, 1 equiv) in acetonitrile (10 mL). The reaction mixture was stirred at 23° C. for 2 h, then was partitioned between saturated aqueous sodium bicarbonate solution (75 mL) and ethyl acetate (70 mL). The aqueous layer was separated and extracted further with ethyl acetate (70 mL). The combined organic layers were dried over sodium sulfate and were concentrated. The residue was purified by flash column chromatography (ethyl acetate initially, then 10% methanol in ethyl acetate) to provide 5-allyl hydrogen(6S,6aS,7S,10R,10aR,14Z)-7,10-dihydro-2-hydroxy-9-methoxy-7-methyl-6a,10a-epoxy-6,10-[3] hexene[1,5]diynophenanthridine-5,8(6H)-dicarboxylate (52) as a viscous, light yellow oil (118 mg, 85%).

Reaction 42:

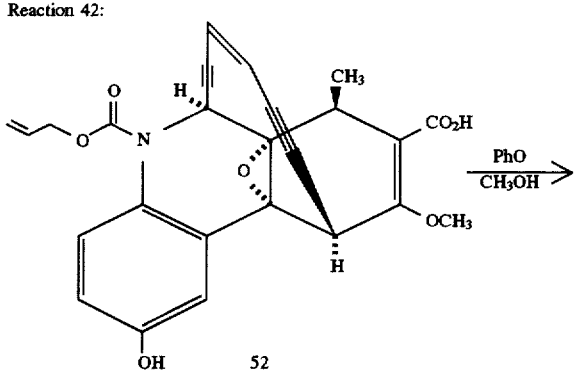

5-Allyl Hydrogen(4aS,6S,6aS,7S,10R,10aR,14Z)-2,
4a,7,10-Tetrahydro-4a,9-dimethoxy-7-methyl-2-oxo-
6a,10a-epoxy-6,10-[3]hexene[1,5]
diynophenanthridine-5,8(6H)-dicarboxylate (53)

Iodosobenzene (40 mg, 0.18 mmol, 1.1 equiv) was added to a solution of 5-allyl hydrogen(6S,6aS,7S,10R,10aR,14Z)-7,10-dihydro-2-hydroxy-9-methoxy-7-methyl-6a,10a-epoxy-6,10-[3]hexene[1,5]diynophenanthridine-5,8(6H)-dicarboxylate (52, 75 mg, 0.16 mmol, 1 equiv) in dry methanol (8 mL) at 23° C. The reaction mixture was stirred at 23° C. for 10 min. The product solution was concentrated to half the original volume in vacuo and the concentrate was partitioned between 1:1:1 saturated aqueous sodium bicarbonate solution:saturated aqueous sodium thiosulfate solution:saturated aqueous sodium chloride solution (60 mL) and ethyl acetate (30 mL). The aqueous layer was separated and extracted further with ethyl acetate (30 mL), then was acidified with aqueous hydrochloric acid solution (1% v/v, 30 mL). The acidified aqueous layer was extracted with ethyl acetate (2×40 mL). The combined organic layers were dried over sodium sulfate and were concentrated. The residue was purified by flash column chromatography (50% hexanes in ethyl acetate initially, grading to 100% ethyl acetate, and finishing with 10% methanol in ethyl acetate) to give 5-allyl hydrogen(4aS,6S,6aS,7S,10R,10aR,14Z)-2,4a,7,10-tetrahydro-4a,9-dimethoxy-7-methyl-2-oxo-6a,10a-epoxy-6,10-[3]hexene-[1,5]diynophenanthridine-5,8(6H)-dicarboxylate (53) as a viscous light yellow oil, which solidified to afford an off-white solid when concentrated from benzene (71 mg, 89%).

Reaction 43:

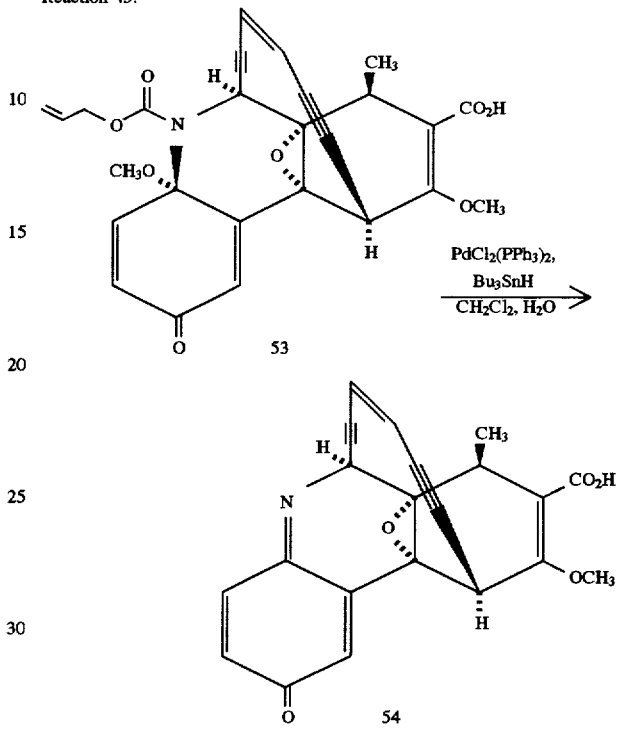

(6S,6aS,7S,10R,10aR,14Z)-2,6,7,10-Tetrahydro-9-methoxy-7-methyl2-oxo -6a,10a-epoxy-6,10-[3]-hexene[1,5]diynophenanthridine-8-carboxylic acid (54)

Tributyltin hydride (18 μL, 0.067 mmol, 0.99 equiv) was injected into a deoxygenated suspension of 5-allyl hydrogen (4aS,6S,6aS,7S,10R,10aR,14Z)-2,4a,7,10-tetrahydro-4a,9-dimethoxy-7-methyl-2-oxo-6a,10a-epoxy-6,10-[3]hexene [1,5]diynophenanthridine-5,8(6H)-dicarboxylate (53, 76 mg, 0.15 mmol, 1 equiv), bistriphenylphosphinepalladium (II) chloride (25 mg, 0.36 mmol, 0.53 equiv) and water (20 μL) in dichloromethane (5 mL) at 23° C. The reaction mixture was stirred for 15 min at 23° C., then was concentrated in vacuo. The residue was purified by flash column chromatography (40% ethyl acetate in hexanes initially, grading to 100% ethyl acetate, and finishing with 10% methanol in ethyl acetate) to afford separately (6S,6aS,7S,10R,10aR,14Z)-2,6,7,10-tetrahydro-9-methoxy-7-methyl-2-oxo-6a,10a-epoxy-6,10-[3]hexene[1,5] diynophenanthridine-8-carboxylic acid (54, ca. 75% purity) as a viscous yellow oil (7 mg, corrected yield: 21%) as well as recovered starting material (10 mg, 30%).

Reaction 44:

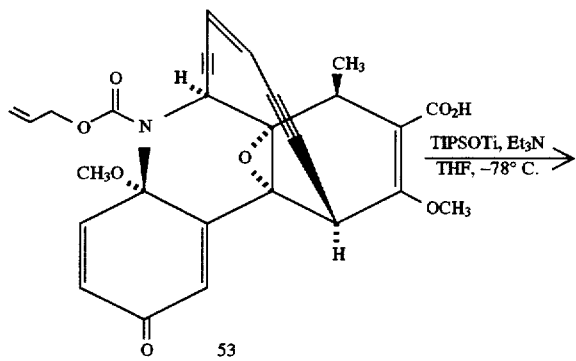

5-Allyl Triisopropylsilyl(4aS,6S,6aS,7S,10R,10aR, 14Z)-2,4a,7,10-Tetrahydro-4a,9-dimethoxy-7-methyl-2-oxo-6a,10a-epoxy-6,10-[3]hexene[1,5] diynophenanthridine-5,8(6H)-dicarboxylate (55)

Triisopropylsilyl trifluoromethanesulfonate (50 μL, 0.19 mmol, 2.3 equiv) was added to a solution of 5-allyl hydrogen (4a,6S,6aS,7S,10R,10aR,14Z)-2,4a,7,10-tetrahydro-4a,9-dimethoxy-7-methyl-2-oxo-6a,10a-epoxy-6,10-[3]hexene [1,5]diynophenanthridine-5,8 (6H)-dicarboxylate (53, 40 mg, 0.082 mmol, 1 equiv) and triethylamine (60 μL, 0.43 mmol, 5.3 equiv) in tetrahydrofuran (5 mL) at −78° C. The reaction mixture was transferred to an ice bath and was stirred for 10 min at 0° C. The product solution was partioned between saturated aqueous sodium bicarbonate solution and ethyl acetate (20 mL). The aqueous layer was separated and extracted further with ethyl acetate (20 mL). The combined organic layers were dried over sodium sulfate and were concentrated. The residue was purified by flash column chromatography (30% ethyl acetate in hexanes) to provide 5-allyl triisopropylsilyl(4aS,6S,6aS,7S,10R,10aR, 14Z)-2,4a,7,10-tetrahydro-4a,9-dimethoxy-7-methyl-2-oxo-6a,10a-epoxy-6,10-[3]hexene[1,5]diynophenanthridine-5,8 (6H)-dicarboxylate (55) as a colorless oil (45 mg, 85%).

Reaction 45:

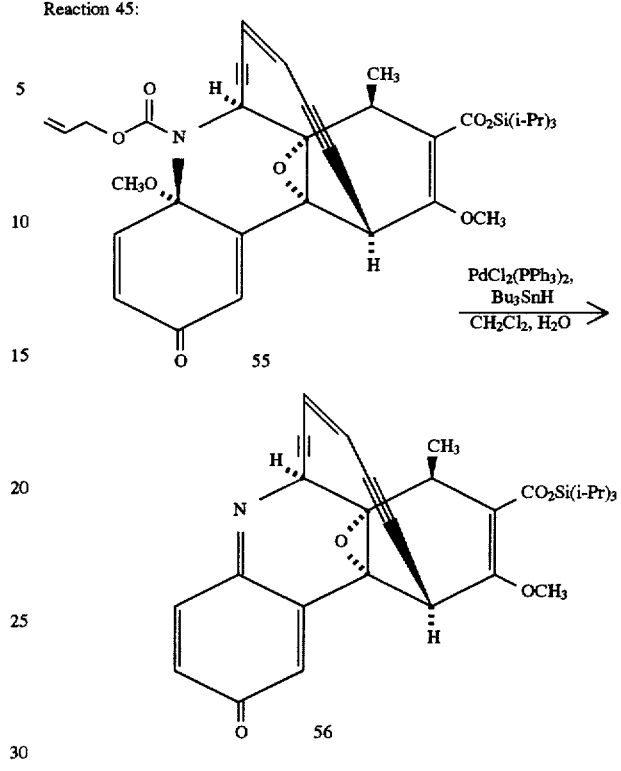

Triisopropylsilyl(6S,6aS,7S,10R,10aR,14Z)-2,6,7, 10-Tetrahydro-9-methoxy-7-methyl-2-oxo-6a,10a-epoxy-6,10-[3]hexene[1,5]diynophenanthridine-8-carboxylate (56)

Tributyltin hydride (3.0 μL, 0.011 mmol, 1 equiv) was injected into a deoxygenated suspension of 5-allyl triisopropylsilyl(4aS,6S,6aS,7S,10R,10aR,14Z)-2,4a,7,10-tetrahydro-4a,9-dimethoxy-7-methyl-2-oxo-6a,10a-epoxy-6,10 -[3]hexene[1,5]diynophenanthridine-5,8(6H)-dicarboxylate (55, 7.0 mg, 0.011 mmol, 1 equiv), bistriphenylphosphinepalladium(II) chloride (5.0 mg, 0.0071 mmol, 0.39 equiv) and water (20 μL) in dichloromethane (4 mL) at 23° C. The reaction mixture was stirred for 15 min at 23° C., then was loaded directly onto a column of solvated (20% ethyl acetate in hexanes) flash-grade silica gel. Elution (20% ethyl acetate in hexanes initially, then 40% ethyl acetate in hexanes) provided triisopropylsilyl(6S,6aS, 7S,10R,10aR,14Z)-2,6,7,10-tetrahydro-9-methoxy-7-methyl-2-oxo-6a,10a-epoxy-6,10-[3]hexene[1,5] diynophenanthridine-8-carboxylate (56) as a yellow oil (3.4 mg, 60%).

Example 3

Preparation of Anthraquinone Dynemicin Analogs

A wide variety of anthraquinone dynemicin analogs were generated using the quinone imine dynemicin analogs of Example 2. Reactions 46 to 71 generated some of the possible anthraquinone structures.

Reaction 46:

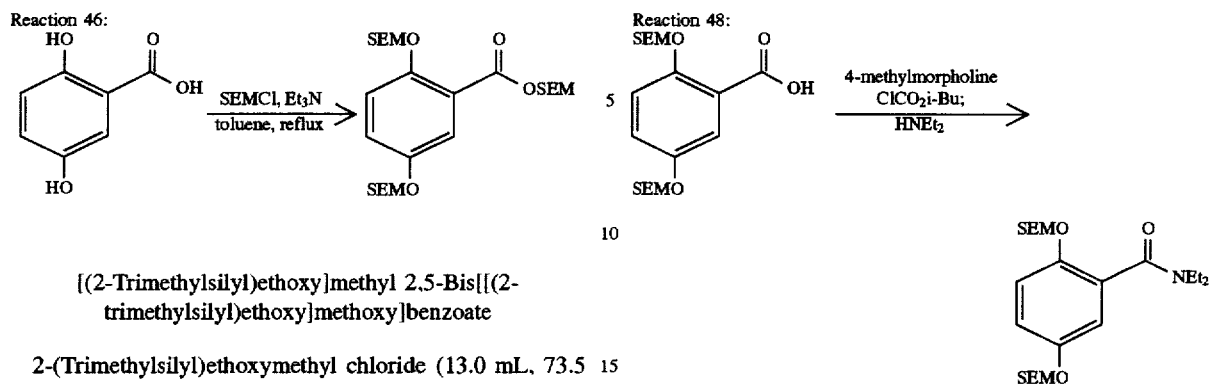

[(2-Trimethylsilyl)ethoxy]methyl 2,5-Bis[[(2-trimethylsilyl)ethoxy]methoxy]benzoate 2-(Trimethylsilyl)ethoxymethyl chloride (13.0 mL, 73.5 mmol, 5.07 equiv) was added over 5 min to a suspension of 2,5-dihydroxybenzoic acid (2.23 g, 14.5 mmol, 1 equiv) and triethylamine (12.0 mL, 86.1 mmol, 5.94 equiv) in toluene (70 mL) at 23° C. The ensuing reaction was sufficiently exothermic to bring the suspension to a gentle reflux over a period of 30 min. After 1 h, external heating was applied and the suspension was heated at reflux for 16 hours, then was cooled to 23° C. The product was partitioned between half-saturated aqueous sodium chloride solution (200 mL) and dichloromethane (100 mL). The aqueous layer was separated and extracted further with dichloromethane (2×100 mL). The combined organic layers were dried over sodium sulfate and were concentrated. The residue was purified by flash column chromatography (10% ethyl acetate in hexanes) to provide [(2-trimethylsilyl)ethoxy]methyl 2,5-bis[[(2-trimethylsilyl)-ethoxy]methoxy]benzoate as a colorless oil (7.18 g, 91%).

Reaction 47:

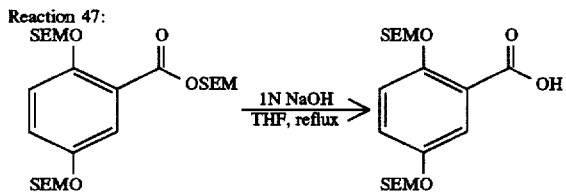

2,5-Bis[[(2-trimethylsilyl)ethoxy]methoxy]benzoic acid

A biphasic solution of [(2-trimethylsilyl)ethoxy]methyl 2,5-bis[[(2-trimethylsilyl)-ethoxy]methoxy]benzoate (7.18 g, 13.2 mmol, 1 equiv) in tetrahydrofuran (80 mL) and 1.0N aqueous sodium hydroxide solution (80 mL, 80 mmol, 6.1 equiv) was heated at reflux for 24 h. The product solution was cooled to 23° C., then was diluted with aqueous hydrochloric acid solution (1% v/v, 300 mL). The aqueous layer was further acidified to pH 1 by the addition of concentrated aqueous hydrochloric acid solution. The acidified aqueous phase was extracted with dichloromethane (2×300 mL). The combined organic layers were dried over sodium sulfate and were concentrated. The residue was purified by flash column chromatography (40% ethyl acetate in hexanes initially, grading to 100% ethyl acetate) to provide 2,5-bis[[(2-trimethylsilyl)ethoxy]methoxy]benzoic acid as a colorless oil (5.44, 100%). Because of the propensity of the ortho SEM ether to migrate to the carboxylic acid, the purified product was used immediately in the next step in the sequence.

Reaction 48:

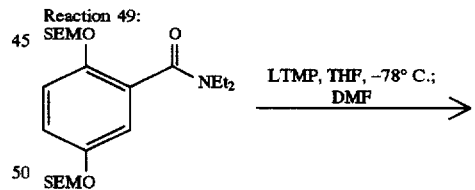

2,5-Bis[[(2-trimethylsilyl)ethoxy]methoxy]benzoic Acid N,N-Diethylamide

Isobutyl chloroformate (8.0 mL, 62 mmol, 3.7 equiv) was added to a solution of 4-methylmorpholine (7.0 mL, 64 mmol, 3.9 equiv) and 2,5-bis[[(2-trimethylsilyl)ethoxy]-methoxy]benzoic acid (6.85 g, 16.5 mmol, 1 equiv) in tetrahydrofuran (150 mL) at 0° C., producing a white precipitate. The reaction mixture was swirled manually at 0° C. for 20 min. Diethylamine (20.0 mL, 193 mmol, 11.7 equiv) was added to the suspension, and the mixture was swirled manually at 0° C. for 5 min, producing a solid mass. Additional tetrahydrofuran (100 mL) was added to the mass, followed by diethylamine (10.0 mL, 96.7 mmol, 5.58 equiv). The resultant suspension was swirled manually as it was allowed to warm to 23° C. The product suspension was partitioned between half-saturated aqueous sodium chloride solution (200 mL) and ethyl acetate (200 mL). The aqueous layer was separated and extracted further with ethyl acetate (200 mL). The combined organic layers were dried over sodium sulfate and were concentrated. The residue was purified by flash column chromatography (20% ethyl acetate in hexanes initially, then 40% ethyl acetate in hexanes) to give 2,5-bis[[(2-trimethylsilyl)ethoxy]methoxy]benzoic acid N,N-diethylamide as a light yellow oil (5.89 g, 76%).

Reaction 49:

SEMO
<br>
[structure: 2,5-bis-SEMO benzoic acid N,N-diethylamide with LTMP, THF, -78° C.; DMF arrow to product]

[product structure: 2-Formyl-3,6-bis-SEMO benzoic acid N,N-diethylamide]

2-Formyl-3,6-bis[(2-trimethylsilyl)ethoxymethoxy]benzoic Acid N,N-Diethylamide A solution of 2,5-bis[[(2-trimethylsilyl)ethoxy]methoxy]benzoic acid N,N-diethylamide (1.50 g, 3.19 mmol, 1 equiv) in tetrahydrofuran (5 mL) at 23° C. was transferred via cannula to a solution of lithium 2,2,6,6-tetramethylpiperidide in tetrahydrofuran (0.329M, 13.6 mL, 4.48 mmol, 1.40 equiv) at −78° C. The reaction mixture was stirred at −78° C. for 2 h. N,N-Dimethylformamide (1.50 mL, 19.4 mmol, 6.07 equiv) was added, and the reaction mixture was transferred to an ice bath. After 10 min, the ice bath was removed and the reaction mixture was allowed to warm to 23° C. After 1 h, the product solution was partitioned between aqueous phosphate buffer solution (pH 7, 0.05M in sodium hydrogen phosphate and 0.05M in potassium dihydrogen phosphate, 100 mL) and ethyl acetate (100 mL). The aqueous layer was separated and extracted further with ethyl acetate (100 mL). The combined organic layers were dried over sodium sulfate and were concentrated. The residue was purified by flash column chromatography (30% ethyl acetate in hexanes intially, then 40% ethyl acetate in hexanes) to provide separately 2-formyl-3,6-bis[(2-trimethylsilyl)ethoxymethoxy]benzoic acid N,N-diethylamide as a colorless oil (1.072 g, 67%) as well as recovered 2,5-bis[[(2-trimethylsilyl)ethoxy]methoxy] benzoic acid (0.305 g, 20%).

Reaction 50:

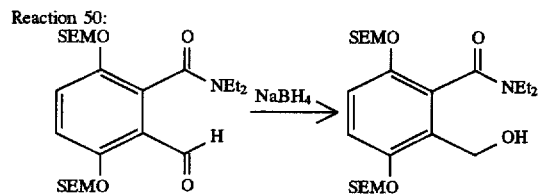

2-(Hydroxymethyl)-3,6-bis[(2-trimethylsilyl) ethoxymethoxy]benzoic Acid N,N-Diethylamide Sodium borohydride (272 mg, 7.19 mmol, 4.99 equiv) was added to a solution of 2-formyl-3,6-bis[2-trimethylsilyl) ethoxymethoxy]benzoic acid N,N diethylamide (718) mg, 1.44 mmol, 1 equiv) in absolute ethanol (15 mL) at 0° C. The reaction mixture was stirred for 3 h at 0° C., then was partitioned between half-saturated aqueous sodium chloride solution (100 mL) and ethyl acetate (70 mL). The aqueous layer was separated and extrated further with ethyl acetate (2×70 mL). The combined organic layers were dried over sodium sulfate and were concentrated. The residue was purified by flash column chromatography (50 % ethyl acetate in hexanes) to provide 2-(hydroxymethyl)-3,6-bis [trimethylsilyl)ethoxymethoxy]benzoic acid N,N diethylamide as a colorless oil (660 mg, 92%).

Reaction 51:

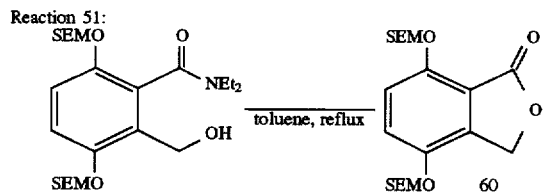

4,7-Bis[[2-(trimethylsilyl)ethoxyl]methoxy] phthialide (60)

A suspension of 2-(hydroxymethyl)-3,6-bis[(2-trimethylsilyl)ethoxy methoxy]-benzoic acid N,N diethylamide (695 mg, 1.39 mmol, 1 equiv) and potassium carbonate (10 mg, 0.07 mmol, 0.05 equiv) in 1,3,5-trimethylbenzene (30 mL) was heated at reflux for 80 min. The reaction mixture was cooled to 23° C., then was concentrated in vacuo. The residue was purified by flash column chromatography (30% ethyl acetate in hexanes) to provide 4,7-bis [[(2-(trimethylsilyl)ethoxyl]methoxy]phthalide (60) as a white solid (481 mg, 81%).

Reaction 52:

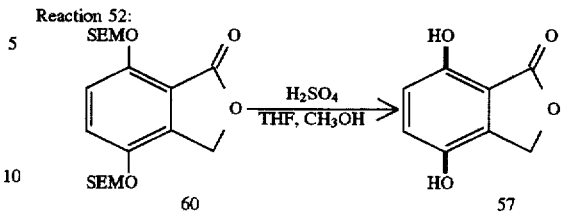

4,7-Dihydroxyphthalide (57)

A solution of concentrated sulfuric acid (4.0 mL, 75 mmol, 15 equiv) in dry methanol (50 mL) at 23° C. was added to a solution of 4,7-bis[[2-(trimethylsilyl)ethoxyl] methoxy]phthalide (60, 2.148 g, 5.034 mmol, 1 equiv) in dry methanol (50 mL) at 23° C. The reaction mixture was stirred for 2.0 h at 23° C. The product solution was partitioned carefully between saturated aqueous sodium bicarbonate solution (200 mL), saturated aqueous sodium chloride solution (150 mL), and ethyl acetate (100 mL). The aqueous layer was separated and extracted further with ethyl acetate (2×100 mL). The combined organic layers were dried over sodium sulfate and were concentrated affording the 4,7-dihydroxyphthalide (57) as an off-white solid (821 mg, 98%), which was used without further purification.

Reaction 53:

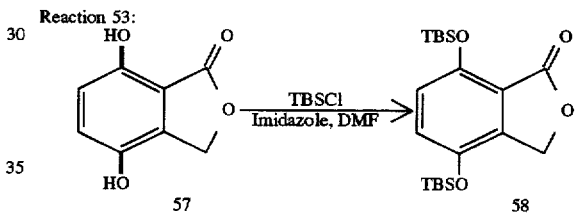

4,7-Bis(tert-butyldimethylsiloxy)phthalide (58)

tert-Butyldimethylsilyl chloride (700 mg, 4.64 mmol, 7.08 equiv) was added to a solution of 4,7-dihydroxyphthalide (57, 109 mg, 0.656 mmol, 1 equiv) and imidazole (562 mg, 8.25 mmol, 12.6 equiv) in N,N-dimethylformamide (2 mL) at 23° C. The reaction mixture was stirred at 23° C. for 20 min. The product solution was partitioned between half-saturated aqueous sodium chloride solution (75 mL) and ethyl acetate (40 mL). The aqueous layer was separated and extracted further with ethyl acetate (40 mL). The combined organic layers were dried over sodium sulfate and were concentrated. The residue was purified by flash column chromatography (10% ethyl acetate in hexanes) to provide 4,7-bis(tert-butyldimethylsiloxy) phthalide (58) as a white solid (220 mg, 85%).

Reaction 54:

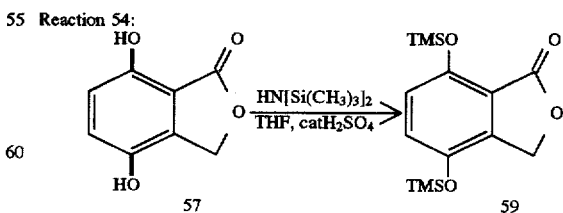

4,7-Bis(trimethylsiloxy)phthalide (59)

A suspension of 4,7-dihydroxyphthalide (57, 46 mg, 0.28 mmol, 1 equiv), hexamethyldisilazane (1.0 mL, 4.7 mmol, 17 equiv) and concentrated sulfuric acid (1.0 μL, 19 μmol, 68 μequiv) in tetrahydrofuran (2 mL) was heated at reflux for 30 min. The reaction mixture was cooled to 23° C. and was concentrated in vacuo affording 4,7-bis(trimethylsiloxy) phthalide (59) as a moisture-sensitive, colorless oil (86 mg, 100%).

Reaction 55:

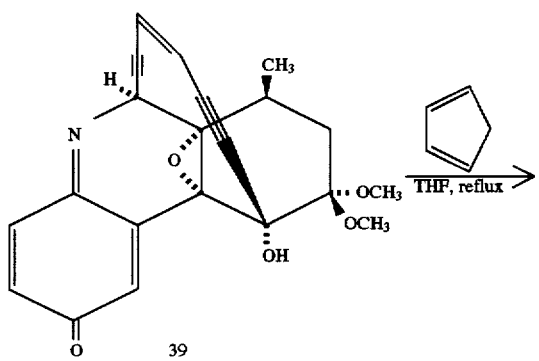

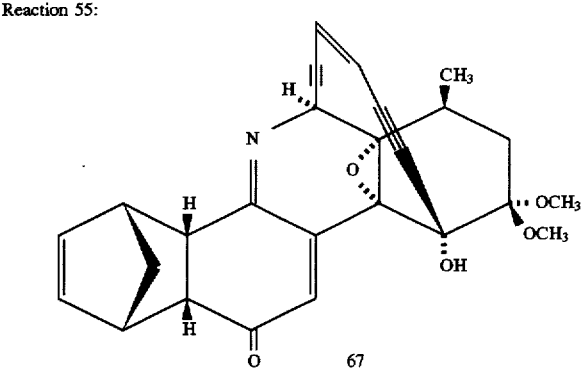

(1S,4R,4aS,6S,6aS,7S,10R,10aS,12aR,16Z)-1,4,4a, 6,7,8,9,10-Octahydro-10-hydroxy-9,9-dimethoxy-7-methyl-6a,10a-epoxy-6,10-[3]hexene[1,5]diyno-1,4-methanobenzo[c]phenanthridin-12(12aH)-one (67)

A solution of (6S,6aS,7S,10R,10aS,14Z)-7,8,9,10-tetrahydro-10-hydroxy-3,9-dimethoxy-7-methyl-6a,10a-epoxy-6,10-[3]hexene[1,5]-diynophenanthridin-2(6H)-one (39, 2.0 mg, 0.0053 mmol, 1 equiv) and cyclopentadiene (200 μL, 3.0 mmol, 570 equiv) in tetrahydrofuran (1.5 mL) was heated at reflux for 45 min. The product solution was cooled to 23° C., then was concentrated in vacuo. The residue was purified by flash column chromatography (50% ethyl acetate in hexanes initially, then 60% ethyl acetate in hexanes) to provide (1S,4R,4aS,6S,6aS,7S,10R,10aS,12aR, 16Z)-1,4,4a,6,7,8,9,10-octahydro-10-hydroxy-9,9-dimethoxy-7-methyl-6a,10a-epoxy-6,10-[3]hexene[1,5] diyno-1,4-methanobenzo[c]phenanthridin-12(12aH)-one (67) as a colorless oil (2.0 mg, 90%).

Reaction 56:

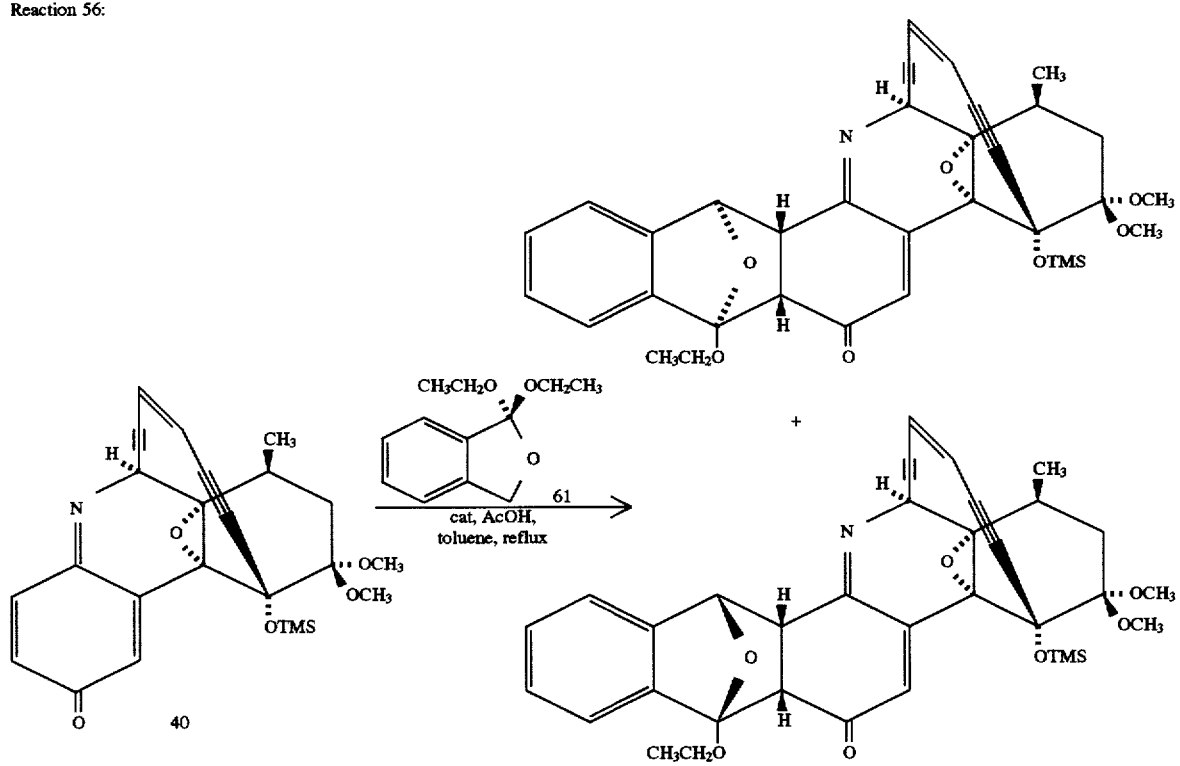

73

(1S,4R,4aS,6aR,7S,12R,12aS,14S,14aS,18Z)-7-
Ethoxy-1,2,3,4,7,12,12a,14-octahydro-3,3-
dimethoxy-1-methyl-4-trimethylsilyloxy-4a,14a:7,
12-diepoxy-4,14-[3]hexene[1,5]diynonaphtho[2,3-c]
phenanthridin-6(6aH)-one A deoxygenated solution of (6S,6aS,7S,10R,10aR,14Z)-7,8,9,10-tetrahydro-9,9-dimethoxy-7-methyl-10-(trimethylsiloxy)-6a,10a-epoxy-6,10-[3]hexene[1,5]diynophenan-thridin-2(6h)-one (40, 5.0 mg, 0.011 mmol, 1 equiv), 1,1-diethoxyphthalan (61, 50 mg, 0.24 mmol, 22 equiv) and glacial acetic acid (1.0 µL, 0.017 mmol, 1.6 equiv) in toluene (2 mL) was heated at reflux for 20 min. Heating was discontinued and glacial acetic acid (1.0 µL, 0.017 mmol, 1.6 equiv) was added to the warm reaction mixture. The reaction mixture was heated at reflux for 15 min, then was cooled to 23° C. and was concentrated in vacuo. The residue was purified twice by flash column chromatography (first column: 10% ethyl acetate in dichloromethane; second column: 40% ethyl acetate in hexanes) to provide separately (1S,4R,4aS,6aR,7S,12R,12aS,14S,14aS,18Z)-7-ethoxy-1,2,3,4,7,12,12a,14-octahydro-3,3-dimethoxy-1-methyl-4-trimethylsilyloxy-4a,14a:7,12-diepoxy-4,14-[3]hexene[1,5]diynonaphtho[2,3-c]phenanthridin-6(6aH)-one as a colorless oil (2.0 mg, 30%) as well as (1S,4R,4aS,6aR,7R,12S,12aS,14S,14aS,18Z)-7-ethoxy-1,2,3,4,7,12,12a,14-octahydro-3,3-dimethoxy-1-methyl-4-trimethylsilyloxy-4a,14a:7,12-diepoxy-4,14-[3]hexene[1,5]diynonaphtho[2,3-c]phenanthridin-6(6aH)-one as colorless oil (2.0 mg, 30%).

74

(1S,4R,4aS,14S,14aS,18Z)-1,2,3,4,7,13,14-Hexahydro-6-hydroxy-3,3-dimethoxy-1-methyl-4-trimethylsilyloxy-4a,14a-epoxy-4,14-[3]hexene[1,5]diynonaphtho[2,3-c]phenanthridine-7,12-dione Pyridinium chlorochromate (4 mg, 0.02 mmol, 11 equiv) was added to a solution of (1S,4R,4aS,6aR,7S,12R,12aS,14S,14aS,18Z)-7-ethoxy-1,2,3,4,7,12,12a,14-octahydro-3,3-dimethoxy-1-methyl-4-trimethylsilyloxy-4a,14a:7,12-diepoxy-4,14-[3]hexene[1,5]diynonaphtho[2,3-c]phenanthridin-6(6aH)-one (1.0 mg, 0.0016 mmol, 1 equiv) in dichloromethane (0.5 mL) at 23° C. The reaction mixture was stirred for 10 min, then was loaded directly onto a column of solvated (20% ethyl acetate in hexanes) flash grade silica gel. Elution (20% ethyl acetate in hexanes) provided (1S,4R,4aS,14S,14aS,18Z)-1,2,3,4,7,13,14-hexahydro-6-hydroxy-3,3-dimethoxy-1-methyl-4-trimethylsilyloxy-4a,14a-epoxy-4,14-[3]hexene[1,5]diynonaphtho[2,3-c]phenanthridine-7,12-dione as a red solid (300 µg, 30%).

Reaction 57:

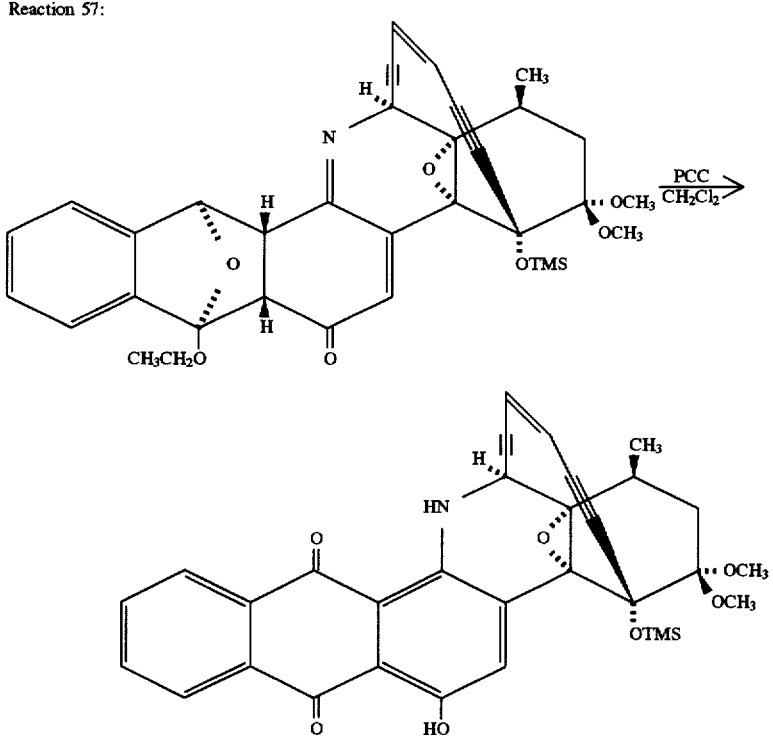

Reaction 58:

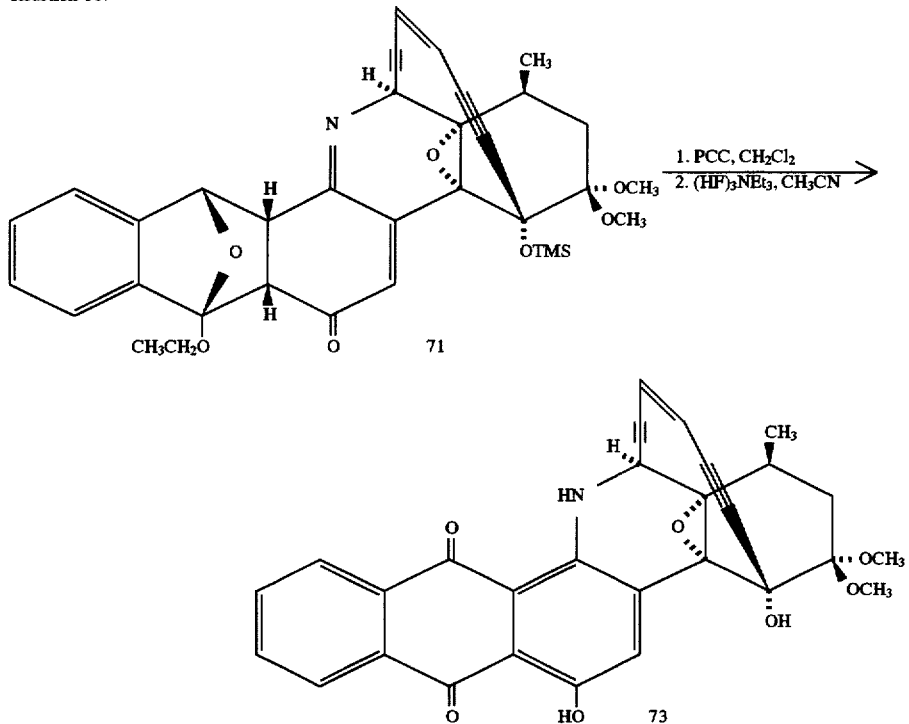

(1S,4R,4aS,14S,14aS,18Z)-1,2,3,4,13,14-Hexahydro-4,6-dihydroxy-3,3-dimethoxy-1-methyl-4a,14a-epoxy-4,14-[3]hexene[1,5]diynonaphtho[2,3-c]phenanthridine-7,12-dione (73)

A solution of (1S,4R,4aS,6aR,7R,12S,12aS,14S,14aS,18Z)-7-ethoxy-1,2,3-4,7,12,12a,14-octahydro-trimethylsiloxy-3,3-dimethoxy-1-methyl-4a,14a:7,12-diepoxy-4,14-[3]hexene[1,5]diynonaphtho[2,3-c]phenanthridin-6(6aH)-one (71, 115 mg, 0.19 mmol, 1 equiv) in dichloromethane (30 mL) was treated with pyridinium chlorochromate (390 mg, 1.88 mmol, 10 equiv), and the resulting mixture was stirred at 23° C. for 10 min, giving rise to a dark purple solution. The reaction mixture was partitioned between saturated aqueous sodium bicarbonate solution (500 mL) and dichloromethane (200 mL). The green aqueous layer was separated and the purple dichloromethane layer was extracted further with saturated aqueous sodium bicarbonate solution (300 mL). The dichloromethane layer was treated with triethylamine (1.0 mL) and then was dried over sodium sulfate. Concentration of the solution to a volume of 10 mL, followed immediately by flash column chromatography (20% ethyl acetate in hexanes), afforded a purple residue after concentration of the appropriate column fractions. The residue was dissolved in acetonitrile (5 mL) and the resulting solution was treated with triethylamine trihydrofluoride (0.61 mL, 3.8 mmol, 20 equiv). After stirring at 23° C. for 3 h, the reaction mixture was partitioned between saturated aqueous sodium bicarbonate solution (100 mL) and dichloromethane (100 mL). The organic layer was dried over sodium sulfate and then was concentrated. Flash column chromatography (20% ethyl acetate in hexanes) of the residue afforded (1S,4R,4aS,14S,14aS,18Z)-1,2,3,4,13,14-hexahydro-4,6-dihydroxy-3,3-dimethoxy-1-methyl-4a,14a-epoxy-4,14-[3]hexene[1,5]diynonaphtho[2,3-c]phenanthri-dine-7,12-dione (73) as a dark puple oil (30.0 mg, 28%).

Reaction 59:

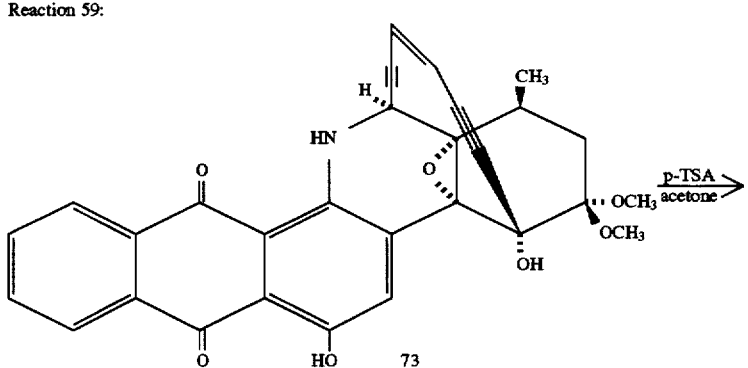

Reaction 59:

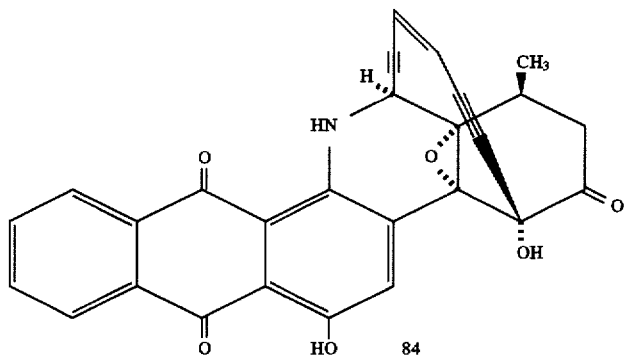

(1S,4R,4aS,14S,14aS,18Z)-1,2,13,14-Tetrahydro-4,6-dihydroxy-1-methyl-4a,14a-epoxy-4,14-[3]-hexene[1,5]diynonaphtho[2,3-c]phenan-thridine-3,7,12(4H)-trione (84)

A solution of (1S,4R,4aS,14S,14aS,18Z)-1,2,3,4,13,14-hexahydro-4,6-dihydroxy-3,3-dimethoxy-1-methyl-4a,14a-epoxy-4,14-[3]hexene[1,5]diynonaphtho[2,3-c]phenanthridine-7,12-dione (73, 4 mg, 0.007 mmol, 1 equiv) in acetone (5 mL) was treated with p-toluenesulfonic acid (50 mg, 0.26 mmol, 40 equiv), and the resulting solution was stirred at 23° C. for 2 h. The reaction mixture was partitioned between saturated aqueous sodium bicarbonate solution (50 mL) and dichloromethane (50 mL). The organic layer was dried over sodium sulfate and then was concentrated. Flash column chromatography (20% ethyl acetate in hexanes) of the residue afforded (1S,4R,4aS,14S,14aS,18Z)-1,2,13,14-tetrahydro-4,6-dihydroxy-1-methyl-4a,14a-epoxy-4,14-[3]hexene[1,5]diynonaphtho[2,3-c]phenanthridine-3,7,12H)-trione (84) as a dark purple oil (2 mg, 50%).

genated by alternately evacuating the reaction flask and flushing with argon (3×), then was heated at reflux for 20 min. The reaction mixture was cooled to 25° C., then was partitioned between saturated aqueous sodium bicarbonate solution (50 mL) and dichloromethane (50 mL). The organic layer was dried over sodium sulfate and was concentrated. Flash column chromatography (20% ethyl acetate in hexanes) of the residue afforded (1S,4S,4aR,6aR,7R,12S,12aS,14S,14aS,18Z)-7-Ethoxy-1,2,7,12,12a,14-hexahydro-1-methyl-4a,14a:7,12-diepoxy-4,14-[3]hexene[1,5]diynonaphtho[2,3-c]phenanthridine-3,6-(4H,6aH)-dione (86) as a clear, colorless oil (3 mg, 50%).

Reaction 60:

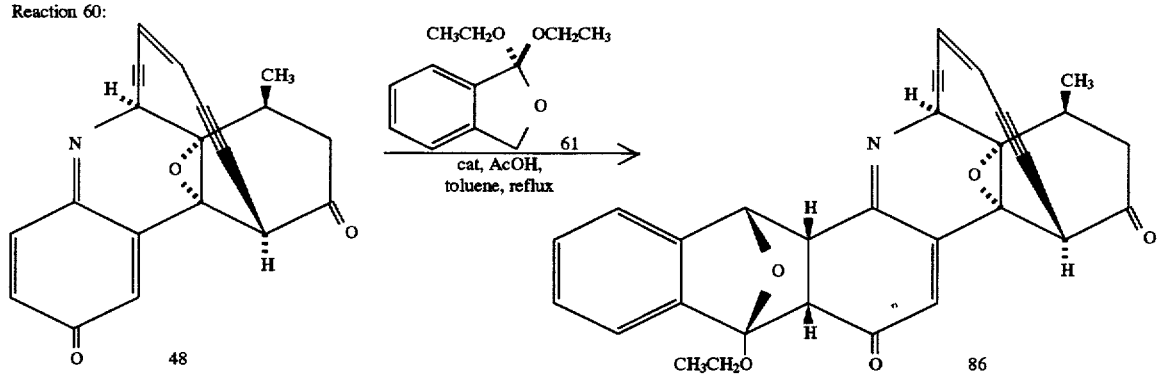

(1S,4S,4aR,6aR,7R,12S,12aS,14S,14aS,18Z)-7-Ethoxy-1,2,7,12,12a,14-hydro-1-methyl-4a,14a:7,12-diepoxy-4,14-[3]hexene[1,5]diyno-naphtho[2,3-c]phenanthridine-3,6(4H,6aH)-dione (86)

A 10-mL round bottom flask equipped with a reflux condenser was charged with (6S,6aS,7S,10S,10aR,14Z)-7,8-dihydro-7-methyl-6a,10a-epoxy-6,10-[3]hexene[1,5]-diynophenanthridine-2,9(6H,10H)-dione (48, 4 mg, 0.013 mmol, 1 equiv), toluene (3 mL), 1,1-diethoxyphthalan (61, 50 mg, 0.24 mmol, 20 equiv), and finally, acetic acid (1 mL, 0.014 mmol, 1.1 equiv). The resulting solution was deoxy- Reaction 61:

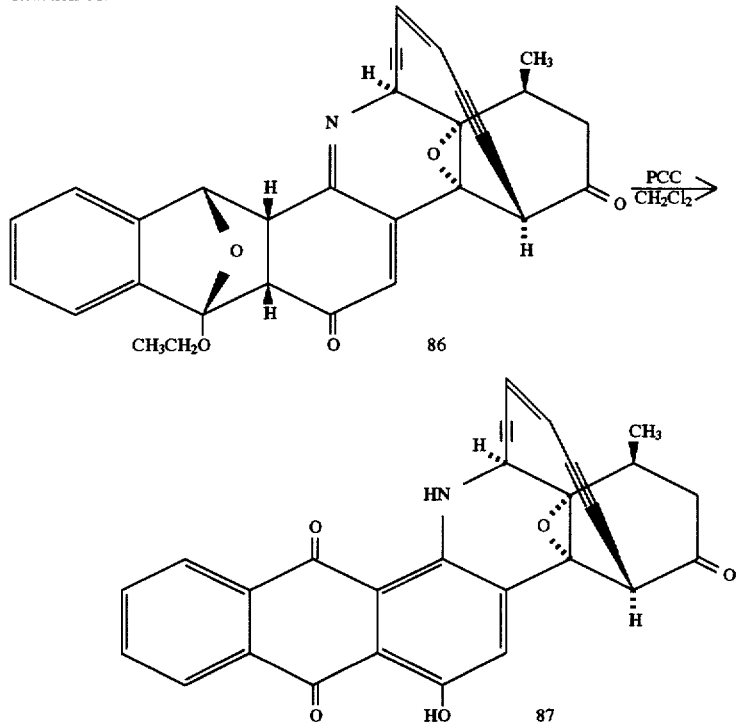

(1S,4S,4aR,14S,14aS,18Z)-1,2,13,14-Tetrahydro-6-hydroxy-1-methyl-4a,14a-epoxy-4,14-[3]hexene[1,5]diynonaphtho[2,3-c]phenanthridine-3,7,12(4H)-trione (87)

A solution of (1S,4S,4aR,6aR,7R,12S,12aS,14S,14aS,18Z)-7-ethoxy-1,2,7,12,12a,14-hexahydro-1-methyl-4a,14a:7,12-diepoxy-4,14-[3 ]hexene[1,5]diynonaphtho[2,3-c]phenanthridine-3,6(4H,6aH)-dione (86, 2 mg, 0.004 mmol, 1 equiv) in dichloromethane (3 mL) was treated with pyridinium chlorochromate (4 mg, 0.02 mmol, 5 equiv), and the resulting mixture was stirred at 23° C. for 10 min, giving rise to a dark purple solution. The reaction mixture was partitioned between saturated aqueous sodium bicarbonate solution (50 mL) and dichloromethane (20 mL). The green aqueous layer was separated and the purple dichloromethane layer was extracted further with saturated aqueous sodium bicarbonate solution (30 mL). The dichloromethane layer was treated with triethylamine (0.2 mL), then was dried over sodium sulfate. Concentration of the solution to a volume of 5 mL, followed immediately by flash column chromatography (20% ethyl acetate in hexanes), provided (1S,4S,4aR, 14S,14aS,18Z)-1,2,13,14-tetrahydro-6-hydroxy-1-methyl-4a,14a-epoxy-4,14-[3]hexene[1,5]diynonaphtho[2,3-c] phenanthridine-3,7,12(4H)-trione (87) as a dark purple film (0.2 mg, 20%).

Reaction 62:

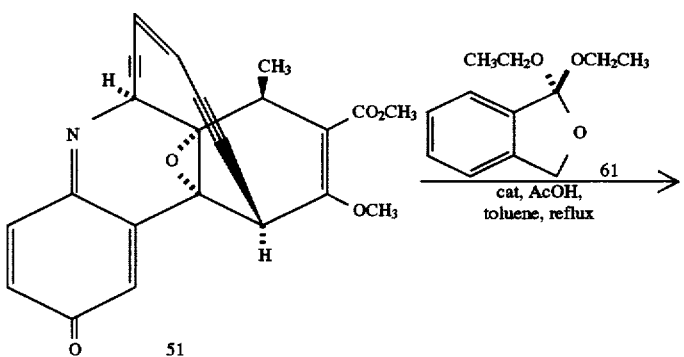

Reaction 62:

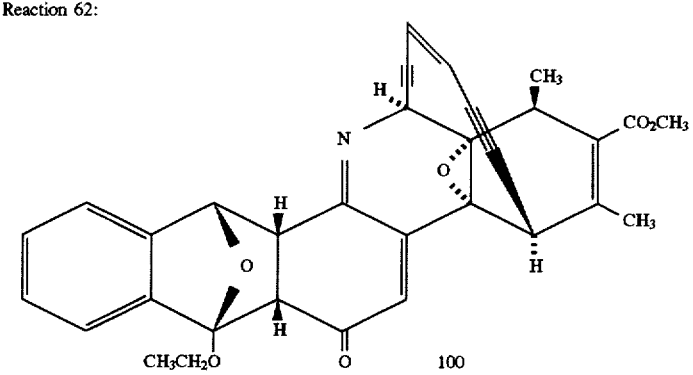

Methyl(1S,4S,4aR,6aR,7R,12S,12aS,14S,14aS,18Z)-7-ethoxy-1,2,4,7,12,12a,13,14-octahydro-3-methoxy-1-methyl-7,12-dioxo-4a,14a:7,12-diepoxy-4,14-[3]-hexene[1,5]diynonaphtho[2,3-c]phenanthridine-2-carboxylate (100)

A 10-mL round bottom flask equipped with a reflux condenser was charged with methyl(6S,6aS,7S,10R,10aR, 14Z)-2,6,7,10-tetrahydro-9-methoxy-7-methyl-2-oxo-6a,10a-epoxy-6,10-[3]hexene[1,5]diynophenanthridine-8-carboxylate (51, 17 mg, 0.045 mmol, 1 equiv), toluene (2 mL), 1,1-diethoxyphthalan (61, 47 mg, 0.23 mmol, 5 equiv), and finally, acetic acid (1 mL, 0.014 mmol, 0.4 equiv). The resulting solution was deoxygenated by alternately evacuating the reaction flask and flushing with argon (3×), then was heated at reflux for 30 min. The reaction mixture was cooled to 25° C., then was partitioned between saturated aqueous sodium bicarbonate solution (50 mL) and dichloromethane (50 mL). The organic layer was dried over sodium sulfate and was concentrated. Flash column chromatography (20% ethyl acetate in hexanes) of the residue afforded methyl(1S,4S,4aS,6aR,7R,12S,12aS,14S,14aS, 18Z)-7-ethoxy-1,2,4,7,12,12a,13,14-octahydro-3-methoxy-1-methyl-7,12-dioxo-4a,14a:7,12-diepoxy-4,14-[3]hexene [1,5]diynonaphtho[2,3-c]phenanthridine-2-carboxylate (100) as a clear, colorless oil (9 mg, 37%).

Reaction 63:

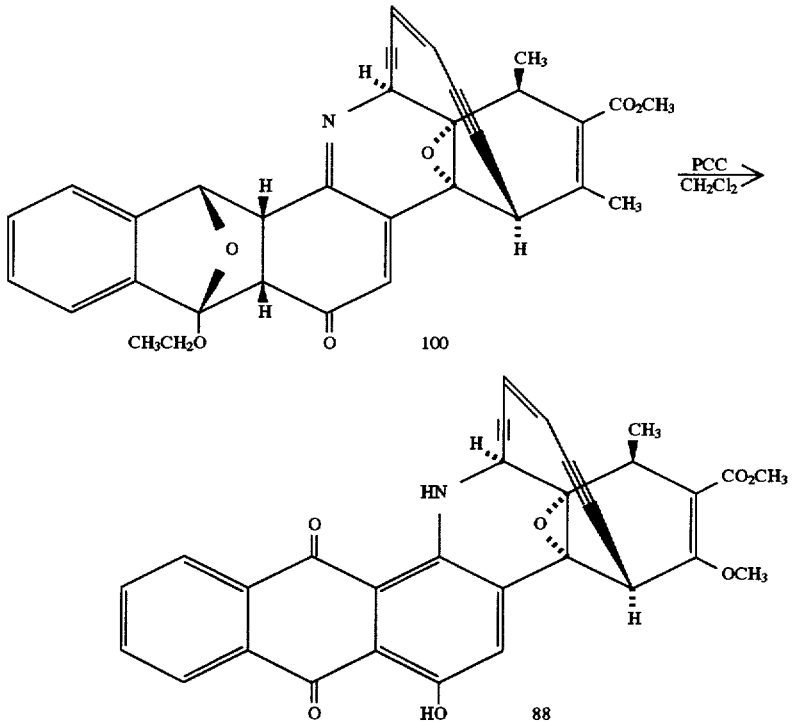

Methyl(1S,4R,4aR,14S,14aS,18Z)-1,4,7,12,13,14-Hexahydro-6-hydroxy-3-methoxy-1-methyl-7,12-dioxo-4a, 14a-epoxy-4,14-[3]hexene[1,5]diynonaphtho[2,3-c]-phenanthridine-2-carboxylate (88)

A solution of methyl(1S,4S,4aS,6aR,7R,12S,12aS,14S, 14aS,18Z)-7-epoxy-1,2,4,7,12,12a,13,14-octahydro-3-methoxy-1-methyl-7,12-dioxo-4a,14a:7,12-diepoxy-4,14-[3]hexene[1,5]diynonaphtho[2,3-c]phenanthridine-2- carboxylate (100, 7 mg, 0.013 mmol, 1 equiv) in dichloromethane (5 mL) was treated with pyridinium chlorochromate (27 mg, 0.13 mmol, 10 equiv), and the resulting mixture was stirred at 23° C. for 10 min, giving rise to a dark purple solution. The reaction mixture was partitioned between saturated aqueous sodium bicarbonate solution (50 mL) and dichloromethane (30 mL). The purple dichloromethane layer was separated and extracted further with saturated aqueous sodium bicarbonate solution (30 mL). The dichloromethane layer was treated with triethylamine (0.5 mL), then was dried over sodium sulfate. The product was isolated by reverse-phase HPLC, as follows: 20-mL aliquots of the purple product solution were concentrated and the residue from each was dissolved separately in methanol (0.5 mL). The methanolic solutions were then injected onto a Beckman Ultrasphere ODS ($C_{18}$, 5 mm) rp-HPLC column, 10×250 mm, as part of a Beckman HPLC system, flow rate 2.00 mL/min, with a linear gradient of acetonitrile:aqueous ammonium acetate buffer (10 mM, pH 6.0): 70:30 v/v acetonitrile:aqueous ammonium acetate buffer (10 mM, pH 6.0) to 100% acetonitrile over a period of 40 min. Peaks were detected by ultraviolet absorption at 250 and 540 nm with a Beckman 168 Programmable Photodiode Detector. Fractions containing product (retention time $t_R$~40 min) were collected and pooled. Acetonitrile was removed by rotary evaporation and the remaining aqueous buffer was removed by lyophilization. Methyl(1S,4R,4aR,14S,14aS,18Z)-1,4,7,12,13,14-hexahydro-6-hydroxy-3-methoxy-1-methyl-7,12-dioxo-4a,14a-epoxy-4,14-[3]hexene[1,5]diyno-naphtho[2,3-c]phenanthridine-2-carboxylate (88) was obtained as a dark purple film (1 mg, 15%).

interval of 5 min between additions. The reaction mixture became colorless upon the final addition of chlorotrimethylsilane. A solution of (6S,6aS,7S,10R,10aS,14Z)-7,8,9,10-tetrahydro-10-hydroxy-9,9-dimethoxy-7-methyl-6a,10a-epoxy-6,10-[3]hexene[1,5]-diynophenanthridin-2(6H)-one (39, 10.0 mg, 0.026 mmol, 1 equiv) in tetrahydrofuran (1 mL) at 23° C. was transferred over 5 s via cannula to the cold reaction mixture. The cooling bath was removed and the reaction mixture was heated to reflux within 2 min using a heat gun. When the reaction mixture began to boil, heating was discontinued and the flask was allowed to cool to 23° C. The product solution was partitioned between saturated aqueous sodium bicarbonate solution (5 mL) and ethyl acetate (5 mL). The aqueous layer was separated and extracted further with ethyl acetate (2×5 mL). The combined organic layers were dried over sodium sulfate and were concentrated. The residue was purified by flash column chromatography (20% ethyl acetate in hexanes initially, then 40% ethyl acetate in hexanes) to provide (1S,4R,4aS,6aR,7R,12R,12aS,14S,14aS,18Z)-1,2,3,4,7,12,12a,14-octahydro-4-hydroxy-3,3-dimethoxy-1-methyl-7-(trimethylsilyloxy)-8,11-bis[[2-(trimethylsily)ethoxy]methoxy]-4a,14a:7,12-diepoxy-4,14-[3]hexene[1,5]diynonaphtho[2,3-c]phenanthridin-6(6aH)-one (74) as a light yellow oil (7.8 mg, 34%).

Reaction 64:

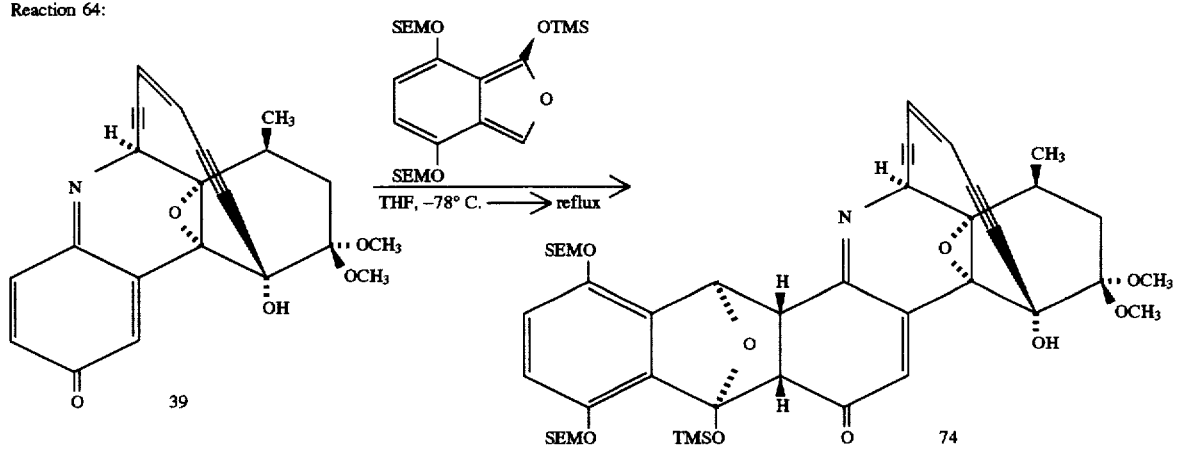

(1S,4R,4aS,6aR,7R,12R,12aS,14S,14aS,18Z)-1,2,3,4,7,12,12a,14-Octahydro-4-hydroxy-3,3-dimethoxy-1-methyl-7-(trimethylsilyloxy)-8,11-bis[[2-(trimethylsily)ethoxy]methoxy]-4a,14a:7,12-diepoxy-4,14-[3]hexene[1,5]diynonaphtho[2,3-c]phenanthridin-6(6aH)-one (74)

A solution of lithium hexamethyldisilazide in tetrahydrofuran (0.090M, 1.09 mL, 0.098 mmol, 3.7 equiv) at −78° C. was transferred via cannula over 5 s to a solution of 4,7-bis[[2-(trimethylsilyl)ethoxyl]methoxy]phthalide (60, 31 mg, 0.073 mmol, 2.7 equiv) in tetrahydrofuran (0.5 mL) at −78° C., and the resulting bright yellow reaction solution was stirred for 15 min at −78° C. Chlorotrimethylsilane was added in two portions (12 µl, 0.095 mmol, 3.6 equiv; 12 µl, 0.095 mmol, 3.6 equiv) to the cold reaction mixture with an Reaction 65:

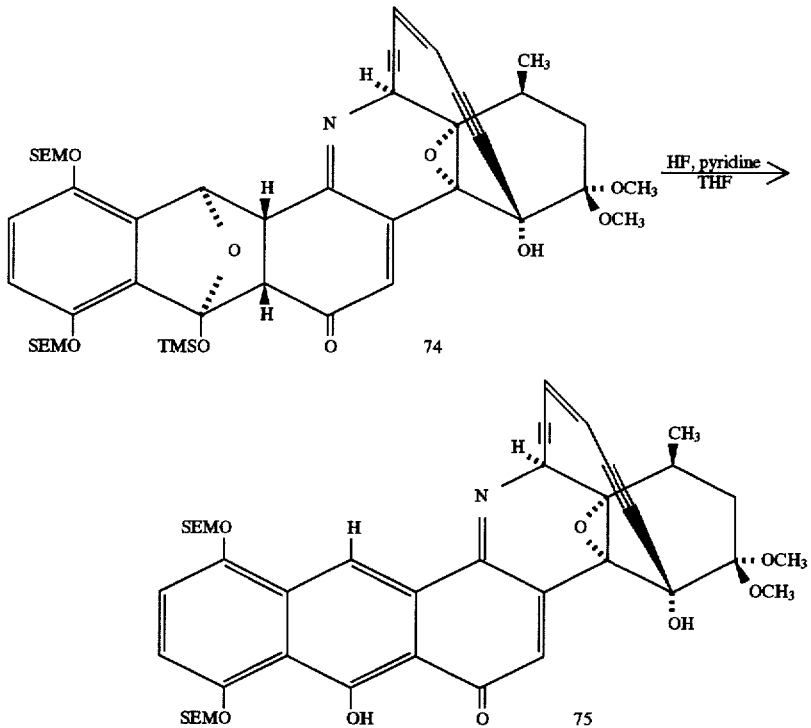

(1S,4R,4aS,14S,14aS,18Z)-1,2,3,4,-Tetrahydro-4-7-dihydroxy-3,3-dimethoxy-1-methyl-8,11-bis[[2-(trimethylsilyl)ethoxy]methoxy]-4a,14a-epoxy-4,14-[3]hexene[1,5]diynonaphtho[2,3-c]phenanthridin-6(14H)-one (75)

A solution of hydrogen fluoride-pyridine in tetrahydrofuran at 0° C. was prepared by the addition of 70% hydrogen fluoride in pyridine (1.0 mL) to a solution of pyridine (4.0 mL) in tetrahydrofuran (10.0 mL) at 0° C. A 500-mL aliquot of this solution was added to a solution of (1S,4R,4aS,6aR,7R,12R,12aS,14S,14aS,18Z)-1,2,3,4,7,12,12a,14-octahydro-4-hydroxy-3,3-dimethoxy-1-methyl-7-(trimethylsilyloxy)-8,11 -bis[[2-(trimethylsilyl)ethoxy]methoxy]-4a,14a:7,12-diepoxy-4,14-[3]hexene[1,5]diynonaphtho[2,3-c]phenanthridin-6(6aH)-one (74, 7.0 mg, 0.0080 mmol, 1 equiv) in tetrahydrofuran (3 mL) at 23° C. The reaction mixture was stirred for 45 min at 23° C., then was partitioned between saturated aqueous sodium bicarbonate solution (30 mL) and ethyl acetate (10 mL). The organic layer was dried over sodium sulfate and was concentrated. The residue was purified by flash column chromatography (30% ethyl acetate in hexanes) to afford (1S, 4R,4aS,14S,14aS,18Z)-1,2,3,4,-tetrahydro-4-7-dihydroxy-3,3-dimethoxy-1-methyl-8,11-bis[[2-(trimethylsilyl)ethoxy]methoxy]-4a,14a-epoxy-4,14-[3]hexene[1,5]diynonaphtho[2,3-c]phenanthridin-6(14H)-one (75) as a red oil (2.3 mg, 37%).

Reaction 66:

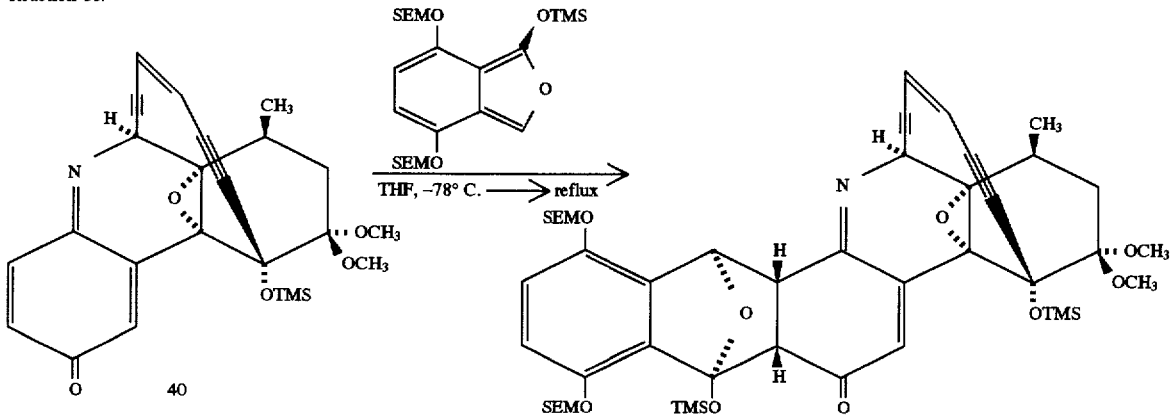

87

(1S,4R,4aS,6aR,7R,12R,12aS,14S,14aS,18Z)-1,2,3,
4,7,12,12a,14-octahydro-4,7-bis(trimethylsilyloxy)-
3,3-dimethoxy-1-methyl-8,11-bis[[2-(trimethylsily)
ethoxy]methoxy]-4a,14a:7,12-diepoxy-4,14-[3]
hexene[1,5]diynonaphtho[2,3-c]phenanthridin-6
(6aH)-one A solution of lithium hexamethyldisilazide in tetrahydrofuran (0.077M, 1.08 mL, 0.084 mmol, 4.9 equiv) at −78° C. was transferred via cannula over 5 s to a solution of

88

14a:7,12-diepoxy-4,14-[3]hexene[1,5]diynonaphtho[2,3-c] phenanthridin-6(6aH)-one as a light yellow oil (5.2 mg, 32%).

Reaction 67:

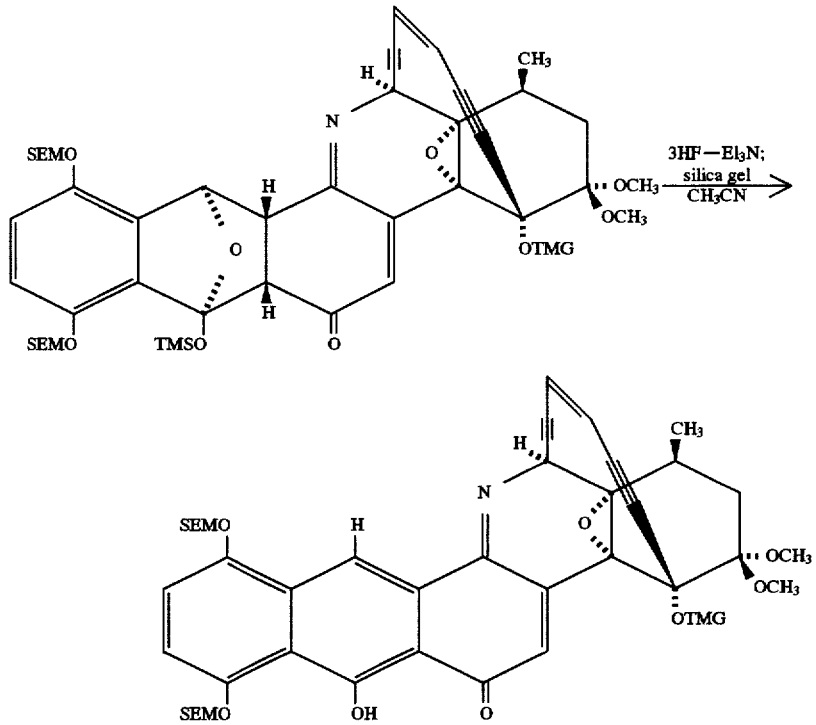

4,7-bis[[2-(trimethylsilyl)ethoxyl]methoxy]phthalide (60, 32 mg, 0.075 mmol, 4.3 equiv) in tetrahydrofuran (0.5 mL) at −78° C., and the resulting bright yellow solution was stirred for 20 min at −78° C. Chlorotrimethylsilane (30 μL, 0.24 mmol, 14 equiv) was added to the cold reaction mixture. The reaction solution became colorless after 10 min at −78° C. A solution of (6S,6aS,7S,10R,10aR,14Z)-7,8,9,10-tetrahydro-9,9-dimethoxy-7-methyl-10-(trimethylsiloxy)-6a,10a-epoxy-6,10-[3]hexene[1,5]= diynophenanthridin-2(6H)-one (40, 7.8 mg, 0.017 mmol, 1 equiv) in tetrahydrofuran (1 mL) at 23° C. was transferred via cannula over 5 s to the cold reaction mixture. The cooling bath was removed, and the reaction mixture was heated to reflux within 2 min using a heat gun. The reaction mixture was held at reflux for 10 min, then was allowed to cool to 23° C. The product solution was partitioned between saturated aqueous sodium bicarbonate solution (20 mL) and ethyl acetate (20 mL). The aqueous layer was separated and extracted further with ethyl acetate (20 mL). The combined organic layers were dried over sodium sulfate and were concentrated. The residue was purified by flash column chromatography (20% ethyl acetate in hexanes initially, then 40% ethyl acetate in hexanes) to provide (1S,4R,4aS,6aR, 7R,12R,12aS,14S,14aS,18Z)-1,2,3,4,7,12,12a,14-octahydro-4,7-bis(trimethylsilyloxy)-3,3-dimethoxy-1-methyl-8,11-bis[[2-(trimethylsily)ethoxy]methoxy]-4a, (1S,4R,4as,14S,14aS,18Z)-1,2,3,4,-Tetrahydro-3,3-
dimethoxy-4-hydroxy-1-methyl-7-trimethylsilyl-8,
11-bis [[2-(trimethylsily)ethoxy]methoxy]-4a,14a-
epoxy-4,14-[3]hexene[1,5]diynonaphtho[2,3-c]
phenanthridin-6(14H)-one Triethylamine trihydrofluoride (10 μL, 0.061 mmol, 23 equiv) was added to a solution of (1S,4R,4aS,6aR,7R,12R, 12aS,14S,14aS,18Z)-1,2,3,4,7,12,12a,14-octahydro-4,7-bis (trimethylsilyloxy)-3,3-dimethoxy-1-methyl-8,11-bis[[2-(trimethylsily)ethoxy]methoxy]-4a,14a:7,12-diepoxy-4,14-[3]hexene[1,5]diynonaphtho[2,3-c]phenanthridin-6(6aH)-one (2.5 mg, 0.0026 mmol, 1 equiv) in acetonitrile (1.5 mL) at 23° C., and the reaction solution was stirred for 1 h at 23° C. The yellow product solution was partitioned between saturated aqueous sodium bicarbonate solution (20 mL) and ethyl acetate (20 mL). The aqueous layer was separated and extracted further with ethyl acetate (20 mL). The combined organic layers were dried over sodium sulfate and were concentrated. Silica gel (100 mg) was added to a solution of the residue in benzene (1.0 mL) at 23° C., and the slurry was stirred for 1 h at 23° C. During this time, the yellow slurry darkened to a red color. The slurry was concentrated and the residue was purified by flash column chromatography (10% ethyl acetate in hexanes initially, then 20% ethyl acetate in hexanes) to provide (1S,4R,4aS,14S,14aS,18Z)-1,2,3,4,- tetrahydro-3,3-dimethoxy-4-hydroxy-1-methyl-7-trimethylsilyl-8,11-bis[[2-(trimethylsily)ethoxy]methoxy]-4a,14a-epoxy-4,14-[3]hexene[1,5]diynonaphtho[2,3-c]phenanthridin-6(14H)-one as a red oil (1.0 mg, 44%).

were concentrated. The residue was purified by flash column chromatography (30% ethyl acetate in hexanes initially, then 40% ethyl acetate in hexanes) to provide together methyl (1S,4R,4aR,6aR,7R,12R,12aS,14S,14aS,18Z)-1,4,6,6a,7, Reaction 68:

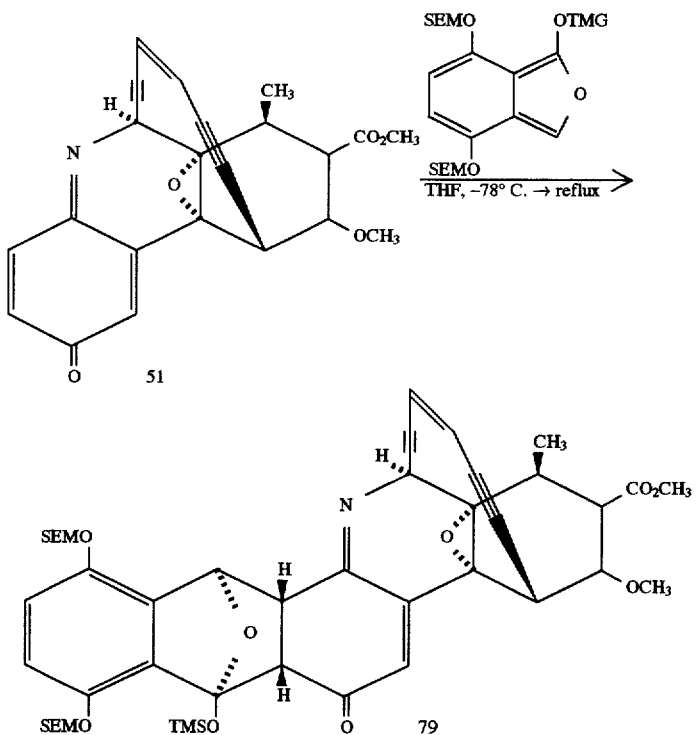

Methyl(1S,4R,4aR,6aR,7R,12R,12aS,14S,14aS,18Z)-1,4,6,6a,7,12,12a,14-Octahydro-3-methoxy-1-methyl-6-oxo-7,8,11-tris(trimethylsiloxy)-14a,14a:7,12-diepoxy-4,14-[3]hexene[1,5]diynonaphtho[2,3,c]phenanthridine-2-carboxylate (79)

A solution of lithium hexamethyldisilazide in tetrahydrofuran (0.059M, 1.1 mL, 0.063 mmol, 4.9 equiv) at −78° C. was transferred via cannula over 5 s to a solution of 4,7-bis[[2-(trimethylsilyl)ethoxyl]methoxy]phthalide (60, 22 mg, 0.052 mmol, 4.0 equiv) in tetrahydrofuran (0.5 mL) at −78° C., and the resulting bright yellow solution was stirred for 20 min at −78° C. Chlorotrimethylsilane was added in two portions (9 μL, 0.071 mmol, 5.5 equiv; 9 μL, 0.071 mmol, 5.5 equiv) to the cold reaction mixture with an interval of 5 min between additions. The reaction mixture became colorless upon the final addition of chlorotrimethylsilane. A solution of methyl(6S,6aS,7S,10R,10aR,14Z)-2,6,7,10-tetrahydro-9-methoxy-7-methyl-2-oxo-6a,10a-epoxy-6,10-[3]hexene[1,5]diynophenan-thridine-8-carboxylate (51, 5.0 mg, 0.013 mmol, 1 equiv) in tetrahydrofuran (1 mL) at 23° C. was transferred over 5 s via cannula to the cold reaction mixture. The cooling bath was removed and the reaction mixture was heated to reflux within 2 min using a heat gun. When the reaction began to boil, heating was discontinued and the flask was allowed to cool to 23° C. The product solution was partitioned between saturated aqueous sodium bicarbonate solution (10 mL) and ethyl acetate (10 mL). The aqueous layer was separated and extracted further with ethyl acetate (2×10 mL). The combined organic layers were dried over sodium sulfate and 12,12a,14-octahydro-3-methoxy-1-methyl-6-oxo-7,8,11-tris(trimethylsiloxy)-4a,14a:7,12-diepoxy-4,14-[3]hexene[1,5]diynonaphtho[2,3,c]phenanthridine-2-carboxylate (79) and methyl(1S,4R,4aR,14S,14aS,18Z)-1,4,7,12,13,14-hexahydro-3-trihydroxy-3-methoxy-1-methyl-7,2-dioxo-4a,14a-epoxy-4,14-[3]hexene[1,5]diynonaphtho[2,3,c]phenanthridine-2-carboxylate (80) (2:1 ratio, respectively) as a light yellow oil (3.4 mg, 30%).

Reaction 69:

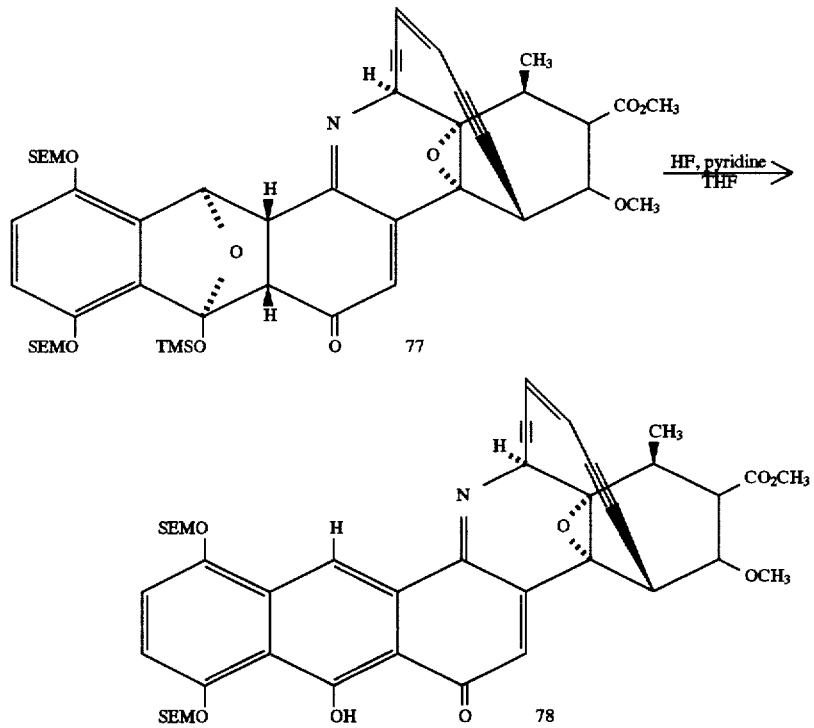

Methyl(1S,4R,4aR,14S,14aS,18Z)-1,4,6,14-Tetrahydro-7-hydroxy-3-methoxy-1-methyl-6-oxo-8,11-bis[[(2-trimethylsilyl)ethoxy]methoxy]-4a,14a-epoxy-4,14-[3]hexene[1,5]diynonaphtho[2,3,c]phenanthridine-2-carboxylate (76)

A solution of hydrogen fluoride-pyridine in tetrahydrofuran at 0° C. was prepared by the addition of 70% hydrogen fluoride in pyridine (1.0 mL) to a solution of pyridine (4.0 mL) in tetrahydrofuran (10.0 mL) at 0° C. A 700-μL aliquot of this solution was added to a solution of methyl(1S,4R,4aR,6aR,7R,12R,12aS,14S,14aS,18Z)-1,4,6,6a,7,12,12a,14-octahydro-3-methoxy-1-methyl-6-oxo-7-(trimethylsiloxy)-8,11-bis[[(2-trimethylsilyl)ethoxy]methoxy]-4a,14a:7,12-diepoxy-4,14-[3]hexene[1,5]diynonaphtho[2,3,c]phenanthridine-2-carboxylate (77, 3.0 mg, 0.0034 mmol, 1 equiv) in tetrahydrofuran (2 mL) at 23° C. The reaction mixture was stirred for 2 h at 23° C., then was partitioned between saturated aqueous sodium bicarbonate solution (30 mL) and ethyl acetate (20 mL). The aqueous layer was separated and extracted further with ethyl aceate (20 mL). The combined organic layers were dried over sodium sulfate and were concentrated. The residue was purified by flash column chromatography (20% ethyl acetate in hexanes initially, then 40% ethyl acetate in hexanes) to afford methyl(1S,4R,4aR,14S,14aS,18Z)-1,4,6,14-tetrahydro-7-hydroxy-3-methoxy-1-methyl-6-oxo-8,11-bis[[(2-trimethylsilyl)ethoxy]methoxy]-4a,14a-epoxy-4,14-[3]hexene[1,5]diynonaphtho[2,3,c]phenanthridine-2-carboxylate (76) as a red oil (0.90 mg, 33%).

Reaction 70:

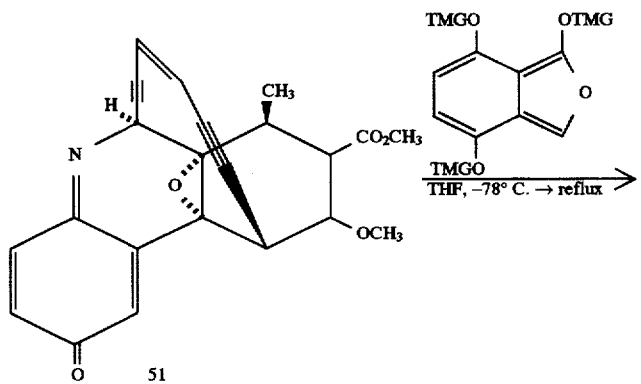

Reaction 70:

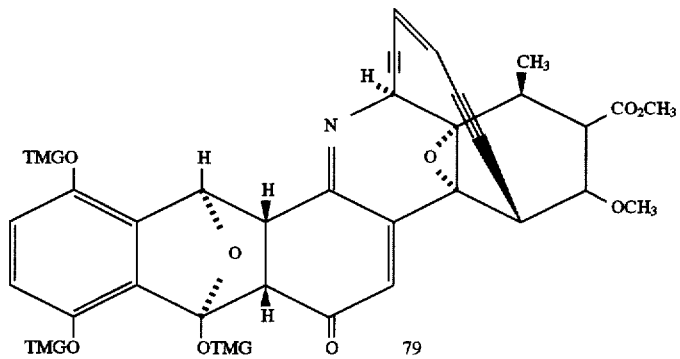

Methyl(1S,4R,4aR,6aR,7R,12R,12aS,14S,14aS,18Z)-1,4,6,6a,7,12,12a,14-Octahydro-3-methoxy-1-methyl-6-oxo-7,8,11-tris(trimethylsiloxy)-4a,14a:7,12-diepoxy-4,14-[3]hexene[1,5]diynonaphtho[2,3,c]phenanthridine-2-carboxylate (79)

A solution of potassium bis(trimethylsilyl) amide (0.5M, 400 μL, 0.200 mmol, 6.46 equiv) was added to a solution of 4,7-bis(trimethylsiloxy)phthalide (59, 60 mg, 0.19 mmol, 6.2 equiv) in tetrahydrofuran (2.5 mL) at −78° C., and the resulting bright yellow solution was stirred for 25 min at −78° C. During this time, the reaction mixture darkened to yellow-brown. Chlorotrimethylsilane (75 μL, 0.59 mmol, 19 equiv) was added, and the reaction mixture was stirred at −78° C. for 5 min. The addition of chlorotrimethylsilane caused the reaction mixture to become bright yellow. After 5 min at −78° C., the viscous reaction mixture was warmed to −50° C. and was swirled manually until the reaction mixture became colorless. At this point, the reaction solution was cooled to −78° C. A solution of methyl(6S,6aS,7S,10R,10aR,14Z)-2,6,7,10-tetrahydro-9-methoxy-7-methyl-2-oxo-6a,10a-epoxy-6,10-[3]hexene[1,5]diynophenanthridine-8-carboxylate (51, 12 mg, 0.031 mmol, 1 equiv) in tetrahydrofuran (1.0 mL) at 23° C. was transferred via cannula over 5 s to the cold reaction mixture. The cooling bath was removed and the reaction solution was heated to reflux within 2 min using a heat gun. When the reaction mixture began to boil, heating was discontinued and the flask was allowed to cool to 23° C. The reaction solution was concentrated to afford a light yellow residue. Analysis of the residue by $^1$H NMR spectroscopy using dichloromethane as an internal standard indicated that the methyl(1S,4R,4aR,6aR,7R,12R,12aS,14S,14aS,18Z)-1,4,6,6a,7,12,12a,14-octahydro-3-methoxy-1-methyl-6-oxo-7,8,11-tris(trimethylsiloxy)-4a,14a:7,12-diepoxy-4,14-[3]hexene[1,5]diynonaphtho[2,3,c]phenanthridine-2-carboxylate (79) had been formed in 61% yield.

Reaction 71:

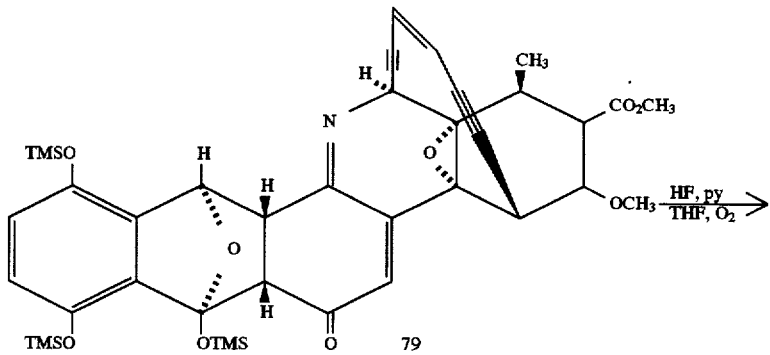

Reaction 71:

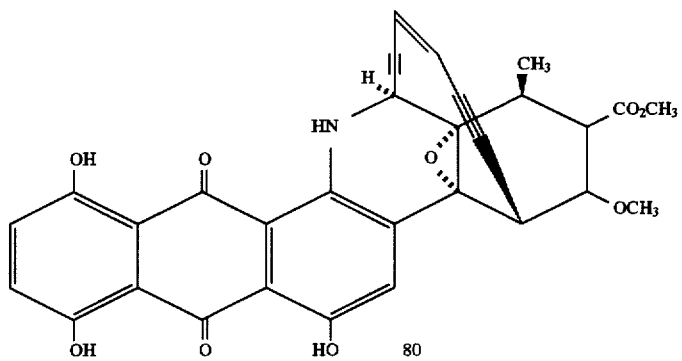

Methyl(1S,4R,4aR,14S,14aS,18Z)-1,4,7,12,13,14-Hexahydro-3-trihydroxy-3-methoxy-1-methyl-7,12-dioxo-4a,14a-epoxy-4,14-[3]hexene[1,5]diynonaphtho[2,3,c]-phenanthridine-2-carboxylate (80)

A solution of hydrogen fluoride-pyridine in tetrahydrofuran at 0° C. was prepared by the addition of 70% hydrogen fluoride in pyridine (1.0 mL) to a solution of pyridine (3.5 mL) in tetrahydrofuran (10 mL) at 0° C. A 350-μl aliquot of this solution was added to a yellow-brown suspension of unpurified methyl(1S,4R,4aR,6aR,7R,12R,12aS,14S,14aS,18Z)-1,4,6,6a,7,12,12a,14-octahydro-3-methoxy-1-methyl-6-oxo-7,8,11-tris(trimethylsiloxy)-4a,14a:7,12-diepoxy-4,14-[3]hexene[1,5]diynonaphtho[2,3,c]phenanthridine-2-carboxylate (79, 0.0051 mmol, 1 equiv) and copper (1) chloride (22.2 mg, 0.224 mmol, 44.3 equiv) in pyridine (2.5 mL) at 23° C. under an atmosphere of oxygen. The resulting dark brown reaction mixture was stirred for 45 min at 23° C. The product suspension was partitioned between ethyl acetate (20 mL) and saturated aqueous sodium bicarbonate solution (30 mL). The aqueous layer was separated and further extracted with ethyl acetate (20 mL). The combined organic layers were washed with five 15-mL portions of saturated aqueous sodium bicarbonate solution. The organic layer was dried over sodium sulfate and was concentrated. Analysis of the blue residue by $^1$H NMR spectroscopy using dichloromethane as an internal standard indicated that methyl(1S,4R,4aR,14S,14aS,18Z)-1,4,7,12,13,14-hexahydro-3-trihydroxy-3-methoxy-1-methyl-7,12-dioxo-4a,14a-epoxy-4,14-[3]hexene[1,5]diynonaphtho[2,3,c] phenanthridine-2-carboxylate (80) had formed in 15% yield.

Example 4

DNA Cleaving Assays
Preparation of 32P-labeled 193 base pair restriction fragment Plasmid pBR322 (40 μl, 0.25 μg/μL, Boehringer Mannheim) was precipitated by the addition of aqueous ammonium acetate buffer solution (20 μL, 8M, pH 7) and ehtanol (180 μL), followed by centrifugation at 2° C. (16,000 g, 30 min) then washed with aqueous ethanol (100 μL, 70%). The DNA pellet was dried on a Savant rotary speed vac, then dissolved in water (80 μL). Digestion Buffer H (10 μL, Boehringer Mannheim) was added, and the plasmid was digested with Eco RI (4 μL, 40 units, Boehringer Mannheim) and SsPI (4 μL, 40 units, Boehringer Mannheim) at 37° C. for 6 hours. The digest was quenched by two extractions with phenol:chloroform (100 μL, 1:1 v/v), and the DNA was precipitated by the addition of aqueous ammonium acetate buffer solution (50 μL, 8M, pH 7) and eithanol (400 μL), followed by centrifugation at 2° C. (16,000, 30 min). The DNA pellet was washed with aqueous ethanol (100 μL, 70%) and dried. The DNA was dissolved in water (18 μL), then mixed with aqueous dithiothreitol solution (4 μL, 100 mM), Sequenase 2.0 Buffer (8 μL, USB), and [α-32P]-dATP (10 μL, 100 μCi, NEN, >6000 Ci/mmol). The restriction fragment was 3'-labeled with Sequenase Version 2.0 (2 μL, 25 units, USB) at 37° C. for 3 h, then treated with aquoeus dATP solution (5 μL, 10 mM) and Sequenase Version 2.0 (1 μL, 12 units, USB) and incubated further at 37° C. for I h. The reaction solution was eluted through a NICK column (Pharmacia) to remove unincorporated 32P-ATP, and the eluent containing the labeled fragment was concentrated to a volume of 100 μL. The labeled fragment was precipitated by the addition of aqueous ammonium acetate buffer solution (100 μL, 8M, pH 7), and ethanol (500 μL), followed by centrifugation at 2° C., as previously, then washed with aqueous ethanol (100 μL, 70%) and dried. The 193 basepair fragment was purified over a 8% nondenaturing polyacrylamide gel, 0.8 mm thickness. The band containing the fragment was located by autoradiography and exised. The gel slice was crushed thoroughly and, after combination with aqueous Nonidet P-40 detergent solution (500 μL, 0.05%, Sigma) was vortexed for 3 h at 23° C. The resulting suspension was filtered through a Centrex filter (0.45 μm) and the filtrate was extracted twice with phenol:chloroform (300 μL) and concentrated to 100 μL. The labeled product was precipitated by the addition of aqueous ammonium acetate buffer solution (100 μL, 8M, pH 7) and ethanol (500 μL), followed by centrifugation at 2° C. as above and washed with aqueous ethanol. The purified labeled fragment was stored frozen in tris-HCl buffer (10 mM, pH 7.4) with EDTA (1 mM).

Analysis of DNA Cleavage by dynemicin analogs

Structures 73, 84, 87, and 88 were used to cleave the fragment. Reactions were performed at 37° C. with a total reaction volume of 50 μL. A 5 μL aliquot of freshly prepared solution of structure 73 (0.05 mM) in methanol was combined with a solution of double stranded calf thymus DNA (5 μL, 1.0 mM) in water, tris-HCl buffer (10 μL, 500 mM, pH 7.5), sodium chloride (10 μL, 500 mM), 15 μL water, and labeled restriction fragment (~50,000 cpm). The reaction was initiated at 23° C. by the addition of glutathione (5 μL, 200 mM, pH 7.5) to the remaining solution, resulting in the following concentrations of components at the onset of the reaction: 5 μM structure 73; 20 mM GSH; 0.1 mM bp calf thymus DNA; 100 mM tris buffer; 100 mM NaCl. The reaction solution was incubated at 37° C. for 12 hours, and the cleavage products analyzed as described below. Structures 84, 87, and 88, and dynemicin A were used identically.

Analysis of DNA Cleavage Product

The products from a given DNA cleavage reaction were precipitated by the addition of aqueous ammonium acetate buffer solution (50 µL, 8M, pH 7) and 250 µL ethanol, followed by centrifugation and washing as above. The pellet was dissolved in 8 µL formamide loading buffer and transferred to a fresh tube. After assaying for radioactivity in a Bechman LS 6000SC scintillation counter, the solution was diluted with additional formamide buffer to produce a radiation density of 2000 cpm/µL. After denaturing at 85° C. for 3 min, the 5 µL solution was analyzed by gel electrophoresis. Cleavage products from the fragment were loaded onto a 8% denaturing polyacrylamide gel and separated by electrophoresis in 1× TBE buffer at 2000 V for 15 min and then at 1500 V until the bromophenol blue dye had migrated off the gel. The gel was exposed to a storage phosphor plate and the DNA cleavage products were quantified with a molecular Dynamics 400S PhosphorImager.

The results, shown in FIG. 2, show that structures 73, 84 and 88 cleave DNA in a manner similar to dynemicin A.

Example 5

Anti-tumor Assays

Structures 73, 84, 25, and 39 were sent to the National Cancer Institute for in vitro disease-oriented primary anti-tumor screening. The screen is described in Seminars in Oncology. Briefly, the compounds were tested against 60 different cell lines of 9 cancer types, at a minimum of five concentrations at 10 fold dilutions. A 48 hour continuous drug exposure protocol is used, and a sulforhodamine B (SRB) protein assay is used to estimate cell viability or growth.

The pattern of inhibition of growth and/or cell death on the 59 cell lines generates a "fingerprint". The "fingerprint" can then be compared to the fingerprint of known chemotherapeutic compounds, thus associating a fingerprint with a particular mode of action. In the case of the dynemicin analogs, it appears that their fingerprint is similar to the fingerprint of a compound currently in clinical trials, which has been associated with the inhibition of topoisomerase.

All of the structures resulted in suppression of cell growth on all cancer types and on most cell lines.

I claim:

1. A quinone imine dynemicin analog having the formula comprising:

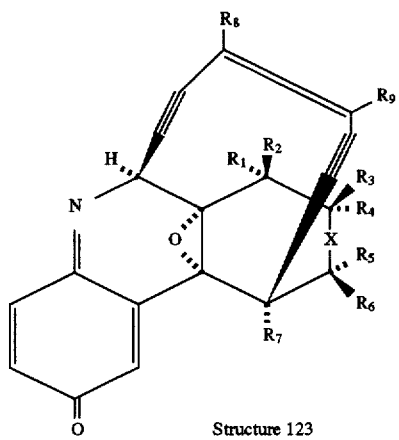

Structure 123 wherein $R_1$ is hydrogen, hydroxy, alkyl, aryl, amine, alkyl amine, alkyl ether, alkoxy, carboxy, carbonyl oxygen, substituted carbonyl, sulfur containing moiety, phosphorus containing moiety, halide, a protecting group;

$R_2$ is hydrogen, hydroxy, alkyl, aryl, amine, alkyl amine, alkyl ether, alkoxy, carboxy, substituted carbonyl, sulfur containing moiety, phosphorus containing moiety, halide, a protecting group, or is absent when $R_1$ is carbonyl oxygen;

$R_7$ is hydrogen, hydroxy, alkyl, aryl, amine, alkyl amine, alkyl ether, alkoxy, carboxy, substituted carbonyl, sulfur containing moiety, phosphorus containing moiety, halide, or a protecting group;

$R_8$ is hydrogen, hydroxy, alkyl, aryl, amine, alkyl amine, alkyl ether, alkoxy, carboxy, substituted carbonyl, sulfur containing moiety, phosphorus containing moiety, halide, a protecting group or with $R_9$ and the unsaturated vinylene between $R_8$ and $R_9$ form an aryl group;

$R_9$ is hydrogen, hydroxy, alkyl, aryl, amine, alkyl amine, alkyl ether, alkoxy, carboxy, substituted carbonyl, sulfur containing moiety, phosphorus containing moiety, halide, a protecting group or with $R_8$ and the unsaturated vinylene between $R_8$ and $R_9$ an aryl group; and X is a double or a single bond;

wherein when X is a single bond, $R_3$ is hydrogen, carbonyl oxygen, hydroxy, alkyl, aryl, alkoxy, carboxy, substituted carbonyl, sulfur containing moiety, phosphorus containing moiety, amine, alkyl amine, alkyl ether, halide a protecting group, or is absent when $R_1$ is carbonyl oxygen;

$R_4$ is hydrogen, hydroxy, alkyl, aryl, alkoxy, carboxy, substituted carbonyl, sulfur containing moiety, phosphorus containing moiety, amine, alkyl amine, alkyl ether, halide, a protecting group, or is absent when $R_3$ is carbonyl oxygen;

$R_5$ is hydrogen, carbonyl oxygen, hydroxy, alkyl, aryl, alkoxy, carboxy, substituted carbonyl, sulfur containing moiety, phosphorus containing moiety, amine, alkyl amine, alkyl ether, halide or a protecting group;

$R_6$ is hydrogen, hydroxy, alkyl, aryl, alkoxy, carboxy, substituted carbonyl, sulfur containing moiety, phosphorus containing moiety, amine, alkyl amine, alkyl ether, halide, a protecting group, or is absent when $R_5$ is carbonyl oxygen;

wherein when X is a double bond, $R_3$ is is absent;

$R_4$ is hydrogen, hydroxy, alkyl, aryl, alkoxy, carboxy, substituted carbonyl, sulfur containing moiety, phosphorus containing moiety, amine, alkyl amine, alkyl ether, halide or a protecting group;

$R_5$ is is absent; and $R_6$ is hydrogen, hydroxy, alkyl, aryl, alkoxy, carboxy, substituted carbonyl, sulfur containing moiety, phosphorus containing moiety, amine, alkyl amine, alkyl ether, halide or a protecting group.

2. A dynemicin analog having the formula comprising:

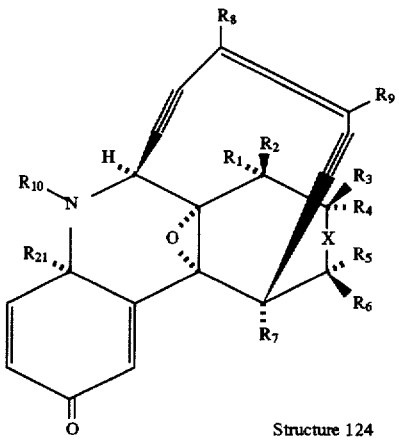

Structure 124 wherein $R_1$ is hydrogen, hydroxy, alkyl, aryl, amine, alkyl amine, alkyl ether, alkoxy, carboxy, carbonyl oxygen, substituted carbonyl, sulfur containing moiety, phosphorus containing moiety, halide, a protecting group;

$R_2$ is hydrogen, hydroxy, alkyl, aryl, amine, alkyl amine, alkyl ether, alkoxy, carboxy, substituted carbonyl, sulfur containing moiety, phosphorus containing moiety, halide, a protecting group, or is absent when $R_1$ is carbonyl oxygen;

$R_7$ is hydrogen, hydroxy, alkyl, aryl, amine, alkyl amine, alkyl ether, alkoxy, carboxy, substituted carbonyl, sulfur containing moiety, phosphorus containing moiety, halide, or a protecting group;

$R_8$ is hydrogen, hydroxy, alkyl, aryl, amine, alkyl amine, alkyl ether, alkoxy, carboxy, substituted carbonyl, sulfur containing moiety, phosphorus containing moiety, halide, a protecting group or with $R_9$ and the unsaturated vinylene between $R_8$ and $R_9$ form an aryl group;

$R_9$ is hydrogen, hydroxy, alkyl, aryl, amine, alkyl amine, alkyl ether, alkoxy, carboxy, substituted carbonyl, sulfur containing moiety, phosphorus containing moiety, halide, a protecting group or with $R_8$ and the unsaturated vinylene between $R_8$ and $R_9$ an aryl group;

$R_{10}$ is substituted carbonyl;

$R_{21}$ is alkoxy; and

X is a double or a single bond;

wherein when X is a single bond, $R_3$ is hydrogen, carbonyl oxygen, hydroxy, alkyl, aryl, alkoxy, carboxy, substituted carbonyl, sulfur containing moiety, phosphorus containing moiety, amine, alkyl amine, alkyl ether, halide or a protecting group;

$R_4$ is hydrogen, hydroxy, alkyl, aryl, alkoxy, carboxy, substituted carbonyl, sulfur containing moiety, phosphorus containing moiety, amine, alkyl amine, alkyl ether, halide, a protecting group, or is absent when $R_3$ is carbonyl oxygen;

$R_5$ is hydrogen, carbonyl oxygen, hydroxy, alkyl, aryl, alkoxy, carboxy, substituted carbonyl, sulfur containing moiety, phosphorus containing moiety, amine, alkyl amine, alkyl ether, halide or a protecting group;

$R_6$ is hydrogen, hydroxy, alkyl, aryl, alkoxy, carboxy, substituted carbonyl, sulfur containing moiety, phosphorus containing moiety, amine, alkyl amine, alkyl ether, halide, a protecting group, or is absent when $R_5$ is carbonyl oxygen;

wherein when X is a double bond, $R_3$ is is absent;

$R_4$ is hydrogen, hydroxy, alkyl, aryl, alkoxy, carboxy, substituted carbonyl, sulfur containing moiety, phosphorus containing moiety, amine, alkyl amine, alkyl ether, halide or a protecting group;

$R_5$ is absent; and $R_6$ is hydrogen, hydroxy, alkyl, aryl, alkoxy, carboxy, substituted carbonyl, sulfur containing moiety, phosphorus containing moiety, amine, alkyl amine, alkyl ether, halide or a protecting group.

3. A dynemicin analog having the formula comprising:

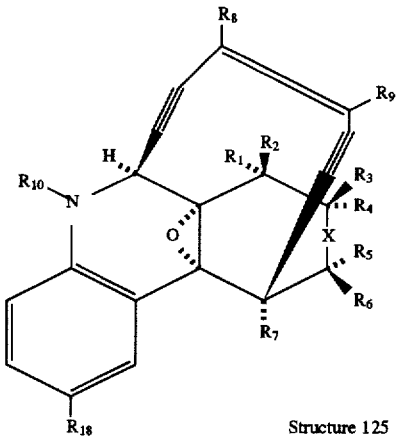

Structure 125 wherein $R_1$ is hydrogen, hydroxy, alkyl, aryl, amine, alkyl amine, alkyl ether, alkoxy, carboxy, carbonyl oxygen, substituted carbonyl, sulfur containing moiety, phosphorus containing moiety, halide, or a protecting group;

$R_2$ is hydrogen, hydroxy, alkyl, aryl, amine, alkyl amine, alkyl ether, alkoxy, carboxy, substituted carbonyl, sulfur containing moiety, phosphorus containing moiety, halide, a protecting group, or is absent when $R_1$ is carbonyl oxygen;

$R_7$ is hydrogen, hydroxy, alkyl, aryl, amine, alkyl amine, alkyl ether, alkoxy, carboxy, substituted carbonyl, sulfur containing moiety, phosphorus containing moiety, halide, or a protecting group;

$R_8$ is hydrogen, hydroxy, alkyl, aryl, amine, alkyl amine, alkyl ether, alkoxy, carboxy, substituted carbonyl, sulfur containing moiety, phosphorus containing moiety, halide, a protecting group or with $R_9$ and the unsaturated vinylene between $R_8$ and $R_9$ form an aryl group;

$R_9$ is hydrogen, hydroxy, alkyl, aryl, amine, alkyl amine, alkyl ether, alkoxy, carboxy, substituted carbonyl, sulfur containing moiety, phosphorus containing moiety, halide, a protecting group or with $R_8$ and the unsaturated vinylene between $R_8$ and $R_9$ an aryl group;

$R_{10}$ is alkoxy;

$R_{18}$ is hydrogen, hydroxy, alkyl, aryl, amine, alkyl amine, alkyl ether, alkoxy, carboxy, substituted carbonyl, sulfur containing moiety, phosphorus containing moiety, halide, or a protecting group; and X is a double or a single bond;

wherein when X is a single bond, $R_3$ is hydrogen, carbonyl oxygen, hydroxy, alkyl, aryl, alkoxy, carboxy, substituted carbonyl, sulfur containing moiety, phosphorus containing moiety, amine, alkyl amine, alkyl ether, halide or a protecting group;

$R_4$ is hydrogen, hydroxy, alkyl, aryl, alkoxy, carboxy, substituted carbonyl, sulfur containing moiety, phosphorus containing moiety, amine, alkyl amine, alkyl ether, halide, a protecting group, or is absent when $R_3$ is carbonyl oxygen;

$R_5$ is hydrogen, carbonyl oxygen, hydroxy, alkyl, aryl, alkoxy, carboxy, substituted carbonyl, sulfur containing moiety, phosphorus containing moiety, amine, alkyl amine, alkyl ether, halide or a protecting group;

$R_6$ is hydrogen, hydroxy, alkyl, aryl, alkoxy, carboxy, substituted carbonyl, sulfur containing moiety, phosphorus containing moiety, amine, alkyl amine, alkyl ether, halide, a protecting group, or is absent when $R_5$ is carbonyl oxygen;

wherein when X is a double bond, $R_3$ is is absent;

$R_4$ is hydrogen, hydroxy, alkyl, aryl, alkoxy, carboxy, substituted carbonyl, sulfur containing moiety, phosphorus containing moiety, amine, alkyl amine, alkyl ether, halide or a protecting group;

$R_5$ is is absent; and $R_6$ is hydrogen, hydroxy, alkyl, aryl, alkoxy, carboxy, substituted carbonyl, sulfur containing moiety, phosphorus containing moiety, amine, alkyl amine, alkyl ether, halide or a protecting group.

4. A dynemicin analog according to claim 3 having the formula:

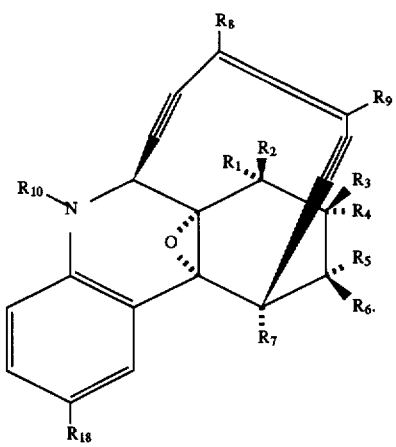

5. A dynemicin analog according to claim 2 having the formula:

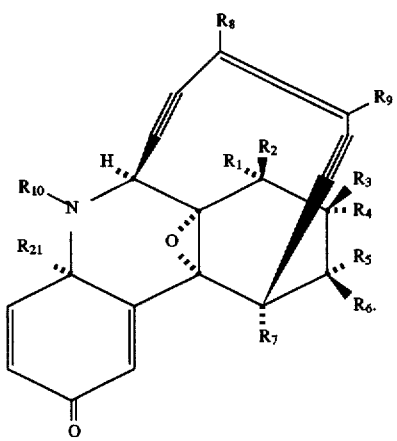

6. A quinone imine dynemicin analog according to claim 3 having the formula:

7. A quinone imine dynemicin analog according to claim 2 having the formula:

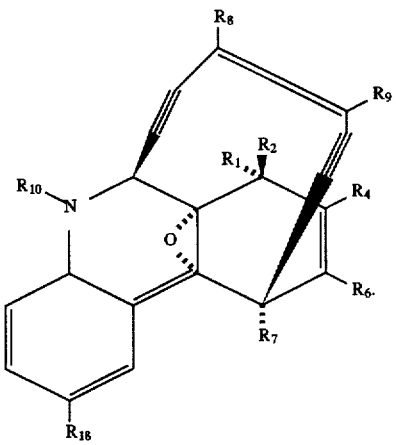

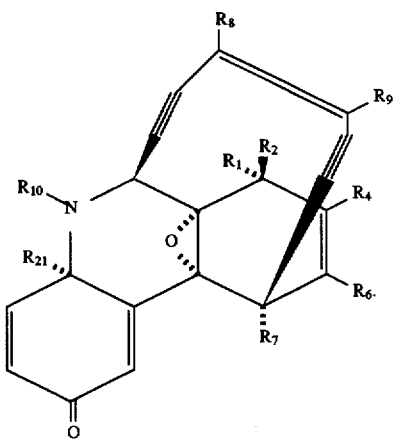

8. A quinone imine dynemicin analog according to claim 1 having the formula:

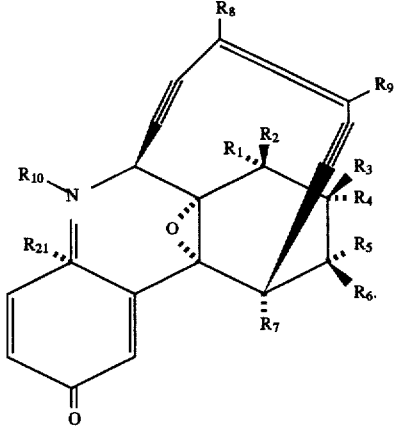

9. A quinone imine dynemicin analog according to claim 1 having the formula:

10. A dynemicin having the formula:

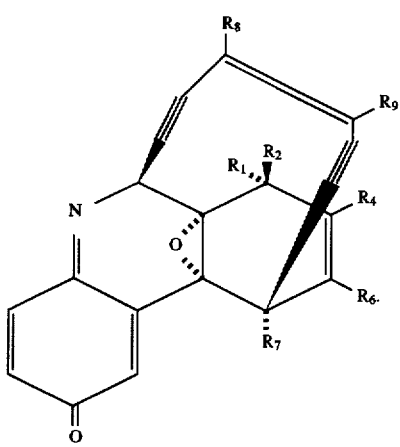

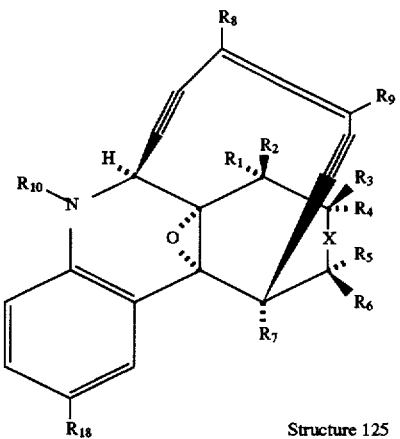

Structure 125 wherein

R$_1$ is hydrogen, hydroxy, alkyl, aryl, amine, alkyl amine, alkyl ether, alkoxy, carboxy, carbonyl oxygen, substituted carbonyl, sulfur containing moiety, phosphorus containing moiety, halide, or a protecting group;

R$_2$ is hydrogen, hydroxy, alkyl, aryl, amine, alkyl amine, alkyl ether, alkoxy, carboxy, substituted carbonyl, sulfur containing moiety, phosphorus containing moiety, halide, a protecting group, or is absent when R$_1$ is carbonyl oxygen;

R$_7$ is hydrogen, hydroxy, alkyl, aryl, amine, alkyl amine, alkyl ether, alkoxy, carboxy, substituted carbonyl, sulfur containing moiety, phosphorus containing moiety, halide, or a protecting group;

R$_8$ is hydrogen, hydroxy, alkyl, aryl, amine, alkyl amine, alkyl ether, alkoxy, carboxy, substituted carbonyl, sulfur containing moiety, phosphorus containing moiety, halide, a protecting group or with R$_9$ and the unsaturated vinylene between R$_8$ and R$_9$ form an aryl group;

R$_9$ is hydrogen, hydroxy, alkyl, aryl, amine, alkyl amine, alkyl ether, alkoxy, carboxy, substituted carbonyl, sulfur containing moiety, phosphorus containing moiety, halide, a protecting group or with R$_8$ and the unsaturated vinylene between R$_8$ and R$_9$ an aryl group;

R$_{10}$ is alkoxy or carboxylate;

R$_{18}$ is hydrogen, hydroxy, alkyl, aryl, amine, alkyl amine, alkyl ether, alkoxy, carboxy, substituted carbonyl, sulfur containing moiety, phosphorus containing moiety, halide, or a protecting group; and X is a double or a single bond;

wherein when X is a single bond,

R$_3$ is hydrogen, carbonyl oxygen, hydroxy, alkyl, aryl, alkoxy, carboxy, substituted carbonyl, sulfur containing moiety, phosphorus containing moiety, amine, alkyl amine, alkyl ether, halide or a protecting group;

R$_4$ is hydrogen, hydroxy, alkyl, aryl, alkoxy, carboxy, substituted carbonyl, sulfur containing moiety, phosphorus containing moiety, amine, alkyl amine, alkyl ether, halide, a protecting group, or is absent when R$_3$ is carbonyl oxygen;

R$_5$ is carbonyl oxygen, hydroxy, alkyl, aryl, alkoxy, carboxy, substituted carbonyl, sulfur containing moiety, phosphorus containing moiety, amine, alkyl amine, alkyl ether, halide or a protecting group;

R$_6$ is hydroxy, alkyl, aryl, alkoxy, carboxy, substituted carbonyl, sulfur containing moiety, phosphorus containing moiety, amine, alkyl amine, alkyl ether, halide, a protecting group, or is absent when R$_5$ is carbonyl oxygen;

wherein when X is a double bond,

R$_3$ is is absent;

R$_4$ is hydrogen, hydroxy, alkyl, aryl, alkoxy, carboxy, substituted carbonyl, sulfur containing moiety, phosphorus containing moiety, amine, alkyl amine, alkyl ether, halide or a protecting group;

R$_5$ is is absent; and

R$_6$ is hydrogen, hydroxy, alkyl, aryl, alkoxy, carboxy, substituted carbonyl, sulfur containing moiety, phosphorus containing moiety, amine, alkyl amine, alkyl ether, halide or a protecting group.

11. A dynemicin analog according to claim 10 having the formula:

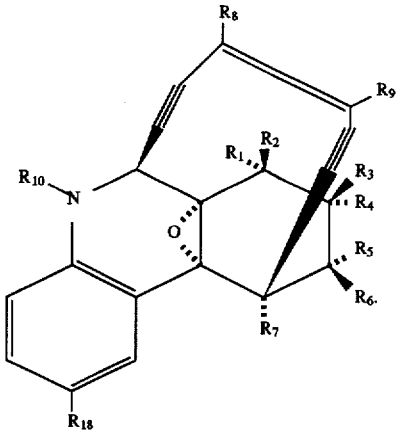

12. A radiolabeled dynemicin analog according to claims 1, 2, 3 or 10.

13. A method of inhibiting the growth of cells in a mammalian host comprising administering a therapeutic amount of a dynemicin analog according to claim 1, 2, 3, or 10 said host.

14. A pharmaceutical composition comprising the compound of claim 1, 2, 3, or 10 in admixture with a pharmaceutically acceptable carrier.

* * * * *

UNITED STATES PATENT AND TRADEMARK OFFICE
CERTIFICATE OF CORRECTION

PATENT NO. : 5,763,451
DATED : June 9, 1998
INVENTOR(S) : MYERS

It is certified that error appears in the above-indentified patent and that said Letters Patent is hereby corrected as shown below:

Column 1, immediately preceding BACKGROUND OF THE INVENTION, insert a new paragraph to read --This invention was made with Government support under contract CA 47148-07 awarded by the National Institutes of Health. The Government has certain rights in this invention.--.

Signed and Sealed this

Seventh Day of September, 1999

Attest:

Q. TODD DICKINSON

*Attesting Officer*    *Acting Commissioner of Patents and Trademarks*